United States Patent
Van Den Pol et al.

(10) Patent No.: US 10,821,143 B2
(45) Date of Patent: *Nov. 3, 2020

(54) CHIMERIC VSV VIRUS COMPOSITIONS AND METHODS OF USE THEREOF FOR TREATMENT OF CANCER

(71) Applicant: Yale University, New Haven, CT (US)

(72) Inventors: Anthony N. Van Den Pol, Branford, CT (US); Guido Wollmann, Innsbruck (AT)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,425

(22) Filed: Dec. 28, 2018

(65) Prior Publication Data

US 2019/0117711 A1   Apr. 25, 2019

Related U.S. Application Data

(63) Continuation of application No. 15/037,774, filed as application No. PCT/US2014/067137 on Nov. 24, 2014, now Pat. No. 10,179,154.

(60) Provisional application No. 61/907,520, filed on Nov. 22, 2013.

(51) Int. Cl.

| | |
|---|---|
| *A61K 35/766* | (2015.01) |
| *C12N 7/04* | (2006.01) |
| *A61K 35/76* | (2015.01) |
| *A61K 39/205* | (2006.01) |
| *A61K 39/12* | (2006.01) |
| *A61K 9/00* | (2006.01) |
| *A61K 35/12* | (2015.01) |
| *A61K 45/06* | (2006.01) |
| *C12N 7/00* | (2006.01) |
| *A61K 39/00* | (2006.01) |

(52) U.S. Cl.
CPC ............ *A61K 35/766* (2013.01); *A61K 9/007* (2013.01); *A61K 9/0019* (2013.01); *A61K 9/0043* (2013.01); *A61K 35/12* (2013.01); *A61K 39/205* (2013.01); *A61K 45/06* (2013.01); *C12N 7/00* (2013.01); *C12N 7/04* (2013.01); *A61K 2039/5152* (2013.01); *A61K 2039/5256* (2013.01); *C12N 2760/20133* (2013.01); *C12N 2760/20222* (2013.01); *C12N 2760/20223* (2013.01); *C12N 2760/20232* (2013.01); *C12N 2760/20234* (2013.01)

(58) Field of Classification Search
None
See application file for complete search history.

(56) References Cited

U.S. PATENT DOCUMENTS

| | | |
|---|---|---|
| 6,440,730 B1 | 8/2002 | Von Laer |
| 7,081,243 B1 | 7/2006 | Rose |
| 7,153,510 B1 | 12/2006 | Rose |
| 8,012,489 B2 | 9/2011 | Jones |
| 2007/0026012 A1 | 2/2007 | Delisa |
| 2007/0218078 A1 | 9/2007 | Clarke |
| 2009/0175906 A1 | 7/2009 | Kalyan |
| 2011/0250188 A1 | 10/2011 | Von Laer |
| 2012/0171246 A1 | 7/2012 | van den Pol |
| 2014/0301992 A1 | 10/2014 | von Laer |

FOREIGN PATENT DOCUMENTS

| | | |
|---|---|---|
| WO | 2003005964 | 1/2003 |
| WO | 2010080909 | 7/2010 |

OTHER PUBLICATIONS

Altomonte et al. Enhanced oncolytic potency of vesicular stomatitis virus through vector-mediated inhibition of NK and NKT cells. Cancer Gene Therapy (2009) 16, 266-278.*
Bergman et al., Virology 316 (2003) 337-347.*
Hastie et al., Journal of General Virology (2012), 93, 2529-2545.*
Muik et al., J Virol. 2011, 85, 5679-5684.*
Ayala-Breton et al., Human Gene Therapy 23:484-491 (May 2012).*
Ahmed, et al., "Identification of a consensus mutation in M protein of vesicular stomatitis virus from persistently infected cells that affects inhibition of host-directed gene expression", Virology,

(56) References Cited

OTHER PUBLICATIONS

Barzon, et al., "HSV-TK/IL-2 gene therapy for glioblastoma multiforme", Methods Mol. Biol., 542:529-49 (2009).
Beier, et al., "Anterograde or retrograde transsynaptic labeling of CNS neurons with vesicular stomatitis virus vectors", PNAS, 108:15414-9 (2011).
Bowen, et al., "Genetic diversity among Lassa virus strains", J. Virology, 6992-7004 (2000).
Buonocore, et al., "Characterization of vesicular stomatitis virus recombinants that express and incorporate high levels of hepatitis C virus glycoproteins", J. Virol., 76:6865-72 (2002).
Chateauvieux, et al., "Molecular and therapeutic potential and toxicity of valproic acid", J. Biomed. Biotechnol., 479364. Epub Jul. 29, 2010 (2010).
Clarke, et al., "Synergistic attenuation of vesicular stomatitis virus by combination of specific G gene truncations and N gene translocations", J. Virol., 81:2056-64 (2007).
Cooper, et al., "Attenuation of recombinant vesicular stomatitis virus-human immunodeficiency virus type 1 vaccine vectors by gene translocations and g gene truncation reduces neurovirulence and enhances immunogenicity in mice", J. Virol., 82:207-19 (2008).
Dalton and Rose, "Vesicular stomatitis virus glycoprotein containing the entire green fluorescent protein on its cytoplasmic domain is incorporated efficiently into virus particles", Virology, 279 (2):414-21 (2001).
Dobrikova, et al., "Recombinant oncolytic poliovirus eliminates glioma in vivo without genetic adaptation to a pathogenic phenotype", Mol. Ther., 16:1865-72 (2008).
Doi, et al., "Transient immunosuppression stops rejection of virus-transduced enhanced green fluorescent protein in rabbit retina", J. Virol, 78(20): 11327-33 (2004).
Drake, et al., "Mutation rates among RNA viruses", PNAS, 96:13910-3 (1999).
Feldmann and Geisbert, "Ebola haemorrhagic fever", Lancet, 377(9768): 849-62 (2011).
Flanagan, et al., "Rearrangement of the genes of vesicular stomatitis virus eliminates clinical disease in the natural host: new strategy for vaccine development", J. Virol., 75:6107-14 (2001).
Flanagan, et al., "Vesicular stomatitis viruses with rearranged genomes have altered invasiveness and neuropathogenesis in mice", J. Virol., 77:5740-8 (2003).
Freeman, et al., "Phase I/II trial of intravenous NDV-HUJ oncolytic virus in recurrent glioblastoma multiforme", Mol. Ther., 13:221-8 (2006).
Fu, et al., "Autophagy induced by valproic acid is associated with oxidative stress in glioma cell lines", Neuro. Oncol., 12:328-40 (2010).
Fukuhara, et al., "Oncolytic herpes simplex virus type 1 and host immune responses", Curr. Cancer Drug Targets, 7:149-55 (2007).
Garbutt, et al., "Properties of replication-competent vesicular stomatitis virus vectors expressing glycoproteins of filoviruses and arenaviruses", J Virol., 78(10):5458-65 (2004).
Geibert and Feldmann, "Recombinant vesicular stomatitis virus-based vaccines against Ebola and Marburg virus infect", J. Infect. Dis., 204 (suppl 3): S1075-S1081 (2011).
Geisbert, et al., "Development of a new vaccine for the prevention of Lassa fever", PLoS Med., 2:e183 (2005a).
Geisbert, et al., "Development of a new vaccine for the prevention of Lassa fever", PLOS, 2(6):e183 (2005b).
Geisbert, et al., "Single-injection vaccine protects nonhuman primates against infection with marburg virus and three species of ebola virus", J Virol., 83(14):7296-7304 (2009).
Geisbert, et al., "Vesicular stomatitis virus-based ebola vaccine is well-tolerated and protects immunocompromised nonhuman primates", PLoS Pathog., 4(11):e1000225 (2008).
GenBank accession NC_002549, "Zaire ebolavirus isolate Ebola virus/*H. sapiens*-tc/COD/1976/Yambuku-Mayinga, complete genome", 12 pages, accessed Sep. 27, 2015, updated Apr. 20, 2016, first appeared, Sep. 27, 2000.

GenBank accession No. AF086833, "Ebola virus—Mayinga, Zaire. 1976, complete genome", 11 pages, accessed Sep. 27, 2015, updated Feb. 12, 2012, first appeared, Feb. 11, 1999.
GenBank: HQ688673.1, "Lassa virus strain recombinant Josiah segment S, complete sequence", 2 pages, accessed Sep. 27, 2015, updated Apr. 7, 2011, first appeared Feb. 22, 2011.
Gire, et al, "Genomic surveillance elucidates Ebola virus origin and transmission during the 2014 outbreak", Science, 345: 1369-72 (2014).
Glaser, "HDAC inhibitors: clinical update and mechanism-based potetial", Biochem. Pharmacol., 74:659-671 (2007).
Günther, et al., "Management of accidental exposure to Ebola virus in the biosafety level 4 laboratory, Hamburg, Germany", J. Infect, Dis., 204 Suppl 3:S785-S790 (2011).
Helland, et al., "A short review of biotechnological methods of relevance to modern vaccine development", Scand J Infect Dis., 76:32-8 (1990).
Hervas-Stubbs, et al., "CD8 T cell priming in the presence of IFN-a renders CTLs with improved responsiveness to homeostatic cytokines and recall antigens: important traits for adoptive T cell therapy", J. Immunol., 189 (7):3299-310 (2012).
Huneycutt, et al., "Distribution of vesicular stomatitis virus proteins in the brains of BALB/c mice following intranasal inoculation: an immunohistochemical analysis", Brain Res., 635:81-95 (1994).
International Search Report and Written Opinion for PCT/US2014/067137 dated Apr. 9, 2015.
Jae, et al., "Deciphering the glycosylome of dystroglycanopathies using haploid screens for lassa virus entry", Science, 340(6151):479-83 (2013).
Jae, et al., Virus entry. Lassa virus entry requires a trigger-induced receptor switch\, Science, 344:1506-1510 (2014).
Jinushi, et al., "Cytokine gene-mediated immunotherapy: current status and future perspectives", Cancer Science, 100:1389-96. (2009).
Johnson, et al., "Neurovirulence properties of recombinant vesicular stomatitis irus vectors in non-human primates", Virology, 360:36-49 (2007).
Jones, et al., "Live attenuated recombinant vaccine protects nonhuman primates against Ebola and Marburg viruses", Nat. Med. 11:786-90 (2005).
Khan et al., "Recombinant vesicular stomatitis virus expressing respiratory syncytial virus (RSV) glycoproteins: RSV fusion protein can mediate infection and cell fusion", Virology, 254:81-91 (1999).
Krishnan, et al., "Niemann-Pick C1 (NPC1)/NPC1-like1 chimeras define sequences critical for NPC1's function as a flovirus entry receptor", Viruses, 4:2471-84 (2012).
Lawson, et al., "Recombinant vesicular stomatitis viruses from DNA", PNAS, 92:4477-4481 (1995).
Lee and Saphire, "Ebolavirus glycoprotein structure and mechanism of entry", Future Virology, 4(6):621-35 (2009).
Liu, et al., "Translation of targeted oncolytic virotherapeutics from the lab into the clinic, and back again: a high-value iterative loop", Mol. Ther., 16:1006-8 (2008).
Lun, et al., "Efficacy and safety/toxicity study of recombinant vaccinia virus JX-594 in two immunocompetent animal models of glioma", Mol. Ther., 18:1927-36 (2010).
Lun, et al., "Efficacy of systemically administered oncolytic vaccinia virotherapy for malignant gliomas is enhanced by combination therapy with rapamycin or cyclophosphamide", Clin. Cancer Res., 15:2777-88 (2009).
Lun, et al., "Myxoma virus is a novel oncolytic virus with significant antitumor activity against experimental human gliomas", Cancer Res, 65:9982-90 (2005).
Lundh, et al., "Non-lethal infection of aminergic reticular core neurons: age-dependent spread of ts mutant vesicular stomatitis virus from the nose", J. Neuropathol. Exp. Neurol., 47:497-506 (1988).
Lyles, "Cytopathogenesis and inhabitation of host gene expression in RNA viruses", Microbiol Mole Biol Rev., December p. 709-24 (2000).
Mactavish, et al., "Enhancement of vaccinia virus based oncolysis with histone deacetylase inhibitors", PLoS One, 5:e14462 (2010).
Maguire, et al., "Preventing growth of brain tumors by creating a zone of resistance", Mol. Ther., 16:1695-1702 (2008).

(56) References Cited

OTHER PUBLICATIONS

Mire, et al., "Recombinant vesicular stomatitis virus vaccine vectors expressing filovirus glycoproteins lack neurovirulence in nonhuman primates", PLoS Negl. Trop Dis, 6:e1567 (2012).

Muik, et al., "Re-engineering vesicular stomatitis virus to abrogate neurotoxicity, circumvent humoral immunity, and enhance oncolytic potency", Cancer Res., 74:3567-78 (2014).

Nandi, et a., "Adenoviral virotherapy for malignant brain tumors", Expert Opin. Biol. Ther., 9:737-747 (2009).

Nguyen, et al., "Chemical targeting of the innate antiviral response by histone deacetylase inhibitors renders refractory cancers sensitive to viral oncolysis", PNAS., 105:14981-6 (2008).

Obuchi, et al., "Development of recombinant vesicular stomatitis viruses that exploit defects in host defense to augment specific oncolytic activity", J. Virol., 77:8843-56 (2003).

Otsuki, et al., "Historic deacetylase inhibitors augment antitumor efficacy of herpes-based oncolytic viruses", Mol. Ther., 16:1546-55 (2008).

Ozduman, et al., "Peripheral immunization blocks lethal actions of vesicular stomatitis virus within the brain", J. Virol., 83:11540-9 (2009).

Ozduman, et al., "Systemic vesicular stomatitis virus selectively destroys multifocal glioma and metastatic carcinoma in brain", J. Neurosci., 28:1882-93 (2008).

Paglino and van den Pol, "Vesicular stomatitis virus has extensive oncolytic activity against human sarcomas: rare resistance is overcome by blocking interferon pathways", J. Virol., 85:9346-58 (2011).

Parker, et al., "Oncolytic viral therapy of malignant glioma", Neurotherapeutics, 6:558-69 (2009).

Pattnaik, et al., "Infectious defective interfering particles of VSV from transcripts of a cDNA clone", Cell, 69:1011-20 (1992).

Peng, et al., "Non-invasive in vivo monitoring of trackable viruses expressing soluble marker peptides", Nat. Med., 8:527-31 (2002).

Phuangsab, et al., "Newcastle disease virus therapy of human tumor xenografts: antitumor effects of local or systemic administration", Cancer Lett., 172:27-36 (2001).

Phuong, et al., "Use of a vaccine strain of measles virus genetically engineered to produce carcinoembryonic antigen as a navel therapeutic agent against glioblastoma multiforme", Cancer Res, 63:2462-9 (2003).

Publicover, et al, "A single-cycle vaccine vector based on vesicular stomatitis virus can induce immune responses comparable to those generated by a replication-competent vector", J. Virol., 79:13231-8 (2005).

Publicover, et al., "Characterization of nonpathogenic, live, viral vaccine vectors inducing potent cellular immune responses", J. Virol., 78:9317-24 (2004).

Ramsburg, et al., "A vesicular stomatitis virus recombinant expressing granulocyte-macrophage colony-stimulating factor induces enhanced T-cell responses and is highly attenuated for replication in animals", J. Virol., 79:15043-53 (2005).

Rigaut, et al., "Intracellular distribution of input vesicular stomatitis virus proteins after uncoating", J. Virol., 65:2622-8 (1991).

Roberts, et al., "Attenuated vesicular stomatitis viruses as vaccine vectors", J. Virol., 73:3723-32 (1999).

Rose, et al., "An effective AIDS vaccine based on live attenuated vesicular stomatitis virus recombinants", Cell, 106:539-49 (2001).

Sanchez, et al., "The virion glycoproteins of Ebola viruses are encoded in two reading frames and are expressed through transcriptional editing", PNAS, 93:3602-7 (1996).

Schell, et al., "Significant protection against high-dose simian immunodeficiency virus challenge conferred by a new prime-boost vaccine regimen", J. Virol., 85:5764-72 (2011).

Schnell, et al., "Foreign glycoproteins expressed from recombinant vesicular stomatitis viruses are incorporated efficiently into virus particles", PNAS, 93:11359-65 (1996).

Schnell, et al., "Requirement for a non-specific glycoprotein cytoplasmic domain sequence to drive efficient budding of vesicular stomatitis virus", EMBO J, 17:1289-96 (1998).

Schnell, et al., "The minimal conserved transcription storp-start signal promotes stable expression of a foreign gene in vesicular stomatitis virus", J. Virol., 70:2318-23 (1996a).

Schwartz, et al, "Potent vesicular stomatitis virus-based avian influenza vaccines provide long-term sterilizing immunity against heterologous challenge", J Virol.,84 (9):4611-8 (2010).

Shashkova, et al., "Anticancer activity of oncolytic adenovirus vector armed with IFN-alpha and ADP is enhanced by pharmacologically controlled expression of TRAIL", Cancer Gene Ther., 15:61-72 (2008).

Simon, et al., "Replication and propagation of attenuated vesicular stomatitis virus vectors in vivo: vector spread correlates with induction of immune responses and persistence of genomic RNA", J. Virol., 81:2078-82 (2007).

Stojdl, et al., "Exploiting tumor-specific defects in the interferon pathway with a previously unknown oncolytic virus", Nat. Med., 6:821-5 (2000).

Stojdl, et al., "VSV strains with defects in their ability to shutdown innate immunity are potent systemic anti-cancer agents", Cancer Cell., 4:263-75 (2003).

Strong, et al., "The molecular basis of viral oncolysis: usurpation of the Ras signaling pathway by reovirus", EMBO J., 17:3351-62 (1998).

Su, et al., "Phase 1 study of valproic acid in pediatric patients with refractory solid or CNS tumors: a children's oncology group report", Clin. Cancer Res., 17:589-97 (2011).

Tesh, et al, "Ecologic studies of vesicular stomatitis virus. I. Prevalence of infection among animals and humans living in an area of endemic VSV activity", Am J Epidemiol., 90 (3)255-61 (1969).

Todo, "Oncolytic virus therapy using genetically engineered herpes simplex viruses", Front Biosci., 13:2060-4 (2008).

Van Den Pol and Davis, et al., "Highly attenuated recombinant vesicular stomatitis virus VSV-12'GFP displays immunogenic and oncolytic activity", J. Virol., 87(2):1019-34 (2013).

Van Den Pol, et al., "Long-distance interferon signaling within the brain blocks virus spread", J. Virol., 88:3695-3704 (2014).

Van Den Pol, et al., "Relative neurotropism of a recombinant rhabdovirus expressing a green fluorescent envelope glycoprotein", J. Virol., 76:1309-27 (2002).

Volchkov, et al., "GP mRNA of Ebola virus is edited by the Ebola virus polymerase and by T7 and vaccinia virus polymerases", Virology, 214(2):421-30 (1995).

Wagner, et al., "Combined treatment of pediatric high-grade glioma with the oncolytic viral strain MTH-68/H and oral valproic acid", APMIS, 114:731-743 (2006).

Wang, et al., "Adoptive transfer of tumor-primed, in vitro-activated, CD4+ T effector cells (TEs) combined with CD8+ TEs provides intratumoral TE proliferation and synergistic antitumor response", Blood, 109(11):4865-72 (2007).

Wang, et al., "Disruption of Erk-dependent type I interferon induction breaks the myxoma virus species barrier", Nature Immunol., 5:1266-74 (2004).

Whelan, et al., "Efficient recovery of infectious vesicular stomatitis virus entirely from cDNA clones", PNAS, 92(18):8388-92 (1995).

Wollmann, et al., "Attenuation of vesicular stomatitis virus infection of brain using antiviral drugs and an adeno-associated virus-interferon vector", Virology, 475:1-15 (2015).

Wollmann, et al., "Oncolytic virus therapy for glioblastoma multiforme: concepts and candidates", Cancer J., 18:69-81 (2012).

Wollmann, et al., "Some attenuated variants of vesicular stomatitis virus show enhanced oncolytic activity against human glioblastoma cells relative to normal brain cells", J Virol., 84:1563-73 (2010).

Wollmann, et al., "Targeting human glioblastoma cells: comparison of nine viruses with oncolytic potential", J. Virol., 79(10): 6005-22 (2005).

Wollmann, et al., "Variable deficiencies in the interferon response enhance susceptibility to vesicular stomatitis virus oncolytic actions in glioblastoma cells but not in normal human glial cells", J. Virol, 81:1479-91 (2007).

Wong, et al., "A forward genetic strategy reveals destabilizing mutations in the Ebolavirus glycoprotein that alter its protease dependence during cell entry", J. Virol., 84(1):163-75 (2010).

(56) References Cited

OTHER PUBLICATIONS

Wongthida, et al., "Activating systemic T-cell immunity against self tumor antigens to support oncolytic virotherapy with vesicular stomatitis virus", Hum. Gene Ther., 22:1343-53 (2011).

Yarde, et al., "Meningeal myeloma deposits adversely impact the therapeutic index of an oncolytic VSV", Cancer Gene Ther., 20:616-21 (2013).

Zemp, et al., "Oncolytic viruses as experimental treatments for malignant gliomas: using a scourge to treat a devil", Cytokine Growth Factor Rev., 21:103-17 (2010).

Bergman et al. Vesicular stomatitis virus expressing a chimeric Sindbis glycoprotein containing an Fc antibody binding domain targets to Her2/neu overexpressing breast cancer cells. Virology 316 (2003) 337-347.

Muik et al. Pseudotyping vesicular stomatitis virus with lymphocytic choriomeningitis virus glycoproteins enhances infectivity for glioma cells and minimizes neurotropism. J Virol. 2011, 85, 5679-5684.

Hastie et al. Vesicular stomatitis virus as a flexible platform for oncolytic virotherapy against cancer. Journal of General Virology (2012), 93, 2529-2545.

Ayala-Breton et al. Retargeting Vesicular Stomatitis Virus Using Measles Virus Envelope Glycoproteins. Human Gene Therapy 23:484-491 (May 2012).
Garbutt et al. Properties of replication-competent vesicular stomatitis virus vectors expressing glycoproteins of filoviruses and arenaviruses. J Virol. May 2004;78(10):5458-65.

* cited by examiner

Glia vs neuron tropism

Fraction of infected

VSV-wtG | LASV | RABV | LCMV | EBOV | MARV
VSV chimera

- glia
- neurons

FIG. 1D

Intracranial virus injection

Percent survival vs Days post-inocculation

- Lassa-VSV
- Ebola-VSV
- VSV-ΔM51
- VSV-1'GFP

FIG. 2A

IC injection (striatum)

FIG. 2B

Infection of human neuronal cultures with VSV

FIG. 3A

CHIMERIC VSV VIRUS COMPOSITIONS AND METHODS OF USE THEREOF FOR TREATMENT OF CANCER

STATEMENT REGARDING FEDERALLY SPONSORED RESEARCH

This invention was made with government support under Grants 1R01CA161048 and RO1 CA175577 awarded by the National Institutes of Health. The government has certain rights in the invention.

FIELD OF THE INVENTION

The invention is generally directed to recombinant vesicular stomatitis virus (VSV) and methods of use thereof to treat cancer, particularly glioblastoma.

BACKGROUND OF THE INVENTION

Patients diagnosed with glioblastoma (GBM) generally have about a year to live. There is no cure for this malignant type of brain cancer. The disease generally manifests with subtle changes in brain function, and becomes worse with seizures, loss of sensation or equilibrium, and progresses to loss of motor function and mental ability, to finally, death. Surgery, focused radiation, and medical treatment may slow the disease down and delay death by several months, but unfortunately, this often comes at the expense of normal function as neurons, glia, and axonal pathways are damaged by the treatment) Wrensch, et al., *Neuro-oncol.*, 4:278-299 (2002)).

Surgery is often done primarily to debulk the tumor, thereby temporarily restoring function to surrounding brain regions that were compressed by tumor expansion. A successful tumor resection may remove billions of tumor cells. But inevitably, due to its infiltrative nature, tens of millions of tumor cells remain within the brain after surgery (Croteau, et al., *Cancer Research*, 67(6), 2840-2848 (2007)). A critical feature of GBMs is that tumor cells are invasive, migrating away from the main tumor body, and continuing to divide elsewhere in the brain. This is one reason why approaches to treatment that focus on a tumor mass are ultimately not successful at eliminating the disease.

A considerable number of viruses have been tested for potential oncolytic activity against glioblastoma (Parker, et al., *Neurotherapeutics*, 6:558-569 (2009)). These include human pathogenic viruses that were genetically attenuated to render them safe enough for human application, for example HSV (Todo T, *Front Biosci.*, 13:2060-2064 (2008)) and adenovirus (Nandi, et al., *Expert Opin. Biol. Ther.*, 9:737-747 (2009); Chiocca, et al., *Mol. Ther.*, 16:618-626 (2008)), and viruses based on vaccination strains, including polio (Dobrikova, et al., *Mol. Ther.*, 16:1865-1872 (2008)), measles (Phuong, et al., *Cancer Res*, 63:2462-2469 (2003)), and vaccinia (Lun, et al., *Mol. Ther.*, 18:1927-1936 (2010)), or adeno-associated viral vectors expressing various genes (Maguire, et al., *Mol. Ther.*, 16:1695-1702 (2008)). However, HSV and retroviruses can either enter a latent mode and re-emerge later, or can integrate into host chromosomes, enhancing an oncogenic potential. Furthermore, many of these viruses share the potential problem that most humans have been exposed to these viruses before and their efficacy after systemic application may be challenged by pre-existing immunity.

A promising alternative is the use of viruses that are non-human pathogens but that display a tropism for tumors, as is the case with myxoma (Lun, et al., *Cancer Res*, 65:9982-9990 (2005)), Newcastle disease virus (Freeman, et al., *Mol. Ther.*, 13:221-228 (2006), or VSV (Stojdl, et al., *Cancer Cell.*, 4:263-275 (2003)). VSV infections do not integrate (and in fact do not even enter the nucleus), and in animals, including humans, are eliminated from the body within 1-2 weeks by the systemic immune system. In regions of Central America where VSV is endemic, local human populations are seropositive for VSV, with no obvious link to substantive disease (Tesh, et al, 1969). VSV is rare in the US, indicating a very low level of pre-existing immunity. VSV has been approved for human clinical trials where VSV is used as a vaccine vector to immunize people against dangerous viral or bacterial pathogens (Roberts et al, 1999; Rose et al, 2000; Schwartz et al, 2010).

Another type of attenuated VSV, VSV-M51, shows a reduced ability to block nuclear pores, thereby allowing normal cells to up-regulate antiviral defenses, and has been described as showing an enhanced safety profile (Stojdl, et al., *Nat. Med.*, 6:821-825 (2000); Stojdl, et al., *Cancer Cell*, 4:263-275 (2003)). However, this attenuated virus can still generate lethal outcomes after CNS injection.

Some oncolytic viruses have been tested in early phase 1 clinical trials, but although the viruses were found to be safe, little therapeutic effect was seen, and then only in a subset of patients (Zemp, et al., *Cytokine Growth Factor Rev.*, 21:103-117 (2010)), underlining the importance of continuing efforts to find more effective oncolytic viruses and delivery strategies (Liu, et al., *Mol. Ther.*, 16:1006-1008 (2008)). Accordingly, despite the advances in the development and use of oncolytic viruses for treatment of cancer, there remains a need for improved virus and methods of use therefore for safely and effective treating cancers such as glioblastoma.

Therefore, it is an object of the invention to provide recombinant oncolytic viruses with improved safety and efficacy profiles.

It is a further object of the invention to provide pharmaceutical compositions including an effective amount of recombinant oncolytic viruses to treat cancer in a human subject.

It is another object of the invention to provide methods of using recombinant oncolytic virus to kill cancer cells.

It is a further object of the invention to increase the body's immune response against cancer cells.

It is a further object to generate a safer virus-based vaccine against other non-related microbial antigens.

SUMMARY OF THE INVENTION

Methods of treating cancer including administering to a subject with cancer a pharmaceutical composition including an effective amount of a chimeric VSV virus are disclosed. The chimeric viruses are based on a VSV background where the VSV G protein is replaced with one or more heterologous viral glycoproteins. In the most preferred embodiment, the VSV G protein is replaced with the glycoprotein from Lassa virus or a functional fragment thereof. The Examples below show that replacement of the VSV G protein with a heterologous glycoprotein, particularly the glycoprotein from Lassa virus, results in an oncolytic virus that is highly attenuated and safe in the brain, yet still retains sufficient oncolytic activity to infect and destroy cancer cells such as glioblastoma and intracranial melanoma metastases. The chimeric virus can be further modified to express one or more therapeutic proteins, reporters, vaccine antigens, or targeting moieties. Exemplary therapeutic proteins and reporters include, but are not limited to, IL-28, IL-2, FLT3L, GM-CSF, IL-4, IL-7, IL-12, TRAIL, carcinoembryonic antigen, secreted alkaline phosphatase, the beta subunit of chorionic gonadotropin, and green fluorescent protein.

Methods can include administering to a subject an effective amount of the virus to reduce one or more symptoms of cancer, for example tumor burden. The cancer can be multiple myeloma, bone, bladder, brain, breast, cervical, colo-rectal, esophageal, kidney, liver, lung, nasopharangeal, pancreatic, prostate, skin, stomach, and uterine. In a preferred embodiment, the methods are used to treat brain cancer and brain metastases. Brain cancers include, but are not limited to, oligodendroglioma, meningioma, supratentorial ependymona, pineal region tumors, medulloblastoma, cerebellar astrocytoma, infratentorial ependymona, brainstem glioma, schwannomas, pituitary tumors, craniopharyngioma, optic glioma, and astrocytoma. In a particularly preferred embodiment, the cancer is glioblastoma.

The virus is typically administered in a dosage of between about $10^2$ and about $10^{12}$ PFU, more preferably between about $10^2$ and about $10^{12}$ PFU. The pharmaceutical composition can be administered locally to the site of the cancer. For example, the composition can be injected into or adjacent to a tumor in the subject, or via catheter into a tumor resection cavity, for example, by convection-enhanced delivery (CED). The pharmaceutical composition can be administered systemically to the subject, for example by intravenous, intra-arterial, or intrathecal injection or infusion.

The virus can be administered in combination with one or more additional therapeutic agents. The one or more additional therapeutic agents can be, for example, an anticancer agent such as a chemotherapeutic agent, a therapeutic protein such as IL-2, or an immunosuppressant. The immunosuppressant can be a histone deacetylase (HDAC) inhibitor or an interferon blocker, for example, valproate, the vaccinia protein B18R, Jak inhibitor 1, or vorinostat, which can be used to reduce or delay the subject's immune response to the virus.

The pharmaceutical composition can be administered in combination with surgery. In some embodiments, the subject is pre-treated with an immunizing composition including a virus effective to immunize the subject to the chimeric VSV virus prior to administration of the pharmaceutical composition. The virus in the immunizing composition can be the chimeric VSV virus. Immunizing the subject against the virus can increase the ability of the subject's immune system to clear the virus following therapeutic treatment if needed.

Other methods of treating cancer are also disclosed. For example, a method of treating a subject for cancer can include (a) infecting isolated cancer cells with an effective amount of a chimeric VSV virus and (b) administrating the infected cells to the subject in an effective amount to induce an immune response against the cancer cells in the subject. In some embodiments, the method includes irradiating the cells to prevent their proliferation in the subject. The method can be used to therapeutically or prophylactically treat cancer in the subject.

Methods of priming the immune system for attacking cancer cells and adaptive T cell therapy are also disclosed. The priming can occur in vitro or in vivo. A particular embodiment of preparing cells for adaptive T cell therapy includes administering to a subject with cancer a pharmaceutical composition including an effective amount of a chimeric VSV virus to increase the number of cytotoxic T cells (CTL) which can directly kill the cancer, or to increase the number of CD4+ T and/or CD8+ T cells which can direct an immune response against the cancer. The T cells can be isolated from the subject and propagated in vitro. The T cells can be administered back to the same subject, or another subject in need thereof.

Pharmaceutical dosage units and kits including an effective amount of the disclosed chimeric viruses are also provided.

BRIEF DESCRIPTION OF THE DRAWINGS

FIG. 1A is a histogram showing percent infected cells (% GFP) for each of three gliomas tested (U87, U118 and CT2A, are represented by different shading) 24 hours after infection with 0.1 multiplicity of infection (MOI) of a VSV ((control) also referred to herein as VSV-wtG), or a chimeric VSV virus wherein the G protein was replaced with the glycoprotein from Lassa (as referred to herein as Lassa-VSV, VSV-LASV-G, and LASV), rabies (also referred to herein as VSV-RABV-G and RABV), LCMV (also referred to herein as VSV-LCMV-G), Ebola (also referred to herein as EBOV, VSV-EBOV-G, and Ebola-VSV), or Marburg (also referred to herein as MARV and VSV-MARV-G). FIG. 1B is a histogram showing the viral replication (Titer, pfu/ml) VSV-wtG (control), or a chimeric VSV virus wherein the G protein was replaced with the glycoprotein from Lassa, rabies, LCMV, Ebola, or Marburg. FIG. 1C is an illustration of the relative mean diameter and the small vertical line surmounting each the SEM, of 60 randomly selected fluorescent plaques measured and normalized to VSV-wtG plaque size on monolayers of U87, U118 and normal human brain cells, 24 hpi with VSV-wtG (control), or a chimeric VSV virus wherein the G protein was replaced with the glycoprotein from Lassa, LCMV, or Ebola. FIG. 1D is a histogram showing the fraction of infected cells of mouse brain cultures (% gila (top portion of the bar) versus % neurons (bottom portion of the bar)) for cells infected withVSV-wtG (control), or a chimeric VSV virus wherein the G protein was replaced with the glycoprotein from Lassa, rabies, LCMV, Ebola, or Marburg (MOI 5).

FIG. 2A is a Kaplan-Meier survival curve showing the % survival of mice infected with chimeric Lassa-VSV, chimeric Ebola-VSV, attenuated VSV-MA51, or attenuated VSV-1'GFP over time (in days post-inoculation) following intracranial inoculation with virus. FIG. 2B is a Kaplan-Meier survival curve showing the % survival of mice infected with chimeric Lassa-VSV or VSV-IFN over time (in days post-inoculation) following intracranial inoculation with virus.

FIG. 3A is a histogram showing infection of human neuronal cultures with VSV-wtG or chimeric Lassa-VSV (GFP expression %) with or without treatment with 100 IU/ml of interferon (IFN).

DETAILED DESCRIPTION OF THE INVENTION

I. Definitions

Figure 3B:
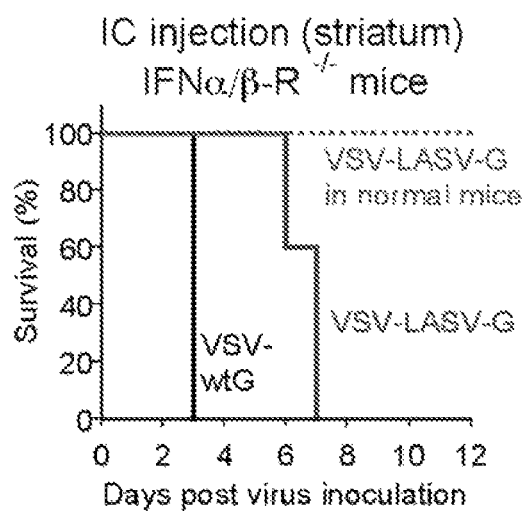
FIG. 3B is a Kaplan-Meier survival curve showing the % survival of normal mice infected with chimeric Lassa-VSV, and IFNα/β-R knockout (−/−) mice infected with VSV-wtG or Lassa-VSV (in days post-inoculation) following intracranial inoculation with virus.

As used herein, the term "isolated" describes a compound of interest (e.g., either a polynucleotide or a polypeptide) that is in an environment different from that in which the compound naturally occurs e.g., separated from its natural milieu such as by concentrating a peptide to a concentration at which it is not found in nature. "Isolated" includes compounds that are within samples that are substantially enriched for the compound of interest and/or in which the compound of interest is partially or substantially purified. With respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "nucleic acid(s)" refers to any nucleic acid containing molecule, including, but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. In accordance with standard nomenclature, nucleic acid sequences are denominated by either a three letter, or single letter code as indicated as follows: adenine (Ade, A), thymine (Thy, T), guanine (Gua, G) cytosine (Cyt, C), uracil (Ura, U).

As used herein, the term "polynucleotide" refers to a chain of nucleotides of any length, regardless of modification (e.g., methylation).

As used herein, the term "gene" refers to a nucleic acid (e.g., DNA or RNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The term "gene" encompasses both cDNA and genomic forms of a gene, which may be made of DNA, or RNA. A genomic form or clone of a gene may contain the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "nucleic acid molecule encoding," refers to the order or sequence of nucleotides along a strand of nucleotides. The order of these nucleotides determines the order of amino acids along the polypeptide (protein) chain. The nucleotide sequence thus codes for the amino acid sequence.

As used herein, the term "polypeptide" refers to a chain of amino acids of any length, regardless of modification (e.g., phosphorylation or glycosylation). In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine. (Cys, C), Glutamine (Gin, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant," "mutant," or "mutated" polynucleotide contains at least one polynucleotide sequence alteration as compared to the polynucleotide sequence of the corresponding wild-type or parent polynucleotide. Mutations may be natural, deliberate, or accidental. Mutations include substitutions, deletions, and insertions.

As used herein, a "nucleic acid sequence alteration" can be, for example, a substitution, a deletion, or an insertion of one or more nucleotides. An "amino acid sequence alteration" can be, for example, a substitution, a deletion, or an insertion of one or more amino acids.

As used herein, the term "immunizing virus" includes infectious virus, viral subunits, viral proteins and antigenic fragments thereof, nucleic acids encoding viral subunits, antigenic proteins or polypeptides, and expression vectors containing the nucleic acids.

As used herein, a "vector" is a replicon, such as a plasmid, phage, or cosmid, into which another DNA segment may be inserted so as to bring about the replication of the inserted segment. The vectors described herein can be expression vectors.

As used herein, the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being effected.

As used herein, the terms "neoplastic cells," "neoplasia," "tumor," "tumor cells," "cancer" and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

As used herein, an "immunogen" or "immunogenic amount" refers to the ability of a substance (antigen) to induce an immune response. An immune response is an alteration in the reactivity of an organisms' immune system in response to an antigen. In vertebrates this may involve antibody production, induction of cell-mediated immunity, complement activation or development of immunological tolerance.

As used herein, an "adjuvant" is a substance that increases the ability of an antigen to stimulate the immune system.

As used herein, "attenuated" refers to refers to procedures that weaken an agent of disease (a pathogen). An attenuated virus is a weakened, less vigorous virus. A vaccine against a viral disease can be made from an attenuated, less virulent strain of the virus, a virus capable of stimulating an immune response and creating immunity but not causing illness or less severe illness. Attenuation can be achieved by chemical treatment of the pathogen, through radiation, or by genetic modification, using methods known to those skilled in the art. Attenuation may result in decreased proliferation, attachment to host cells, or decreased production or strength of toxins.

As used herein, "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. A subject can include a control subject or a test subject.

As used herein, "identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up, to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "treatment" or "treating" means to administer a composition to a subject or a system with an undesired condition. The condition can include a disease. "Prevention" or "preventing" means to administer a composition to a subject or a system at risk for the condition. The condition can include a predisposition to a disease. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur. It is understood that where treat or prevent are used, unless specifically indicated otherwise, the use of the other word is also expressly disclosed.

II. Compositions

VSV, a member of the Rhabdoviridae family, is enveloped and has a negative-strand 11.2-kb RNA genome that comprises five protein-encoding genes (N, P, M, G, and L) (Lyles, et al., Fields virology, 5$^{th}$ ed., *Lippincott Williams & Wilkins*, 1363-1408 (2007)). It is a nonhuman pathogen which can cause mild disease in livestock. Infection in humans is rare and usually asymptomatic, with sporadic cases of mild flu-like symptoms. VSV has a short replication cycle, which starts with attachment of the viral glycoprotein spikes (G) to an unknown but ubiquitous cell membrane receptor. Nonspecific electrostatic interactions have also been proposed to facilitate viral binding (Lyles, et al., Fields virology, 5$^{th}$ ed., *Lippincott Williams & Wilkins*, 1363-1408 (2007)). Upon internalization by clathrin-dependent endocytosis, the virus-containing endosome acidifies, triggering fusion of the viral membrane with the endosomal membrane. This leads to release of the viral nucleocapsid (N) and viral RNA polymerase complex (P and L) into the cytosol.

The viral polymerase initiates gene transcription at the 3' end of the non-segmented genome, starting with expression of the first VSV gene (N). This is followed by sequential gene transcription, creating a gradient, with upstream genes expressed more strongly than downstream genes. Newly produced VSV glycoproteins are incorporated into the cellular membrane with a large extracellular domain, a 20 amino acid trans-membrane domain, and a cytoplasmic tail consisting of 29 amino acids. Trimers of G protein accumulate in plasma membrane microdomains, several of which congregate to form viral budding sites at the membrane (Lyles, et al., Fields virology, 5$^{th}$ ed., *Lippincott Williams & Wilkins*, 1363-1408 (2007)). Most cells activate antiviral defense cascades upon viral entry, transcription, and replication, which in turn are counteracted by VSV matrix protein (M). VSV M protein's multitude of functions include virus assembly by linking the nucleocapsid with the envelope membrane, induction of cytopathic effects and apoptosis, inhibition of cellular gene transcription, and blocking of host cell nucleocytoplasmic RNA transfer, which includes blocking of antiviral cellular responses (Ahmed, et al., *Virology*, 237:378-388 (1997)).

Certain native, engineered, and recombinant VSV strains have been shown to target several tumor types, including gliomas, and give a strong oncolytic action, both in vitro and in vivo (Paglino and van den Pol, 2011) (Wollmann, et al, 2005; 2007; 2010; Ozduman et al, 2008). However, there remains a need for improved recombinant VSVs that are both efficacious for treating cancer and exhibit low pathogenicity to healthy host cells. This is particularly important in the brain where mature neurons do not replicate, and once lost, are normally not replaced. Although some evidence indicates that attenuated VSVs show reduced neurotoxicity, CNS complications have been difficult to eliminate completely (Obuchi et al, 2003; van den Pol et al, 2002; 2009).

It has been discovered that recombinant, chimeric VSV viruses where the G gene is substituted with a gene encoding a heterologous glycoprotein protein have oncolytic potential in targeting and destroying cancer cells with little pathogenicity to healthy host cells. Recombinant VSV viruses, pharmaceutical compositions including recombinant VSV viruses, and methods of use thereof for treating cancer are provided. As discussed in more detail below, preferably, the virus targets and kills tumor cells, and shows little or no infection of normal cells.

A. Chimeric G-Gene Substituted VSV Virus

The disclosed viruses are chimeric VSV viruses that are typically based on a VSV background strain, also referred to herein as a VSV backbone, wherein the G gene is substituted for a heterologous glycoprotein. As discussed in more detail below, the chimeric virus can also include additional genetic changes (e.g., additions, deletions, substitutions) relative to the background VSV virus, and can have one or more additional transgenes.

1. VSV Background Strain

Useful VSV virus background strains can be viruses that are known in the art, or they can be mutants or variants of known viruses. Any suitable VSV strain or serotype may be used, including, but not limited to, VSV Indiana, VSV New Jersey, VSV Alagoas, (formerly Indiana 3), VSV Cocal (formerly Indiana 2), VSV Chandipura, VSV Isfahan, VSV San Juan, VSV Orsay, or VSV Glasgow. The VSV virus background can be a naturally occurring virus, or a virus modified, for example, to increase or decrease the virulence of the virus, and/or increase the specificity or infectivity of the virus compared to the parental strain or serotype. The virus can be a recombinant virus that includes genes from two or more strains or serotypes. For example, the VSV background strain can be a recombinant VSV with all five genes of the Indiana serotype of VSV. In another exemplary embodiments, the N, P, M, and L genes originates from the San Juan strain, and the G gene from the Orsay strain.

It may be desirable to further reduce the neurovirulence of the viruses used in the disclosed methods, particularly the virulence of the therapeutic virus, by using an attenuated virus. A number of suitable VSV mutants have been described, see for example (Clarke, et al., *J. Virol.*, 81:2056-64 (2007), Flanagan, et al., *J. Virol.*, 77:5740-5748 (2003), Johnson, et al., *Virology*, 360:36-49 (2007), Simon, et al., *J. Virol.*, 81:2078-82 (2007), Stojdl, et al., *Cancer Cell*, 4:263-275 (2003)), Wollmann, et al., *J. Virol*, 84(3):1563-73 (2010) (epub 2010), WO 2010/080909, U.S. Published Application No. 2007/0218078, and U.S. Published Application No 2009/0175906.

Recombinant VSVs derived from DNA plasmids also typically show weakened virulence (Rose, et al., *Cell*, 106: 539-549 (2001)). Attenuation of VSV virulence can also be accomplished by one or more nucleotide sequence alterations that result in substitution, deletion, or insertion of one or more amino acids of the polypeptide it encodes.

In some embodiments, the VSV background strain is a VSV virus modified to attenuate virus growth or pathogenicity or to reduce the ability to make infectious progeny viruses. VSV strains and methods of making such VSV strains are known in the art, and described in, for example, U.S. Published Application No. 2012/0171246.

For example, one strategy is to attenuate viral pathogenicity by reducing the ability of the virus to suppress host innate immune responses without compromising the yield of infectious progeny. This can be accomplished by mutating the M protein as described, for example, in Ahmed, *J. Virol.*, 82(18):9273-9277 (2008). The M protein is a multifunctional protein that is involved in the shutoff of host transcription, nuclear cytoplasmic transport, and translation during virus infection (Lyles, *Microbial. Mol. Biol. Rev.* 64:709-724 (2000)). Mutation and/or deletion of one or more amino acids from the M protein, for example MΔ51, or M51A mutants can result in viral protein that is defective at inhibiting host gene expression. It may also be desirable to switch or combine various substitutions, deletions, and insertions to further modify the phenotype of the virus. For example, the recombinant VSV background can have a deletion or mutation in the M protein.

Altering the relative position of genes can also be used to attenuate virus (Clarke, et al., *J. Virol.*, 81:2056-2064, (2007), Cooper, et al., *J. Virol.*, 82:207-219 (2008), Flanagan, et al., *J. Virol.*, 75:6107-6114 (2001)). VSV is highly immunogenic, and a substantial B and T cell response from the adaptive immune system will ultimately limit VSV infection, which will halt long-lasting viral infections. A virus that shows enhanced selectivity, and a faster rate of infection, will have a greater likelihood of eliminating cancer cells before the virus is eliminated by the immune system. However, the use of VSV against cancer cells does not have to be restricted to a single application. By molecular substitution of the G-protein for enhancing immune responses against foreign genes expressed by VSV, one could switch the original G protein of the virus (e.g., Indiana VSV) with the G protein from another strain or serotype (e.g., VSV New Jersey or Chandipura), allowing a slightly different antigen presentation, and reducing the initial response of the adaptive immune system to second or third oncolytic inoculations with VSV.

Therefore, the disclosed chimeric viruses can have a VSV genome that is rearranged compared to wildtype VSV. For example, shifting the L-gene to the sixth position, by rearrangement or insertion of an additional gene upstream, can result in attenuated L-protein synthesis and a slight reduction in replication (Dalton and Rose, *Virology*, 279(2):414-21 (2001)), an advantage when considering treatment of the brain.

Repeat passaging of virulent strains under evolutionary pressure can also be used to generate attenuated virus, increase specificity of the virus for a particular target cell type, and/or increase the oncolytic potential of the virus. For example, VSV-rp30 ("30 times repeated passaging") is a wild-type-based VSV with an enhanced oncolytic profile (Wollmann, et al., *J. Virol.* 79:6005-6022 (2005)). As described in WO 2010/080909, VSV-rp30 has a preference for glioblastoma over control cells and an increased cytolytic activity on brain tumor cells. Accordingly, in some embodiments, the VSV background of the disclosed chimeric viruses is one that has been modified to attenuate the virus, increase specificity of the virus for a particular target cells, and/or increase the oncolytic potential of the virus relative to a wildtype or starting stain.

2. Heterologous Glycoproteins

The disclosed chimeric VSV viruses have a heterologous glycoprotein. Typically, the disclosed chimeric VSV viruses are viruses that lack the G protein of VSV. Instead the chimeric VSV viruses have a glycoprotein (e.g., G protein or GP protein) from a distinct, non-VSV virus.

As demonstrated in the Examples below, glycoproteins for a number of different viruses can be substituted into a VSV background to create a chimeric VSV that can infect cancer cells. Suitable glycoproteins can be from, for example, Lassa, rabies, lymphocytic choriomeningitis virus (LCMV), Ebola, or Marburg virus. The Examples below show that an Ebola-VSV, and even more so a Lassa-VSV chimera, are particularly effective at killing brain cancers with little or no toxicity to healthy or normal cells. Other viral glycoprotein such as those from rabies, lymphocytic choriomeningitis virus (LCMV), or Marburg virus may be more suitable for targeting other cancer types, such as one or more of the cancers discussed in more detail below. It is believed that VSV chimeric viruses including an LCMV glycoprotein in place of the VSV glycoprotein may show some advantages over the VSV glycoprotein in infecting some cancer or sarcoma cells with enhanced innate immunity, such as the virus-resistant sarcoma cells described in Paglino and van den Pol, *J. Virol.*, 85:9346-9358 (2011). In some embodiments, the G protein in the VSV chimeric virus is a heterologous G, wherein the G protein is not a G protein from LCMV.

In place of the Lassa glycoprotein which has a broad spectrum of cells to which it binds, the VSV chimeric virus can have a glycoprotein from another arena virus. Other arenaviruses may have the same, similar, or different cellular binding receptors to Lassa. In some embodiments, the glycoprotein is a viral glycoprotein, preferably an arenavirus glycoprotein, that binds to one or more of the same cell receptors as Lassa glycoprotein. In some embodiments, the glycoprotein is a viral glycoprotein, preferably an arenavirus glycoprotein that binds to one or more similar cell receptors as Lassa glycoprotein. In some embodiments, the glycoprotein is an areanvirus glycoprotein that binds to different cell receptor(s) than Lassa glycoprotein. Such chimeric viruses may also be safe viruses for use in oncolysis or as vaccine vectors. Exemplary arenaviruses include, but are not limited to, Old World complex arenaviruses such as Kodoko, Lujo, Mobala, Dank, Gbagroube, Ippy, Merino Walk, Menekre, Mobala, and Mopeia, and New World arenaviruses such as Guanarito, Junin, Machupo, Sabia, Whitewater arroyo, Parana, Tamiami, Latino, plexal, and Chapare. New World arenavirus glycoproteins may target receptors different that those targeted by the Lassa glycoprotein.

a. Lassa G Proteins

In the most preferred embodiment, the G protein of VSV is substituted with a glycoprotein from a Lassa virus. Lassa virus is an *Arenavirus*. The genomic structure or *Arenaviruses* and the genetic diversity of Lassa virus strains are discussed in Bowen, et al., *J. Virology*, 6992-7004 (2000). Viruses of the genus *Arenavirus*, family Arenaviridae, are enveloped viruses with a genome consisting of two single stranded RNA species designated small (S) and large (L). Each segment contains two non-overlapping genes arranged in an arnbisense orientation. The viral polymerase (L protein) gene is encoded at the 3' end of the L RNA in the genome-complementary sense, whereas the Z protein is encoded at the 5' end of the L RNA in the genomic sense. In a similar fashion, the nucleoprotein (NP) gene is encoded at the 3' end of the S RNA, whereas the glycoprotein precursor (GPC) is encoded at the 5' end of the S RNA. The GPC is post-translationally cleaved into the envelope glycoproteins GP1 and GP2. The arenaviruses have been divided into two groups, the New World arenaviruses and the Old World arenaviruses. Lassa virus is an Old World arenavirus.

The glycoprotein can come from any Lassa virus. The Lassa virus glycoprotein can be from a naturally occurring virus, or a virus modified, for example, to increase or decrease the virulence of the virus, and/or increase the specificity or infectivity of the virus compared to the parental strain or serotype. Suitable strains and serotypes of Lassa virus from which the glycoprotein of the chimeric VSV virus can be derived are known in the art and include, for example, fifty-four strains identified and characterized in Bowen, et al., *J. Virology*, 6992-7004 (2000). Common Lassa virus stains include Lassa virus strain 803213, Lassa virus strain Acar 3080, Lassa virus strain AV, Lassa virus strain Josiah, Lassa virus strain LP, Lassa virus strain Macenta, Lassa virus strain NL, Lassa virus strain Pinneo, Lassa virus strain Weller, and Lassa virus strain Z148.

Preferably, the chimeric virus's genome, or plasmid(s) encoding the virus's genome encode the entire Lassa virus glycoprotein precursor (GPC), such that both GP1 and GP2 are expressed and contribute to formation of the chimeric virus's envelope. In some embodiments, the chimeric virus's genome, or plasmid(s) encoding the virus's genome encode less than the entire Lassa virus glycoprotein precursor (GPC). For example, in some embodiments, the viral genome or plasmid(s) encoding recombinant viral genome encodes a glycoprotein that is a truncated GPC, or only GP1 or only GP2.

The glycoprotein can be from Lassa strain Josiah. In a particular embodiment, the chimeric viral genome includes the nucleic acid sequence

```
  1 cgcaccgggg atcctaggca tttttggttg cgcaattcaa gtgtcctatt taaaatggga 61 caaatagtga cattcttcca ggaagtgcct catgtaatag aagaggtgat gaacattgtt 121 ctcattgcac tgtctgtact agcagtgctg aaaggtctgt acaattttgc aacgtgtggc 181 cttgttggtt tggtcacttt cctcctgttg tgtggtaggt cttgcacaac cagtctttat 241 aaagggttt atgagcttca gactctggaa ctaaacatgg agacactcaa tatgaccatg 301 cctctctcct gcacaaagaa caacagtcat cattatataa tggtgggcaa tgagacagga
```

```
 361 ctagaactga ccttgaccaa cacgagcatt attaatcaca
     aattttgcaa tctgtctgat
 421 gcccacaaaa agaacctcta tgaccacgct cttatgagca
     taatctcaac tttccacttg
 481 tccatcccca acttcaatca gtatgaggca atgagctgcg
     attttaatgg gggaaagatt
 541 agtgtgcagt acaacctgag tcacagctat gctggggatg
     cagccaacca ttgtggtact
 601 gttgcaaatg gtgtgttaca gacttttatg aggatggctt
     ggggtgggag ctacattgct
 661 cttgactcag gccgtggcaa ctgggactgt attatgacta
     gttatcaata tctgataatc
 721 caaaatacaa cctgggaaga tcactgccaa ttctcgagac
     catctcccat cggttatctc
 781 gggctcctct cacaaaggac tagagatatt tatattagta
     gaagattgct aggcacattc
 841 acatggacac tgtcagattc tgaaggtaaa gacacaccag
     ggggatattg tctgaccagg
 901 tggatgctaa ttgaggctga actaaaatgc ttcgggaaca
     cagctgtggc aaaatgtaat
 961 gagaagcatg atgaggaatt ttgtgacatg ctgaggctgt
     ttgacttcaa caaacaagcc
1021 attcaaaggt tgaaagctga agcacaaatg agcattcagt
     tgatcaacaa agcagtaaat
1081 gctttgataa atgaccaact tataatgaag aaccatctac
     gggacatcat gggaattcca
1141 tactgtaatt acagcaagta ttggtacctc aaccacacaa
     ctactgggag aacatcactg
1201 cccaaatgtt ggcttgtatc aaatggttca tacttgaacg
     agacccactt ttctgatgat
1261 attgaacaac aagctgacaa tatgatcact gagatgttac
     agaaggagta tatggagagg
1321 caggggaaga caccattggg tctagttgac ctctttgtgt
     tcagtacaag tttctatctt
1381 attagcatct tccttcacct agtcaaaata ccaactcata
     ggcatattgt aggcaagtcg
1441 tgtcccaaac ctcacagatt gaatcatatg ggcatttgtt
     cctgtggact ctacaaacag
1501 cctggtgtgc ctgtgaaatg gaagagatga gacccttgtc
     agggcccccg tgacccaccg
1561 cctattggcg gtgggtcacg ggggcgtcca tttacagaac
     gactctaggt gtcgatgttc
1621 tgaacaccat atctctgggc agcactgctc tcaaaaccga
     tgtgttcagt cctcctgaca
1681 ctgctgcatc aaacatgatg cagtccatta gtgcacagtg
     aggggttatt tcctctttac
1741 cgcctctttt cttcttttca acaacgacac ctgtgtgcat
     gtggcataag tctttatact
1801 ggtcccagac tgcattttca tacttcctgg aatcagtttt
     gctgagggca atatcaatta
1861 gtttaatgtc ttttcttcct tgtgattcaa ggagtttcct
     tatgtcatcg gaccCctgac
1921 aggtaatgac catattccgg gggagtgcat caatgacagc
     actggtcaag cccggttgtg
1991 tagcgaaagg gtctgtgaca tcaatcccat gtgagtactt
     agcatcctgc ttgaactgct
2041 ttaaatcagt aggttcacgg aagaagtgta tgtagcagcc
     tgaacttggt tgatagaggg
2101 caatttccac tggatcttca ggtcttcctt caatgtccat
     ccaggtctta gcatttgggt
2161 caagttgcag cattgcatcc ttgagggtca tcagctgaga
     ataggtaagc ccagcggtaa
2221 accctgccga ctgcagggat ttactggaat tgttgctgtc
     agctttctgt ggcttcccat
2281 ctgattccag atcaacgaca gtgttttccc aggcccttcc
     tgttattgag gttcttgatg
2341 caatatatgg ccatccatct cctgacaaac aaatcttgta
     gagtatgttt tcataaggat
2401 tccttccacc aggggtgtct gaaatgaaca ttccaagagc
     cttcttgacc tttaaaatgg
2461 atttgaggat accatccatt gtctgaggtg acaccttgat
     tgtctccaac atattgccac
2521 catccagcat gcaagctcct gccttcacag ctgcacccaa
     gctaaaatta taacctgaga
2581 tattcaaaga gctttcttg gtgtcaatca tatttaggat
     gggatgactt tgagtcagcc
2641 tgtctaagtc tgaagtgttg ggatactttg ctgtgtagat
     caaacccaaa tctgtcaatg
2701 cttgtactgc atcattcaag tcaacctgcc cctgttttgt
     cagacatgcc agtgtcagac
```

```
2761  ttggcatggt cccgaactga ttattgagca actctgcatt
      tttcacatcc caaactctca
2821  ccactccatc tctcccagcc cgagcccctt gattaccacc
      actcattcct atcatattca
2881  ggagagctct tctttggtca agttgctgtg agcttaggtt
      gcccatatag acacctgcac
2941  ttaatggcct ttctgttctg atcacctttg actttaactt
      ctctagatca gcggctaaga
3001  ttaataagtc atctgaggtt agagtcccaa ctctcagtat
      actcttttgt tgagttgatt
3061  ttaattcaac aagattgttg accgcttgat ttaggtccct
      caaccgtttc aaatcattgt
3121  catcccttct ctccttgcgc atcaaccgtt gaacattact
      gacttcggag aagtcaagtc
3161  catgtaaaag agcctgggca tctttcacca cctgtagttt
      gatgttggag cagtaaccag
3241  ataattccct cctcaaagat tgtgtccaca aaaaggattt
      tatttccttt gaggcactca
3301  tcgccagatt gttgtgttgt atgcacgcaa caaagaactg
      agactatctg ccaaaatgac
3361  aaaagcaaag cgcaatccaa tagcctagga tccactgtgc
      g
```

(SEQ ID NO: 1, Lassa virus strain recombinant Josiah segment S, complete sequence GenBank: HQ688673.1), one or both of the open reading frames thereof, or a fragment or fragments or variants thereof encoding a functional glycoprotein. Variants can have at least 70%, 80%, 85%, 90%, 95%, 96%, 97%, 98%, 99%, or more sequence identity to SEQ ID NO:1, or to the sequence encoding an open reading frame thereof.

In some embodiments, the chimeric viral genome includes a nucleic acid sequence encoding the polypeptide

MGQIVTFFQEVPHVIEEVMNIVLIALSVLAVLKGLYNFATCGLVGLVTFL

LLCGRSCTTSLYKGVYELQTLELNMETLNMTMPLSCTKNNSHHYIMVGNE

TGLELTLTNTSIINHKFCNLSDAHKKNLYDHALMSIISTFHLSIPNFNQY

EAMSCDFNGGKISVQYNLSHSYAGDAANHCGTVANGVLQTFMRMAWGGSY

IALDSGRGNWDCIMTSYQYLIIQNTTWEDHCQFSRPSPIGYLGLLSQRTR

DIYISRRLLGTFTWTLSDSEGKDTPGGYCLTRWMLIEAELKCFGNTAVAK

CNEKHDEEFCDMLRLFDFNKQAIQRLKAEAQMSIQLINKAVNALINDQLI

MKNHLRDIMGIPYCNYSKYWYLNHTTTGRTSLPKCWLVSNGSYLNETHFS

DDIEQQADNMITEMLQKEYMERQGKTPLGLVDLFVFSTSFYLISIFLHLV

KIPTHRHIVGKSCPKPHRLNHMGICSCGLYKQPGVPVKWKR (SEQ ID

NO: 2, GenBank: HQ688673.1), the polypeptide

MSASKEIKSFLWTQSLRRELSGYCSNIKLQVVKDAQALLHGLDFSEVSNV

QRLMRKERRDDNDLKRLRDLNQAVNNLVELKSTQQKSILRVGTLTSDDLL

ILAADLEKLKSKVIRTERPLSAGVYMGNLSSQQLDQRRALLNMIGMSGGN

QGARAGRDGVVRVWDVKNAELLNNQFGTMPSLTLACLTKQGQVDLNDAVQ

ALTDLGLIYTAKYPNTSDLDRLTQSHPILNMIDTKKSSLNISGYNFSLGA

AVKAGACMLDGGNMLETIKVSPQTMDGILKSILKVKKALGMFISDTPGER

NPYENILYKICLSGDGWPYIASRTSITGRAWENTVVDLESDGKPQKADSN

NSSKSLQSAGFTAGLTYSQLMTLKDAMLQLDPNAKTWMDIEGRPEDPVEI

ALYQPSSGCYIHFFREPTDLKQFKQDAKYSHGIDVTDLFATQPGLTSAVI

DALPRNMVITCQGSDDIRKLLESQGRKDIKLIDIALSKTDSRKYENAVWD

QYKDLCHMHTGVVVEKKKRGGKEEITPHCALMDCIMFDAAVSGGLNTSVL

RAVLPRDMVFRTSTPRVVL (SEQ ID NO: 3, GenBank:

HQ688673.1), a combination thereof, or a one or more functional fragments or variants thereof. Variants can have at least 70%, 80%, 85%, 90%, 95%, 96%, 97%, 98%, 99%, or more sequence identity to SEQ ID NO:2 or 3.

b. Ebola G Proteins

In another preferred embodiment, the G protein of VSV is substituted with a glycoprotein from an Ebola virus. Ebola virus, along with Marburg virus, constitutes the family Filoviridae in the order of Mononegavirales (reviewed in Feldmann and Geisbert, *Lancet,* 377(9768): 849-862 (2011), and Sanchez, et al., *Filoviridae: Marburg and Ebola viruses.* In: Knipe, D M.; Howley, P M., editors. *Fields virology.* Philadelphia: Lippincott Williams & Wilkins; 2006. p. 1409-1448). Filoviruses are enveloped, non-segmented, negative-stranded RNA viruses with filamentous particles. Ebola virus particles have a uniform diameter of 80 nm but can greatly vary in length, with lengths up to 14000 nm. The genome includes seven genes in the order 3' leader, nucleoprotein, virion protein (VP) 35, VP40, glycoprotein, VP30, VP24, RNA-dependent RNA polymerase (L)-5' trailer. With the exception of the glycoprotein gene, all genes are monocistronic, encoding for one structural protein. The inner ribonucleoprotein complex of virion particles consists of the RNA genome encapsulated by the nucleoprotein, which associates with VP35, VP30, and RNA-dependent RNA polymerase to form the functional transcriptase-replicase complex. Additionally, the proteins of the ribonucleoprotein complex have other functions, for example, VP35 is an antagonist of interferon; VP40 is a matrix protein and modulates particle formation; VP24, is structural, membrane-associated protein that also interferes with interferon signaling.

The glycoprotein is the only transmembrane surface protein of the virus and forms trimeric spikes consisting of glycoprotein 1 and glycoprotein 2—two di-sulphide linked furin-cleavage fragments (Sanchez, et al., *Filoviridae: Marburg and Ebola viruses.* In: Knipe, D M.; Howley, P M., editors. *Fields virology.* Philadelphia: Lippincott Williams & Wilkins; 2006. p. 1409-1448). The primary product of the GP gene is a soluble glycoprotein (sGP) that is also secreted from infected cells, a characteristic distinguishing it from other Mononegavirales (Sanchez, et al., *Proc Natl Acad Sci USA*, 93:3602-3607 (1996), Volchkov, et al., *Virology,* 214: 421-430 (1995)). Nucleic acid sequences encoding Ebola glycoprotein, the mechanism of transcription/translation yielding functional Ebola glycoprotein, Ebola glycoprotein amino acid sequences, and the structure and function of Ebola glycoprotein are well known in the art and discussed in, for example, Lee and Saphire, *Future Virology,* 4(6):621-635 (2009), Sanchez, *Proc Natl Acad Sci USA.,* 93(8):3602-3607 (1996), Volchkov, et al., *Virology,* 214(2):421-430 (1995), Gire et al, *Science,* 345: 1369-1372 (2014)).

The Ebola virus glycoprotein can be from a naturally occurring virus, or a virus modified, for example, to increase or decrease the virulence of the virus, and/or increase the specificity or infectivity of the virus compared to the parental strain or serotype. Suitable species of Ebola virus from which the glycoprotein of the chimeric VSV virus can be derived are known in the art and include, for example, *Sudan ebolavirus* (SEBOV), *Zaire ebolavirus* (ZEBOV), *Cote d'Ivoire ebolavirus* (also known and here referred to as *Ivory Coast ebolavirus* (ICEBOV)), *Reston ebolavirus* (REBOV), and *Bundigbugyo ebolavirus* (BEBOV) (Geibert and Feldmann, *J. Infect. Dis.,* 204 (suppl 3): S1075-S1081 (2011)). Preferably, the chimeric virus's genome, or plasmid(s) encoding the virus's genome encode the entire Ebola virus glycoprotein (GP), such that the glycoprotein is expressed and contributes to formation of the chimeric virus's envelope. In some embodiments, the chimeric virus's genome, or plasmid(s) encoding the virus's genome encode less than the entire Ebola virus glycoprotein. For example, in some embodiments, the viral genome or plasmid(s) encoding recombinant viral genome encodes a glycoprotein that is a truncated or variant GP. In some embodiments, the chimeric virus's genome, or plasmid(s) encoding the virus's genome encode full length, truncated, or variant GP1, GP2, or a combination thereof.

In some embodiment, the chimeric viral genome includes the nucleic acid sequence

```
                                            (SEQ ID NO: 6)
   1  atgggcgtta caggaatatt gcagttacct cgtgatcgat tcaagaggac atcattcttt 61  ctttgggtaa ttatcttttt ccaaagaaca ttttccatcc cacttggagt catccacaat 121  agcacattac aggttagtga tgtcgacaaa ctagtttgtc gtgacaaact gtcatccaca 181  aatcaattga gatcagttgg actgaatctc gaagggaatg gagtggcaac tgacgtgcca 241  tctgcaacta aaagatgggg cttcaggtcc ggtgtcccac caaaggtggt caattatgaa 301  gctggtgaat gggctgaaaa ctgctacaat cttgaaatca aaaaacctga cgggagtgag 361  tgtctaccag cagcgccaga cgggattcgg ggcttccccc ggtgccggta tgtgcacaaa 421  gtatcaggaa cgggaccgtg tgccggagac tttgccttcc ataaagaggg tgctttcttc 481  ctgtatgatc gacttgcttc cacagttatc taccgaggaa cgactttcgc tgaaggtgtc 541  gttgcatttc tgatactgcc ccaagctaag aaggacttct tcagctcaca ccccttgaga 601  gagccggtca atgcaacgga ggacccgtct agtggctact attctaccac aattagatat 661  caggctaccg gttttggaac caatgagaca gagtacttgt tcgaggttga caatttgacc 721  tacgtccaac ttgaatcaag attcacacca cagtttctgc tccagctgaa tgagacaata 781  tatacaagtg ggaaaagyag caataccacg ggaaaactaa tttggaaggt caaccccgaa 841  attgatacaa caatcgggga gtgggccttc tgggaaacta aaaaaaacct cactagaaaa 901  attcgcagtg aagagttgtc tttcacagtt gtatcaaacg gagccaaaaa catcagtggt 961  cagagtccgg cgcgaacttc ttccgaccca gggaccaaca caacaactga agaccacaaa 1021  atcatggctt cagaaaattc ctctgcaatg gttcaagtgc acagtcaagg aagggaagct 1081  gcagtgtcgc atctaacaac ccttgccaca atctccacga gtccccaatc cctcacaacc 1141  aaaccaggtc cggacaacag cacccataat acacccgtgt ataaacttga catctctgag 1201  gcaactcaag ttgaacaaca tcaccgcaga acagacaacg acagcacagc ctccgacact 1261  ccctctgcca cgaccgcagc cggacccca aaagcagaga acaccaacac gagcaagagc 1321  actgacttcc tggaccccgc caccacaaca agtcccaaa accacagcga gaccgctggc 1381  aacaacaaca ctcatcacca agataccgga gaagagagtg ccagcagcgg gaagctaggc 1441  ttaattacca atactattgc tggagtcgca ggactgatca caggcgggag aagaactcga 1501  agagaagcaa ttgtcaatgc tcaacccaaa tgcaacccta atttacatta ctggactact 1561  caggatgaag gtgctgcaat cggactggcc tggataccat atttcgggcc agcagccgag
```

-continued

```
1621 ggaatttaca tagaggggct aatgcacaat caagatggtt
     taatctgtgg gttgagacag
1681 ctggccaacg agacgactca agctcttcaa ctgttcctga
     gagccacaac tgagctacgc
1741 accttttcaa tcctcaaccg taaggcaatt gatttcttgc
     tgcagcgatg ggcggcaca
1801 tgccacattc tgggaccgga ctgctgtatc gaaccacatg
     attggaccaa gaacataaca
1861 gacaaaattg atcagattat tcatgatttt gttgataaaa
     cccttccgga ccagggggac
1921 aatgacaatt ggtggacagg atggagacaa tggataccgg
     caggtattgg agttacaggc
1981 gttataattg cagttatcgc tttattctgt atatgcaaat
     ttgtctttta g.
```

SEQ ID NO:6 a nucleic acid encoding a full-length (non-secreted) glycoprotein gene found in GenBank accession NC_002549 nt 6039-8068. Note that the GenBank sequence over this region is 2030 nt long, whereas SEQ ID NO:6 is 2031 nt in length. This difference derives from the fact that the GenBank sequence is based on the genomic RNA sequence, whereas the sequence below is based on the mRNA sequence that has been 'edited' by the viral polymerase to include an extra 'A' nucleotide between 6918-6924 of the GenBank sequence. Therefore, in some embodiments, the chimeric viral genome includes a nucleic acid encoding SEQ ID NO:6, or the variant thereof encoded by GenBank accession NC_002549 nt 6039-8068, or a fragment or variant thereof encoding a functional glycoprotein. Variants can have at least 70%, 80%, 85%, 90%, 95%, 96%, 97%, 98%, 99%, or more sequence identity to SEQ ID NO:6, or to the sequence encoding an open reading frame thereof.

In some embodiments, the chimeric viral genome includes a nucleic acid sequence encoding the polypeptide

```
                                        (SEQ ID NO: 7)
MGVTGILQLPRDRFKRTSFFLWVIILFQRTFSIPLGVIHNSTLQVSDVDK
LVCRDKLSSTNQLRSVGLNLEGNGVATDVPSATKRWGFRSGVPPKVVNYE
AGEWAENCYNLEIKKPDGSECLPAAPDGIRGFPRCRYVHKVSGTGPCAGD
FAFHKEGAFFLYDRLASTVIYRGTTFAEGVVAFLILPQAKKDFFSSHPLR
EPVNATEDPSSGYYSTTIRYQATGFGTNETEYLFEVDNLTYVQLESRFTP
QFLLQLNETIYTSGKRSNTTGKLIWKVNPEIDTTIGEWAFWETKKNLTRK
IRSEELSFTVVSNGAKNISGQSPARTSSDPGTNTTTEDHKIMASENSSAM
VQVHSQGREAAVSHLTTLATISTSPQSLTTKPGPDNSTHNTPVYKLDISE
ATQVEQHHRRTDNDSTASDTPSATTAAGPPKAENTNTSKSTDFLDPATTT
SPQNHSETAGNNNTHHQDTGEESASSGKLGLITNTIAGVAGLITGGRRTR
REATVNAQPKCNPNLHYWTTQDEGAAIGLAWIPYFGPAAEGIYIEGLMHN
QDGLICGLRQLANETTQALQLFLRATTELRTFSILNRKAIDFLLQRWGGT
```

-continued

```
CHILGPDCCIEPHDWTKNITDKIDQIIHDFVDKTLPDQGDNDNWWTGWRQ
WIPAGIGVTGVIIAVIALFCICKFVF,
``` or a functional fragment or variant thereof. Variants can have at least 70%, 80%, 85%, 90%, 95%, 96%, 97%, 98%, 99%, or more sequence identity to SEQ ID NO:7.

In some embodiments, the chimeric viral genome includes the nucleic acid sequence

```
                                        (SEQ ID NO: 8)
  1 atgggcgtta caggaatatt gcagttacct cgtgatcgat
    tcaagaggac atcattcttt
 61 ctttgggtaa ttatcctttt ccaaagaaca ttttccatcc
    cacttggagt catccacagt
121 agcacattac aggttagtga tgtcgacaaa ctagtttgtc
    gtgacaaact gtcatccaca
181 aatcaattga gatcagttgg actgaatctc gaagggaatg
    gagtggcaac tgacgtgcca
241 tctgcaacta aaagatgggg cttcaggtcc ggtgtcccac
    caaaggtggt caattatgaa
301 gctggtgaat gggctgaaaa ctgctacaat cttgaaatca
    aaaaacctga cgggagtgag
361 tgtctaccag cagcgccaga cgggattcgg ggcttccccc
    ggtgccggta tgtgcacaaa
421 gtatcaggaa cgggaccgtg tgccggagac tttgccttcc
    ataaagaggg tgctttcttc
481 ctgtatgatc gacttgcttc cacagttatc taccgaggaa
    cgactttcgc tgaaggtgtc
541 gttgcatttc tgatactgcc ccaagctaag aaggacttct
    tcagctcaca cccccttgaga
601 gagccggtca atgcaacgga ggacccgtct agtggctact
    attctaccac aattagatat
661 caggctaccg gttttggaac caatgagaca gagtacttgt
    tcgaggttga caatttgacc
721 tacgtccaac ttgaatcaag attcacacca cagtttctgc
    tccagctgaa tgagacaata
781 tatacaagtg ggaaaaggag caataccacg ggaaaactaa
    tttggaaggt caaccccgaa
841 attgatacaa caatcgggga gtgggccttc tgggaaacta
    aaaaaaacct cactagaaaa
901 attcgcagtg aagagttgtc tttctctaga gcaggactga
    tcacaggcgg gagaagaact
961 cgaagagaag caattgtcaa tgctcaaccc aaatgcaacc
    ctaatttaca ttactggact
```

```
-continued
1021  actcaggatg aaggtgctgc aatcggactg gcctggatac catatttcgg gccagcagcc 1081  gagggaattt acatagaggg gctaatgcac aatcaagatg gtttaatctg tgggttgaga 1141  cagctggcca acgagacgac tcaagctctt caactgttcc tgagagccac aactgagcta 1201  cgcaccttt caatcctcaa ccgtaaggca attgatttct tgctgcagcg atgggcggc 1261  acatgccaca ttctgggacc ggactgctgt atcgaaccac atgattggac caagaacata 1321  acagacaaaa ttgatcagat tattcatgat tttgttgata aaaccttcc ggaccagggg 1381  gacaatgaca attggtggac aggatggaga caatggatac cggcaggtat tggagttaca 1441  ggcgttgtaa ttgcagttat cgctttattc tgtatatgca aatttgtctt ttag,
``` or a fragment or variant thereof encoding a functional glycoprotein. Variants can have at least 70%, 80%, 85%, 90%, 95%, 96%, 97%, 98%, 99%, or more sequence identity to SEQ ID NO:8.

In some embodiments, the chimeric viral genome includes a nucleic acid sequence encoding the polypeptide (SEQ ID NO: 9)
MGVTGILQLPRDRFKRTSFFLWVIILFQRTFSIPLGVIHSSTLQVSDVDK

LVCRDKLSSTNQLRSVGLNLEGNGVATDVPSATKRWGFRSGVPPKVVNYE

AGEWAENCYNLEIKKPDGSECLPAAPDGIRGFPRCRYVHKVSGTGPCAGD

FAFHKEGAFFLYDRLASTVIYRGTTFAEGVVAFLILPQAKKDFFSSHPLR

EPVNATEDPSSGYYSTTIRYQATGFGTNETEYLFEVDNLTYVQLESRFTP

QFLLQLNETIYTSGKRSNTTGKLIWKVNPEIDTTIGEWAFWETKKNLTRK

IRSEELSFSRAGLITGGRRTRREAIVNAQPKCNPNLHYWTTQDEGAAIGL

AWIPYFGPAAEGIYIEGLMHNQDGLICGLRQLANETTQALQLFLRATTEL

RTFSILNRKAIDFLLQRWGGTCHILGPDCCIEPEDWTKNITDKIDQIIHD

FVDKTLPDQGDNDNWWTGWRQWIPAGIGVTGVVIAVIALFCICKFVF, or a functional fragment or variant thereof. Variants can have at least 70%, 80%, 85%, 90%, 95%, 96%, 97%, 98%, 99%, or more sequence identity to SEQ ID NO:9.

In some embodiments, the Ebola G protein is lacking the mucin domain, (e.g., about amino acids 309-489 of a full length G protein), and/or has one or more substitutions (e.g. as described in Wong, et al., *J. Virol.*, 84(1):163-75 (2010), and in the examples below).

3. Additional Transgenes

Viruses can be modified to express one or more additional transgenes, separately or as a part of other expressed proteins. The viral genome of VSV has the capacity to accommodate additional genetic material. At least two additional transcription units, totaling 4.5 kb, can be added to the genome, and methods for doing so are known in the art. The added genes are stably maintained in the genome upon repeated passage (Schnell, et al., *EMBO Journal*, 17:1289-1296 (1998); Schnell, et al., *PNAS*, 93: 11359-11365 (1996); Schnell, et al., *Journal of Virology*, 70:2318-2323 (1996); Kahn, et al., *Virology*, 254, 81-91 (1999)).

In preferred embodiments the viruses are modified to include a gene encoding a therapeutic protein, an antigen, a detectable marker or reporter, a targeting moiety, or a combination thereof. In some embodiments, the gene is placed in the first gene position in the VSV background. Given the nature of VSV protein expression, genes in the first position generate the highest expression of any gene in the virus, with a 3' to 5' decrease in gene expression. The chimeric VSV can also be constructed to contain two different and independent genes placed in the first and second gene position of VSV. For example, van den Pol and Davis, et al., *J. Virol.*, 87(2):1019-1034 (2013), describes the generation of a highly attenuated VSV virus by adding two (reporter) genes to the 3' end of the VSV genome, thereby shifting the NPMGL genes from positions 1 to 5 to positions 3 to 7. This strategy can be used to allow strong expression of genes coding for any combination of two heterologous proteins, for example two therapeutic proteins, a therapeutic protein and reporter, or an immunogenic protein and a reporter that could be useful to track the virus in a clinical situation.

a. Therapeutic Proteins and Reporters

Chimeric VSV viruses can be engineered to include one or more additional genes that encode a therapeutic protein or a reporter. Suitable therapeutic proteins, such as cytokines or chemokines, are known in the art, and can be selected depending on the use or disease to be treated. Preferred cytokines include, but are not limited to, granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof.

Suitable chemokines include, but are not limited to, an alpha-chemokine or a beta-chemokine, including, but not limited to, a C5a, interleukin-8 (IL-8), monocyte chemotactic protein 1 alpha (MIP1α), monocyte chemotactic protein 1 beta (MIP1β), monocyte chemo-attractant protein 1 (MCP-1), monocyte chemo-attractant protein 3 (MCP-3), platelet activating factor (PAFR), N-formyl-methionyl-leucyl-[$^3$H]phenylalanine (FMLPR), leukotriene B$_4$, gastrin releasing peptide (GRP), RANTES, eotaxin, lymphotactin, IP10, I-309, ENA78, GCP-2, NAP-2 and MGSA/gro, and variants and fragments thereof.

Particularly preferred genes include those that encode proteins that up-regulate an immune attack on infected tumors such as IL-28, IL-2, FLT3L, and GM-CSF (Ali, et al., *Cancer Res*, 65:7194-7204 (2005); Barzon, et al., *Methods Mol. Biol.*, 542:529-549 (2009); Wongthida, et al., *Hum. Gene Ther.*, 22:1343-53 (2011). Other therapeutic proteins that have been successfully engineered into VSV or other viruses include IL2, IL-4, IL-7, IL-12, and TRAIL (Jinush, et al., *Cancer Science*, 100, 1389-1396. (2009)). The virus can also be engineered to include one or more genes encoding a reporter. The reporter can serve as a measure or monitor of in vivo viral activity. Exemplary reporters are known in the art and include, but are not limited to, carcinoembryonic antigen, secreted alkaline phosphatase, and the beta subunit of chorionic gonadotropin. These reporters are released by infected cells into the blood, and can be measured peripherally to determine viral activity, including viral activity in the brain (Phuong, et al., *Cancer Res.*, 63:2462-2469 (2003); Peng, et al., *Nat. Med.*, 8:527-531 (2002); Shashkova, et al., *Cancer Gene Ther.*, 15:61-72 (2008); Hiramatsu, et al., *Cancer Science*, 100, 1389-1396 (2005)).

In some embodiments, the virus's genome is modified to encode a detectable marker or reporter, preferably in the first position. The detectable marker allows the user to detect and monitor the location and efficacy of the virus in vivo and in resected tissue ex vivo without the need for antibodies. Suitable markers are known in the art and include, but are not limited to, LacZ, GFP (or eGFP), and luciferase.

There have been reports of humoral immune response to eGFP and rejection of eGFP transduced cells following subretinal administration of AAV2 or lentivirus expressing eGFP in animals (Bainbridge, et al., *Gene Ther.*, 10(16): 1336-44 (2003), and Doi, K., *J. Virol*, 78(20): 11327-33 (2004)). Thus, the safety and in vivo persistence of a virus including a detectable marker (e.g., one expressing eGFP) may be different than that of a virus without the marker, however, these differences can be assessed by one of skill in the art using methods known in the art and the methods described in the Examples. As discussed in more detail above, in the particular case of VSV, adding a gene added to the first position typically attenuates the virulence of VSV (Wollmann, et al., *J. Virol.*, 84(3):1563-73 (2010)). Therefore, in some embodiments, chimeric VSV that include a marker such as GFP in the first position may have an improved safety profile compared viruses without it.

b. Viruses Engineered to Deliver Vaccine Antigens

As discussed in more detail below, the virus can be a vaccine vector that serves as an immunogen for eliciting an immune response against a disease. This can be accomplished by cloning an antigen of an unrelated disease into the chimeric VSV virus. VSV viruses expressing foreign viral glycoproteins have shown promise as a vaccine vectors (Roberts, et al., *J. Virol.* 73:3723-3732 (1999), Rose, et al., *Cell,* 106:539-549 (2001), Jones, et al., *Nat. Med.* 11:786-790 (2005)). Additionally, recombinant VSVs are able to accommodate large inserts and multiple genes in their genomes. This ability to incorporate large gene inserts in replication-competent viruses offers advantages over other RNA or DNA virus vectors, such as those based on alphaviruses, REO virus, poliovirus, and parvovirus.

VSV viruses can be engineered to incorporate one or more nucleic acid sequences encoding one or more non-native or heterologous immunogenic antigens. One or more native VSV genes may be truncated or deleted to create additional space for the sequence encoding the immunogenic antigen. When expressed by the VSV virus administered to a patient in need thereof, the immunogenic antigen produces prophylactic or therapeutic immunity against a disease or disorder. Immunogenic antigens can be expressed as a fusion protein with other polypeptides including, but not limited to, native VSV polypeptides, or as a non-fusion protein. By way of non-limiting examples, the antigen can be a protein or polypeptide derived from a virus, bacterium, parasite, plant, protozoan, fungus, tissue or transformed cell such as a cancer or leukemic cell. Antigens may be expressed as single antigens or may be provided in combination.

Because the substitution of the Lassa glycoprotein for the VSV glycoprotein generates a chimeric virus that appears far safer than VSVs that contain the VSV glycoprotein, yet still retains the broad spectrum of cells to which it can bind, the chimeric virus can serve as a vaccination platform for a wide variety of microbial pathogens, including but not limited to, HIV, influenza, polio, measles, mumps, chicken pox, hendra, and others. Additionally, the fact that the Lassa-VSV chimeric virus is safe even in the brains of SCID mice lacking the normal T and B cell systemic immunity, as demonstrated in the Examples below, indicates that a vaccine based on chimeric Lassa-VSV would be safer than the corresponding vaccine based on VSV that retained its VSV glycoprotein, and therefore the chimeric Lassa-VSV might be useful in vaccinating people with depressed immune systems, for instance those with AIDS or those with genetically compromised immune systems, or patients with attenuated immunity related to ongoing cancer. The target of the vaccine could either be a type of cancer cell as a cancer treatment. Alternately, the target could be any of a large number of microbial pathogens.

c. Targeting Domains

Viruses can be engineered to include one or more additional genes that target the virus to cells of interest, see for example U.S. Pat. No. 7,429,481. In preferred embodiments, expression of the gene results in expression of a ligand on the surface of the virus containing one or more domains that bind to antigens, ligands or receptors that are specific to tumor cells, or are up-regulated in tumor cells compared to normal tissue. Appropriate targeting ligands will depend on the target cell or cancer of interest and will be known to those skilled in the art. For example, glioma stem cells are reported to express CD133 and nestin. Accordingly, in some embodiments, the viruses are engineered to express a targeting moiety that bind to CD133 or nestin.

It is believed that the Lassa glycoprotein is important for targeting chimeric Lassa-VSV virus to cells, and contributes to the desirable oncolytic profile exhibited by the chimeric Lassa-VSV virus. Accordingly, in preferred embodiments, any additional targeting ligands or moieties engineered into the virus do not reduce and preferably enhance the oncolytic activity or profile of the virus.

4. Exemplary Chimeric Viruses

Exemplary chimeric VSV viruses with Lassa virus glycoprotein are known in the art. The viruses can be used in the disclosed methods of use and treatment with or without one or more modifications, such as those discussed above.

An exemplary virus is described in Jae, et al., *Science,* 340(6151):479-483 (2013). Briefly, recombinant VSV expressing eGFP and the Lassa virus glycoprotein (rVSV-GP-LASV) was cloned and recovered as follows: the open reading frame encoding LASV-GP (strain Josiah, GenBank: HQ688673.1) was amplified using the following primer sequences: 5'-GCGACGCGTACCATGGGACAAATAGT-GACATTCT-3' (SEQ ID NO:4) and 5'-GGCGGCCGCT-CATCTCTTCCATTTCACAGG-3' (SEQ ID NO:5). Subsequently, the PCR product was sequenced and cloned into the MluI and NotI sites of pVSVAG-eGFP-MN (Whelan, et al., *Proc. Natl. Acad. Sci. U.S.A.,* 92(18):8388-92 (1995), and Wong, et al., *J. Virol.,* 84(1):163-75 (2010)) thereby replacing the native VSV glycoprotein G coding sequence. Recombinant virus was recovered and amplified as described (Whelan, et al., supra).

The genome of this Lassa-VSV includes an open reading frame encoding a GFP reporter in the first position. This allows easy detection of which cells are infected, as they turn green. In addition, having a gene added to the first position attenuates the virulence of VSV (Wollmann, et al., *J. Virol.,* 84(3):1563-73 (2010)). Accordingly, a chimeric VSV with a reporter or other heterologous gene at the first position may be attenuated or less virulent compared to the same virus without a reporter or other heterologous gene at the first position. However, as discussed in more detail in the Examples below, chimeric Lassa-VSV viruses are both efficacious and safe with or without a reporter, or another heterologous gene, in the first position. Therefore, the heterologous gene in the first position is optional.

The construction of a recombinant VSV expressing eGFP and the Ebola virus glycoprotein (rVSV-GP-EBOV) was also described in Wong, et al., *J. Virol.*, 84(1):163-75 (2010).

A second exemplary virus is discussed in Garbutt, et al., *J. Virol.*, 78(10): 5458-5465 (2004) and Geisbert, et al., *PLOS*, 2(6):537-545 (2005), which describe the construction of chimeric VSV viruses having a VSV, Indiana serotype background and a glycoprotein from Lassa virus, strain Josiah. A plasmid expressing the positive-strand RNA complement of the VSV genome with a site for foreign gene expression is described in Schnell, et al., *J. Virol.*, 70:2318-2323 (1996). This plasmid (VSVXN2) contains the five VSV genes (nucleoprotein N, phosphoprotein P, matrixprotein M, glycoprotein G, and polymerase L) in order, flanked by the bacteriophage T7 promoter, the VSV leader, and the hepatitis delta virus ribozyme, and the T7 terminator sequence. Between the G and the L genes, a linker site (XhoI-NheI) is present, flanked by a transcriptional start and stop signal for the additional gene to be expressed. As discussed in Garbutt, et al., *J. Virol.*, 78(10): 5458-5465 (2004), the plasmid can be modified to delete the G gene, and the open reading frame encoding the transmembrane glycoprotein of Lassa virus (GPC) can be prepared, for example by PCR, and cloned into the XhoI and NheI sites of the modified vector where the G gene has been deleted.

Following cloning, competent cells, for example, BSR-T7 cells, can be co-transfected with the vector and support plasmids encoding the viral ribonucleoprotein constituents (e.g., pBS-VSV N, pBS-VSV P, pBS-VSV L) to generate recombinant infectious virus that can be recovered from the supernatant of the cultured cells. Rescued rVSV can be passaged, on VeroE6 cells, for example, to obtain a virus stock.

VSV-LCMV viruses are described in U.S. Patent Application No. 2014/0301992, and 2011/0250188, and U.S. Pat. No. 6,440,730

Additional methods of making and recovering chimeric VSV virus by expressing full-length cDNA from plasmid(s) are known in the art and discussed in more detail below.

B. Pharmaceutical Compositions

Immunizing and therapeutic viruses are typically administered to a patient in need thereof in a pharmaceutical composition. Pharmaceutical compositions containing virus may be for systemic or local administration, such as intratumoral. Dosage forms for administration by parenteral (intramuscular (IM), intraperitoneal (IP), intravenous (IV), intra-arterial, intrathecal or subcutaneous injection (SC)), or transmucosal (nasal, vaginal, pulmonary, or rectal) routes of administration can be formulated. In some embodiments, a therapeutic virus is delivered by local injection, for example intracranial injection preferably at or near the tumor site. In a particular embodiment a therapeutic virus is injected directly into the tumor. The compositions can be formulated for and delivered via catheter into the tumor resection cavity through convection-enhanced delivery (CED). In some embodiments an immunizing virus is delivered peripherally, intranasally or by intramuscular injection.

As discussed in more detail below, the virus can also be used as an immunizing virus. The immunizing virus can be the same as a therapeutic virus but administered prior to a therapeutic administration so that the subject's immune system is primed to eliminate the virus following the therapeutic administration. Alternatively, the immunizing virus can be modified as discussed above to carry a disease antigen and used as part of a vaccine protocol. Immunizing viruses can be delivered peripherally, for example, by the intranasal route or by intramuscular injection.

1. Effective Amounts

As generally used herein, an "effective amount" is that amount which is able to induce a desired result in a treated subject. The desired results will depend on the disease or condition to be treated. The precise dosage will vary according to a variety of factors such as subject-dependent variables (e.g., age, immune system health, etc.), the disease, and the treatment being effected. For example, an effective amount of immunizing virus generally results in production of antibody and/or activated T cells against an antigen, or that kill or limit proliferation of or infection by a pathogen. An effective amount of the immunizing virus can be an amount sufficient to reduce neurovirulence of the therapeutic virus compared to administration of the therapeutic virus without first administering the immunizing virus.

Therapeutically effective amounts of the therapeutic viruses disclosed herein used in the treatment of cancer will generally kill tumor cells or inhibit proliferation or metastasis of the tumor cells. Symptoms of cancer may be physical, such as tumor burden, or biological such as proliferation of cancer cells. The actual effective amounts of virus can vary according to factors including the specific virus administered, the particular composition formulated, the mode of administration, and the age, weight, condition of the subject being treated, as well as the route of administration and the disease or disorder.

An effective amount of the virus can be compared to a control. Suitable controls are known in the art. A typical control is a comparison of a condition or symptom of a subject prior to and after administration of the virus. The condition or symptom can be a biochemical, molecular, physiological, or pathological readout. In another embodiment, the control is a matched subject that is administered a different therapeutic agent. Accordingly, the compositions disclosed here can be compared to other art recognized treatments for the disease or condition to be treated.

For example, the virus can be administered in an amount effective to infect and kill cancer cells, improve survival of a subject with cancer, or a combination thereof. In a particular embodiment, the cancer is glioblastoma.

One of the advantages of the disclosed viruses is that they show little or no toxicity to normal or healthy cells (e.g., non-cancerous cells). Therefore, in some embodiments the effective amount of virus causes little or no destruction of non-cancerous cells. The level of pathogenicity to normal cells can be compared to the level of pathogenicity of other VSV oncolytic viruses that do not have G gene replaced with a heterologous G gene. Such viruses are known in the art and include, for example, VSV-1'GFP, VSV-rp30, or VSV-ΔM51.

One important index of oncolytic potential is the ratio of viral replication in normal/control cells versus tumor or cancer cells. These ratios serve as an important index of the relative levels of viral replication in normal and tumor cells. A large ratio indicates greater replication in cancer cells than in control cells. In preferred embodiments, the ratio of replication of normal cells:target cells is greater than about 1:100, preferably greater than about 1:250, more preferable greater than about 1:500, most preferably greater than about 1:1000. In some embodiments, the oncolytic potential of the disclosed viruses is larger than the oncolytic potential of other VSV oncolytic viruses that do not have G gene replaced with a heterologous G gene, for example, VSV-1'GFP, VSV-rp30, or VSV-ΔM51.

2. Dosages

Appropriate dosages can be determined by a person skilled in the art, considering the therapeutic context, age, and general health of the recipient. The selected dosage depends upon the desired therapeutic effect, on the route of administration, and on the duration of the treatment desired. Active virus can also be measured in terms of plaque-forming units (PFU). A plaque-forming unit can be defined as areas of cell lysis (CPE) in monolayer cell culture, under overlay conditions, initiated by infection with a single virus particle. Generally dosage levels of virus between $10^2$ and $10^{12}$ PFU are administered to humans. Virus is typically administered in a liquid suspension, in a volume ranging between 10 μl and 100 ml depending on the route of administration. Generally, dosage and volume will be lower for intratumoral injection as compared to systemic administration or infusion. The dose may be administered once or multiple times. When administered locally, virus can be administered to humans at dosage levels between $10^2$ and $10^8$ PFU. Virus can be administered in a liquid suspension, in a low volume. For example, the volume for local administration can range from about 20 nl to about 200 μl. Multiple doses can be administered. In some embodiment, multiple injections are used to achieve a single dose. Systemic or regional administration via subcutaneous, intramuscular, intra-organ, or intravenous administration can have higher volumes, for example, 10 to 100 ml.

3. Formulations

The term "pharmaceutically acceptable" means a non-toxic material that does not interfere with the effectiveness of the biological activity of the active ingredients. The term "pharmaceutically-acceptable carrier" means one or more compatible solid or liquid fillers, diluents or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. The compositions may be administered in combination with one or more physiologically or pharmaceutically acceptable carriers, thickening agents, co-solvents, adhesives, antioxidants, buffers, viscosity and absorption enhancing agents and agents capable of adjusting osmolarity of the formulation. Proper formulation is dependent upon the route of administration chosen. If desired, the compositions may also contain minor amounts of nontoxic auxiliary substances such as wetting or emulsifying agents, dyes, pH buffering agents, or preservatives. The formulations should not include membrane disrupting agents which could kill or inactivate the virus.

a. Formulations for Local or Parenteral Administration

In a preferred embodiment, compositions including oncolytic viruses disclosed herein, are administered in an aqueous solution, by parenteral injection. Injection includes, but it not limited to, local, intratumoral, intravenous, intraperitoneal, intramuscular, or subcutaneous injection. The formulation may also be in the form of a suspension or emulsion. In general, pharmaceutical compositions are provided including effective amounts of virus, and optionally include pharmaceutically acceptable diluents, preservatives, solubilizers, emulsifiers, adjuvants and/or carriers. Such compositions include diluents such as sterile water, buffered saline of various buffer content (e.g., Tris-HCl, acetate, phosphate), pH and ionic strength; and optionally, additives such as anti-oxidants (e.g., ascorbic acid, sodium metabisulfite), and preservatives and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. A preferred solution is phosphate buffered saline or sterile saline.

b. Formulations for Mucosal Administration

In some embodiments, the compositions are formulated for mucosal administration, such as through nasal, pulmonary, or buccal delivery.

Mucosal formulations may include one or more agents for enhancing delivery through the nasal mucosa. Agents for enhancing mucosal delivery are known in the art, see, for example, U.S. Patent Application No. 200910252672 to Eddington, and U.S. Patent Application No. 2009/0047234 to Touitou. Acceptable agents include, but are not limited to, chelators of calcium (EDTA), inhibitors of nasal enzymes (boro-leucin, aprotinin), inhibitors of muco-ciliary clearance (preservatives), solubilizers of nasal membrane (cyclodextrin, fatty acids, surfactants) and formation of micelles (surfactants such as bile acids, Laureth 9 and taurodehydrofusidate (STDHF)). Compositions may include one or more absorption enhancers, including surfactants, fatty acids, and chitosan derivatives, which can enhance delivery by modulation of the tight junctions (TJ) (B. J. Aungst, et al., *J. Pharm. Sci.* 89(4):429-442 (2000)). In general, the optimal absorption enhancer should possess the following qualities: its effect should be reversible, it should provide a rapid permeation enhancing effect on the cellular membrane of the mucosa, and it should be non-cytotoxic at the effective concentration level and without deleterious and/or irreversible effects on the cellular or virus membrane, Intranasal compositions maybe administered using devices known in the art, for example a nebulizer.

III. Methods of Use

A. Methods of Treatment

1. Administration of Therapeutic Virus

The disclosed chimeric VSV viruses can be administered to a subject in need thereof in an amount effective to treat a disease or disorder, for example, cancer. Pharmaceutical compositions including a chimeric virus may be administered once or more than once, for example 2, 3, 4, 5, or more times. Serial administration of chimeric virus may occur days, weeks, or months apart. As discussed in more detail below, boosters of immunizing virus may be administered between therapeutic treatments. It may be particularly preferable to administer a booster of immunizing virus if there are lengthy delays between treatments with therapeutic virus, for example, one or more years.

Virus can be administered peripherally, or can be injected directly into a tumor, for example a tumor within the brain. In addition, virus can be used after resection of the main body of the tumor, for example by administering directly to the remaining adjacent tissue after surgery, or after a period of one to two weeks to allow recovery of local damage. Adding virus after surgical resection would eliminate any remaining tumor cells that the neurosurgeon did not remove. The injections can be given at one, or multiple locations. It is also believed that virus administered systemically can target and kill brain cancers.

In some embodiments, it may be desirable to administer the chimeric virus after or in combination with an immunosuppressant. Treatment with an immunosuppressant during administration with a therapeutic virus allows controlled suppression of the subject's immune system during administration of the therapeutic virus. This may be desirable, for example, if the capacity of the oncolytic virus to kill cancer is reduced due to an earlier administration of the immunizing virus. Treatment with the immunosuppressant is typically transient, and occurs during administration of the virus, particularly when the virus is being used to treat tumors and/or cancer. Following treatment with the chimeric virus, treatment with the immunosuppressant is discontinued and the patient's immunity returns. The duration of immunosuppressive treatment will depend on the condition to be treated. Typically the immunosuppressive treatment will be long enough for the oncolytic virus to kill cancer cells, reduce tumor size, or inhibit tumor progression.

2. Peripheral Administration of Immunizing Virus

One or more peripheral administrations with an immunizing virus can elicit an adaptive immune response that protects the brain from potential side-effects of oncolytic virus therapy. The term immunizing virus includes live virus as well as viral subunits, proteins and fragments thereof, antigenic polypeptides, nucleic acids, and expression vectors containing nucleic acids encoding viral subunits, proteins, or fragments thereof, or antigenic polypeptides which can be useful in eliciting an immune response. For example, if the immunizing virus is a VSV virus, the immunizing virus includes, but is not limited to, live VSV virus, the N, P, M, G, or L proteins, or combinations thereof.

The immunizing virus may be the same virus, or a different virus than the therapeutic virus. The immunizing virus should initiate an adaptive immune response that is sufficient to attenuate, reduce, or prevent the neurovirulence of the therapeutic virus. The therapeutic virus administered after a first administration of immunizing virus should have reduced neurovirulence compared to therapeutic virus administered without a first administration of immunizing virus. In preferred embodiments, the immunizing virus is similar to the therapeutic virus. For example if the therapeutic virus is a VSV, the immunizing virus is preferably a VSV, or an antigenic protein or nucleic acid component thereof. In some embodiments the immunizing virus has an attenuated phenotype compared to the therapeutic virus. As described above, suitable immunizing viruses include wildtype viruses, as well as mutant and variants thereof. In one preferred embodiment, the immunizing virus is a wildtype virus or an antigenic protein or nucleic acid component thereof, while the therapeutic virus is a mutant, variant, chimeric virus having the same virus background but reduced neurovirulence compared to wildtype. In some embodiments, therapeutic viruses may be engineered to express therapeutic proteins or targeting molecules. Immunizing viruses may also be engineered to express additional proteins, but preferably are not. VSV-G/GFP is a suitable immunizing virus. The nucleotide sequence for VSV-G/GFP is GenBank Accession FJ478454.

Immunizing viruses are administered sufficiently prior to therapeutic viruses to elicit an adaptive immune response. Immunizing viruses are typically administered one or more times at least about 5 days, preferably 1 week, more preferably greater than one week before administration of the therapeutic virus. Immunizing viruses can be administered up to 1, 2, 3, 4, 5, or more weeks before the therapeutic virus. Immunizing viruses can be administered up to 1, 2, 3, 4, 5, or more months before the therapeutic virus. Most preferably the immunizing virus is administered between about ten days and 12 weeks before the therapeutic virus.

After an initial administration of the immunizing virus, subsequent booster immunizations can be administered. For example, it may be desirable to administer the immunizing virus two or more times. A first administration of the immunizing virus is typically provided to a patient in need therefore prior to a first administration of the therapeutic virus. Subsequent administrations of the immunizing virus may occur before and/or after a first administration of the therapeutic virus. In preferred embodiments the immunizing virus is administered two or more times before the first administration of the therapeutic virus. In a non-limiting example, the immunizing virus is first administered on day 1, a booster of immunizing virus is administered six weeks later on about day 43, and the therapeutic virus is first administered two weeks later on about day 57.

Various factors may be considered when determining the frequency, dosage, duration, and number of administrations of immunizing virus, as well as the duration between administration of the immunizing virus and first administration of therapeutic virus. For example, the subject's adaptive immune response can be monitored to assess the effectiveness of the immunization. Methods of measuring adaptive immune activation are known in the art and include antibody profiling, serum analysis for changes in levels of antibodies, cytokines, chemokines, or other inflammatory molecules, and cell counts and/or cell profiling using extracellular markers to assess the numbers and types of immune cells such as B cells and T cells.

Immunizing virus is most typically delivered to a subject in need thereof by peripheral administration, and not directly or locally to the site in need of treatment by therapeutic virus. Peripheral administration includes intravenous, by injection or infusion, intraperitoneal, intramuscular, subcutaneous, and mucosal such as intranasal delivery. In some embodiments, the composition is delivered systemically, by injection or infusion into the circulatory system (i.e. intravenous) or an appropriate lymphoid tissue, such as the spleen, lymph nodes or mucosal-associated lymphoid tissue. The injections can be given at one, or multiple locations. Preferably the immunizing virus is administered intranasally or by intramuscular injection, most preferably by intranasal delivery.

Generally immunizing virus is administered to humans at dosage levels between $10^2$ and $10^{12}$ PFU. Virus is typically administered in a liquid suspension, in a volume ranging between 10 µl and 100 ml depending on the route of administration.

It may also be desirable to administer the immunizing virus in combination with one or more adjuvants. These can be incorporated into, administered with, or administered separately from, the immunogenizing virus. Depending on whether or not the individual is a human or an animal, the adjuvant can be, but is not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

3. Vaccination

The chimeric viruses can also serve as an immunogen for generating an immune response against other antigens administered with or cloned into virus. The safety profile of the disclosed Lassa-VSVs make them particularly attractive for use as part of a vaccine. Other VSVs can lead to adverse consequence in brain, whereas a Lassa-VSV with another antigen, for example, an influenza antigen, would be safer, yet effective.

For example, in some embodiments, the chimeric virus is a vaccine vector. Experiments conducted with the Lassa-VSV including a GFP reporter discussed below, show that the chimeric virus generates a strong immune response against the virus, and also against the GFP reporter. Accordingly, other proteins could be substituted for GFP. These could include proteins from pathogenic microbes unrelated to Lassa virus or VSV; the Lassa-VSV could serve as a safe vaccine platform against many different pathogenic microbes. As described above, VSV can be engineered to express one or more immunogenic antigens. Expression of these antigens in a patient in need thereof presents the antigen to the immune system and provokes an immune response. Vaccines can be administered prophylactically or therapeutically. Vaccines can also be administered according to a vaccine schedule. A vaccine schedule is a series of vaccinations, including the timing of all doses. Many vaccines require multiple doses for maximum effectiveness, either to produce sufficient initial immune response or to boost response that fades over time. Vaccine schedules are known in the art, and are designed to achieve maximum effectiveness. The adaptive immune response can be monitored using methods known in the art to measure the effectiveness of the vaccination protocol.

4. Immunotherapy

Chimeric VSV viruses wherein the G protein is replaced with a heterologous glycoprotein, for example the glycoprotein from Lassa virus, have been shown to be immunogenic and initiate an up-regulation of both humoral and cellular immunity toward the virus (Geisbert, et al., *PLoS Med.*, 2:e183 (2005) and the Examples below. Therefore, methods of initiating an immune response against the infected tumor are disclosed. It is believed that the disclosed chimeric viruses will not only infect and kill cancer cells, but will enhance an attack by the systemic immune system on the infected cell-type both during and after the virus is eliminated. In this way, the virus can be used to induce an immune response against non-infected target cells. In this way, treatment with the disclosed VSV virus may delay, reduce, or prevent reoccurrence of the cancer being treated.

In some methods, the chimeric virus is used to infect targets cells, and the infected target cells or antigens isolated therefrom are used for peripheral immunization of the subject against the target cells, or antigens thereof. For example, target cells against which an immune response is desired are implanted into a subject. The cells are injected with virus which kills the cells and leads to an immune response against antigens of the cells. The cells can be infected with virus before or after implantation. For example, the cells are infected with virus in vitro prior to injection into the subject. In another embodiment, the subject is immunized with antigen(s) isolated from tumor cells infected with virus in vitro.

The target cell can be any cell to which an immune response is desired. For example, the target cells can be cancer cells against which an immune response is desired. The cancer cells can be from an established cell line or primary cancer cells isolated from a subject. For example, the target cells can be cancer cells isolated from a subject in a biopsy or during surgery to remove a tumor. As discussed above, the target cells can be infected in vitro prior to administration to the subject, or the target cells can be inject by local injection of the virus into the subject at the site of implantation of the target cells. The cells can be harvested from and administered back to the same subject. Alternatively, the cells can be harvested from one subject and administered to a different subject. In this way, the virus can be used to induce an immune response against a cancer or tumor in a subject that has the cancer or tumor, or prophylactically prime the immune system to attack a future cancer or tumor that the subject does not yet have. Accordingly, the treatment can be therapeutic, prophylactic, or a combination thereof.

In a particular embodiment, this strategy is employed in combination with surgery in which a tumor is removed from a subject. Cells are isolated from the tumor, infected with virus, and implanted in the subject. In this way, an immune response is induced against any cancer cells that remain in the subject, for example in the margins and other tissue at the site from which the tumor removed, as well as circulating cancer cells and metastases throughout the body including those sites distant from the tumor that was removed. The method can also reduce, delay, or prevent recurrence of the cancer.

In some embodiments the isolated target cells are irradiated in amount effective to prevent cell division, but not to kill the cells, to avoid concerns about in vivo replication of the target cells following implantation. Typically, the cells are implanted into the subject peripherally. For example, the cells can be injected into the subject subcutaneously, intramuscularly, intranasally, intravenously, intraperitoneally, or using another suitable method of peripheral administration, such as those discussed above. In some embodiments, the tumor cells are expanded in culture for one or generations or passages between isolation and implantation in the subject.

It is believed that VSV infection will increase tumor-specific cytotoxic effector CD8+ T cells, increase CD4+ T cells, increase production of tumor specific antibodies, or a combination thereof. Therefore, in some embodiments, tumor-specific cytotoxic effector CD8+ T cells primed by chimeric VSV infected tumor cells are administered to a subject in need thereof. The T cells can be harvested from a treated subject, and optionally expanded in culture, or primed and expanded in vitro.

For example, in a particular embodiment, the method is one of adaptive T cell therapy. Methods of adoptive T cell therapy are known in the art and used in clinical practice. Generally adoptive T cell therapy involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells which can attack and kill cancer. Several forms of adoptive T cell therapy can be used for cancer treatment including, but not limited to, culturing tumor infiltrating lymphocytes or TIL; isolating and expanding one particular T cell or clone; and using T cells that have been engineered to recognize and attack tumors. In the disclosed methods, tumors infected with the chimeric VSV, or isolated components thereof, are used to prime the T cells. In some embodiments, the T cells are taken directly from the patient's blood after they have received treatment or immunization with the virus. Methods of priming and activating T cells in vitro for adaptive T cell cancer therapy are known in the art. See, for example, Wang, et al., Blood, 109(11): 4865-4872 (2007) and Hervas-Stubbs, et al., *J. Immunol.*, 189(7):3299-310 (2012). The methods can be used in conjunction with virus infected cancer cells, or antigens isolated therefrom, to prime and activate T cells against the cancer.

Historically, adoptive T cell therapy strategies have largely focused on the infusion of tumor antigen specific cytotoxic T cells (CTL) which can directly kill tumor cells. However, CD4+ T helper (Th) cells can also be used. Th can activate antigen-specific effector cells and recruit cells of the innate immune system such as macrophages and dendritic cells to assist in antigen presentation (APC), and antigen primed Th cells can directly activate tumor antigen-specific CTL. As a result of activating APC, antigen specific Th1 have been implicated as the initiators of epitope or determinant spreading which is a broadening of immunity to other antigens in the tumor. The ability to elicit epitope spreading broadens the immune response to many potential antigens in the tumor and can lead to more efficient tumor cell kill due to the ability to mount a heterogeneic response. In this way, adoptive T cell therapy can used to stimulate endogenous immunity.

B. Subjects to be Treated

In general, the disclosed chimeric viruses and methods of treatment thereof are useful in the context of cancer, including tumor therapy, particular brain tumor therapy.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The compositions and methods described herein are useful for treating subjects having benign or malignant tumors by delaying or inhibiting the growth of a tumor in a subject, reducing the growth or size of the tumor, inhibiting or reducing metastasis of the tumor, and/or inhibiting or reducing symptoms associated with tumor development or growth. The examples below indicate that the viruses and methods disclosed herein are useful for treating cancer, particular brain tumors, in vivo.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. The disclosed compositions are particularly effective in treating carcinomas. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, cancers such as vascular cancer such as multiple myeloma, adenocarcinomas and sarcomas, of bone, bladder, brain, breast, cervical, colo-rectal, esophageal, kidney, liver, lung, nasopharangeal, pancreatic, prostate, skin, stomach, and uterine. In some embodiments, the disclosed compositions are used to treat multiple cancer types concurrently. The compositions can also be used to treat metastases or tumors at multiple locations.

The disclosed methods are particularly useful in treating brain tumors. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells, lymphatic tissue, blood vessels), in the cranial nerves, in the brain envelopes (meninges), skull, pituitary and pineal gland, or spread from cancers primarily located in other organs (metastatic tumors). Examples of brain tumors include, but are not limited to, oligodendroglioma, meningioma, supratentorial ependymona, pineal region tumors, medulloblastoma, cerebellar astrocytoma, infratentorial ependymona, brainstem glioma, schwannomas, pituitary tumors, craniopharyngioma, optic glioma, and astrocytoma.

"Primary" brain tumors originate in the brain and "secondary" (metastatic) brain tumors originate from cancer cells that have migrated from other parts of the body. Primary brain cancer rarely spreads beyond the central nervous system, and death results from uncontrolled tumor growth within the limited space of the skull. Metastatic brain cancer indicates advanced disease and has a poor prognosis. Primary brain tumors can be cancerous or noncancerous. Both types take up space in the brain and may cause serious symptoms (e.g., vision or hearing loss) and complications (e.g., stroke). All cancerous brain tumors are life threatening (malignant) because they have an aggressive and invasive nature. A noncancerous primary brain tumor is life threatening when it compromises vital structures (e.g., an artery). In a particular embodiment, the disclosed compositions and methods are used to treat cancer cells or tumors that have metastasized from outside the brain (e.g., lung, breast, melanoma) and migrated into the brain.

The Examples below illustrate that Lassa-VSV is oncolytic, but also non-toxic to health or normal cells, even when administered directly to the brain. Therefore, the disclosed viruses are particularly useful for treating brain cancer, cancer that can metastasize to the brains, for example lung cancer, breast cancer, and skin cancer such as melanoma.

Although the viruses are particularly safe and useful for treating cancer in the brain, the cancer does not have to be in the brain. It is believed that the chimeric virus are also effective for treating other cancer outside the brain, and can thereof be administered systemically in or locally outside the brain. In a particular embodiment, a chimeric virus is used to treat a cancer that could, but has not yet metastasized to the brain. See, for example, Yarde, et al., *Cancer Gene Ther.*, 2013 Nov. 1. doi: 10.1038/cgt.2013.63, which describes that intravenously administered VSVs encoding IFN-β have potent activity against subcutaneous tumors in the 5TGM1 mouse myeloma model, without attendant neurotoxicity.

However, when 5TGM1 tumor cells were seeded intravenously, virus-treated mice with advanced myeloma developed clinical signs suggestive of meningoencephalitis, and leading to deaths that are believed to be associated with viral toxicity. Histological analysis revealed that systemically administered 5TGM1 cells seed to the CNS, forming meningeal tumor deposits, and that VSV infects and destroys these tumors. Death is presumably a consequence of meningeal damage and/or direct transmission of virus to adjacent neural tissue.

The disclosed chimeric Lassa-VSV viruses have reduced toxicity for normal and healthy cells including neurons. Therefore, these viruses are a safer, less toxic alternative for treating systemic cancers that can potential traffic virus into the brain and cause neurotoxicity and even death.

As shown the examples below, the chimeric Lassa-VSV was safe in the brains of SCID mice that have a depressed systemic immunity due to substantially reduced T and B cells. Thus, Lassa-VSV should be far safer than VSV with its normal VSV glycoprotein. This may enable Lassa-VSV to be used in patients showing depressed immunity, typical of many cancer patients, and also of patients with AIDS, or with genetic immune depression. The enhanced safety in the brain may also be of benefit in patients with compromised blood brain barriers where Lassa-VSV would be safer than VSV in both cancer treatment, and for vaccination against either a cancer cell type, or against unrelated (e.g., non-Lassa, non-VSV) pathogenic microbes.

The Examples below also show that the chimeric VSV are effective at infecting and replicating in colon, prostate, breast, bone, and bladder cancer cells, indicating its oncolytic potential was not restricted to glioma and melanoma brain tumors. It is believed that the disclosed viruses are effective for treating both primary and secondary brain tumors, but as peripheral (non-brain) cancers and tumors.

C. Combination Therapies

Administration of the disclosed compositions containing oncolytic viruses may be coupled with surgical, radiologic, other therapeutic approaches to treatment of tumors and cancers.

1. Surgery

The disclosed compositions and methods can be used as an adjunct to surgery. Surgery is a common treatment for many types of benign and malignant tumors. As it is often not possible to remove all the tumor cells from during surgery, the disclosed compositions containing oncolytic virus are particularly useful subsequent to resection of the primary tumor mass, and would be able to infect and destroy even dispersed tumor cells.

In a preferred embodiment, the disclosed compositions and methods are used as an adjunct or alternative to neurosurgery. The compositions are particularly well suited to treat areas of the brain that is difficult to treat surgically, for instance high grade tumors of the brain stem, motor cortex, basal ganglia, or internal capsule. High grade gliomas in these locations are generally considered inoperable. An additional situation where an oncolytic virus may be helpful is in regions where the tumor is either wrapped around critical vasculature, or in an area that is difficult to treat surgically.

2. Therapeutic Agents

The viral compositions can be administered to a subject in need thereof alone or in combination with one or more additional therapeutic agents selected based on the condition, disorder or disease to be treated. A description of the various classes of suitable pharmacological agents and drugs may be found in Goodman and Gilman, *The Pharmacological Basis of Therapeutics*, (11th Ed., McGraw-Hill Publishing Co.) (2005).

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, irinotecan, leucovorin, liposomal doxorubicin, liposomal daunorubicin, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2), and combinations thereof.

Preferred chemotherapeutics will affect tumors or cancer cells, without diminishing the activity of the virus. For example, in a preferred embodiment, the additional therapeutic agent inhibits proliferation of cancer cells without affecting targeting, infectivity, or replication of the virus.

a. Anticancer Agents

The compositions can be administered with an antibody or antigen binding fragment thereof specific for growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

b. Therapeutic Proteins

It may be desirable to administer the disclosed compositions in combination with therapeutic proteins. VSV is an effective oncolytic virus, in-part, by taking advantage of defects in the interferon system. Administration of therapeutic proteins such as IFN-α, or IFN-α/β pathway inducer polyriboinosinic polyribocytidylic acid [poly(I:C)] are effective in protecting normal cells from the oncolytic activity, while leaving the tumor cells susceptible to infection and death (Wollmann, et al. *J. Virol.*, 81(3): 1479-1491 (2007). Therefore, in some embodiments, the disclosed compositions are administered in combination with a therapeutic protein to, reduce infectivity and death of normal cells.

Other therapeutic proteins that can be administered in combination with the disclosed viruses include those provided above as therapeutic proteins that can be engineered into the virus. Accordingly, the therapeutic virus can be part of the virus itself, or administered separately. In some embodiments, the virus includes one or more therapeutic proteins and one more therapeutic proteins are administered separately.

c. Immuno-Suppressants

As discussed throughout and demonstrated in the Examples below, the disclosed chimeric VSV viruses generally, show a reduced probability of infecting normal brain cells, but still have a good oncolytic capacity. One limitation of oncolytic viruses in general is that the adaptive immune system can up-regulate its antiviral response and eliminate the virus before the virus has had a chance to maximally infect tumor cells. Although it is important for the adaptive immune system to eliminate the chimeric VSV from the subject, the virus should remain in the subject long enough to infect and kill as many tumor cells as possible balanced against the pathogenicity of the virus to normal cells of the subject. Temporary concomitant immune-suppression has been identified as a strategy to enhance the efficacy of other oncolytic viruses (HSV, adenovirus, vaccinia) that are human pathogens and face pre-existing immunity (Fukuhara, et al., *Curr. Cancer Drug Targets*, 7:149-155 (2007); Lun, et al., *Clin. Cancer Res.*, 15:2777-2788 (2009)). Therefore, the virus can be administered to the subject in combination with temporary concomitant immune suppression.

In some embodiments, the virus is administered in combination with an agent that reduces or attenuates the intrinsic IFN-mediated immune responses that can eliminate the virus before it has achieved maximal tumor destruction. In preferred embodiments, the attenuation of the intrinsic IFN-mediated immune responses enhances the rate of recombinant VSV-mediated tumor destruction without increasing infection of normal cells. This strategy should also reduce the initiation of the adaptive immune response which is enhanced by the innate immune response, giving the virus more time to complete its oncolytic actions.

Paglino, et al., *J. Virol.*, 85:9346-58 (2011) showed that a cancer cell highly resistant to VSV could be infected by blocking the IFN response to VSV with one of three IFN blockers, valproate, the vacccinia protein B18R, or Jak inhibitor 1. Valproate crosses the blood brain barrier as evident in its use to treat epilepsy. It is already approved for clinical use in humans (for attenuating epilepsy), and like many other histone deacetylase (HDAC) inhibitors, it has an intrinsic anti-tumor property, independent of oncolytic virus infection, that reduces glioma and other tumor growth in the brain (Chateauvieux, et al., *J. Biomed. Biotechnol.*, 479364. Epub 2010 Jul. 29 (2010); Fu, et al., *Neuro. Oncol.*, 12:328-340 (2010); Su, et al., *Clin. Cancer Res.*, 17:589-597 (2011).

Similarly, the HDAC inhibitor vorinostat (ZOLLNZA®) is approved by the FDA for the treatment of cutaneous T-cell lymphoma (Glaser K B, *Biochem. Pharmacal.*, 74:659-671 (2007)). Vorinostat on its own appears to penetrate brain tumors and to increase survival of patients with glioblastoma, and animal studies have shown that valproate can increase infection by viruses in tumors with minimal increased collateral damage. Valproate increased survival substantially in tumor bearing animals treated with HSV (Otsuki, et al., *Mol. Ther.*, 16:1546-1555 (2008)). In one particular ease study a pediatric anaplastic astrocytoma that was resistant to chemotherapy and irradiation, underwent a substantial regression after combined treatment with oral valproate and oncolytic attenuated Newcastle disease virus Wagner, et al., *APMIS,* 114:731-743 (2006)).

Other HDAC inhibitors have been shown to enhance viral cancer cell targeting and viral replication by vaccinia (MacTavish, et al., *PLoS One,* 5:e14462 (2010) and VSV (Nguyen, et al., *Proc. Natl. Acad. Sci., USA* 105:14981-14986 (2008)) without substantially altering infection in normal non-cancer cells. Valproate inhibited the induction of several antiviral genes after oncolytic HSV infection, and resulted in enhanced viral propagation in glioma cells, even in the presence of IFN (Otsuki, et al., *Mol. Ther.*, 16:1546-1555 (2008)). Importantly, valproate treatment had no augmenting effect on viral yield in normal human astrocytes. Valproate pretreatment was also shown to enhance HSV propagation in tumors 10-fold in vivo and improved the survival of nude mice bearing U87delta-EGFR brain tumors.

Therefore, in some embodiments, the virus is administered in combination with an HDAC inhibitor. In some embodiments, the virus is administered in combination with valproate, the vacccinia protein B18R, Jak inhibitor 1, or vorinostat.

Other immunosuppressants such as cyclosporin, prednisone, dexamethasone, or other steroidal anti-inflammatory, can also be used to reduce the immune response immediately before, during, or shortly after administration of the therapeutic virus. The immunosuppressant is then discontinued or decreased to allow the patient's immune system to prevent inflammation and/or killing of the virus after it has competed the desired killing of tumor or diseased tissue.

Suitable immunosuppressants are known in the art and include glucocorticoids, cytostatics (such as alkylating agents, antimetabolites, and cytotoxic antibodies), antibodies (such as those directed against T-cell recepotors or 11-2 receptors), drugs acting on immunophilins (such as cyclosporine, tacrolimus, and sirolimus) and other drugs (such as interferons, opioids, TNF binding proteins, mycophenolate, and other small molecules such as fingolimod). The dosage ranges for immunosuppressant agents are known in the art. The specific dosage will depend upon the desired therapeutic effect, the route of administration, and on the duration of the treatment desired. For example, when used as an immunosuppressant, a cytostatic maybe administered at a lower dosage than when used in chemotherapy. Immunosuppressants include, but are not limited to, FK506, prednisone, methylprednisolone, cyclophosphamide, thalidomide, azathioprine, and daclizumab, physalin B, physalin F, physalin G, seco-steroids purified from *Physalis angulata L.*, 15-deoxyspergualin, MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane, paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea, and combinations thereof. Preferred immunosuppressants will preferentially reduce or inhibit the subject's immune response, without reducing or inhibiting the activity of the virus.

IV. Kits

Dosage units including virus in a pharmaceutically acceptable carrier for shipping and storage and/or administration are also disclosed. Active virus should be shipped and stored using a method consistent with viability such as in cooler containing dry ice so that viruses are maintained below 4° C., and preferably below −20° C. VSV virus should not be lyophilized. Components of the kit may be packaged individually and can be sterile. In one embodiment, a pharmaceutically acceptable carrier containing an effective amount of virus is shipped and stored in a sterile vial. The sterile vial may contain enough virus for one or more doses. Virus may be shipped and stored in a volume suitable for administration, or may be provided in a concentrated titer that is diluted prior to administration. In another embodiment, a pharmaceutically acceptable carrier containing an effective amount of virus can be shipped and stored in a syringe.

Typical concentrations of concentrated viral particles in the sterile saline, phosphate buffered saline or other suitable media for the virus is in the range of $10^8$ to $10^9$ with a maximum of $10^{12}$. Dosage units should not contain membrane disruptive agents nor should the viral solution be frozen and dried (i.e., lyophilized), which could kill the virus.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. For example, in one embodiment, a syringe for administering virus intratumorally, is capable of accurately delivering a smaller volume (such as 1 to 100 µl). Typically, a larger syringe, pump or catheter will be used to administer virus systemically. Any of the kits can include instructions for use.

V. Methods of Manufacture

A. Engineering Recombinant VSV Viruses

The native VSV genome is a single negative-sense, non-segmented stand of RNA that contains five genes (N, L, P, M, and G) and has a total size of 11.161 kb. Methods of engineering recombinant viruses by reconstituting VSV from DNA encoding a positive-sense stand of RNA are known in the art (Lawson, et al., PNAS, 92:4477-4481 (1995), Dalton and Rose, *Virology.*, 279:414421 (2001)). For example, recombinant DNA can be transcribed by T7 RNA polymerase to generate a full-length positive-strand RNA complimentary to the viral genome. Expression of this RNA in cells also expressing the VSV nucleocapsid protein and the two VSV polymerase subunits results in production of VSV virus (Lawson, et al., PNAS, 92:4477-4481 (1995)). In this way, VSV viruses can be engineered to express variant proteins, additional proteins, foreign antigens, targeting proteins, or therapeutic proteins using known cloning methods. Methods of preparing exemplary suitable VSV viruses where the gene encoding the VSV G protein is deleted and replaced with a gene encoding the Lassa virus glycoprotein are described in more detail above.

In some embodiments, the chimeric VSV is prepared by substituting the sequence encoding the G protein on the plasmid referred as VSVXN2 (Schnell, et al., *J. Viral.*, 70:2318-2323 (1996)) with a heterologous glycoprotein, such as the glycoprotein from Lassa virus.

In other embodiments the chimeric VSV is prepared by substituting the sequence encoding the G protein on plasmid pVSV(+) described in Whelan, et al., *Proc. Natl. Acad. Sci. USA.*, 92(18):8388-92 (1995). Whelan describes the constructions of a full-length cDNA clone of VSV assembled from clones of each of the VSV genes and intergenic junctions. These clones were assembled into a full-length cDNA and inserted in both orientations between the bacteriophage T7 promoter and a cDNA copy of the self-cleaving ribozyme from the antigenomic strand of HDV. The resulting plasmids were named pVSV1(+) and pVSV1(−) to reflect the polarity of the T7 transcript they generated: VSV antigenomic or genomic RNA, respectively.

The T7 transcripts contained two non-VSV nucleotides (GG) at their 5' ends but were cleaved by the HDV ribozyme to generate a 3' terminus which corresponded precisely to the 3' end of the VSV antigenomic or genomic sequence, an important requirement for VSV RNA replication. Transfection of plasmids into BHK21 cells infected with vTF7-3 was performed under the conditions and with quantities of support plasmids as described (Pattnaik, et al., Cell, 69:1011-1020 (1992)), and up to 5 ug of pVSV1(+) or pVSV1(−). Transfected cells were incubated at 31° C. or 37° C. For some experiments, pVSV1(+) and pVSV1(−) were linearized by digestion at a unique Nhe I site located downstream of the T7 terminator in the pGEM-3-based plasmids.

To identify cDNA-derived virus unambiguously, several genetic markers were incorporated into the full-length cDNA clones. All five genes were of the Indiana serotype of VSV, but whereas the N, P, M, and L genes originated from the San Juan strain, the G gene was from the Orsay strain. In addition, the functional P clone has 28 nucleotide sequence differences from the published San Juan sequence and in the case of pVSV1(+) the 516 nt at the 5' end of the VSV genome originated from pDI, the clone of DI-T RNA (Pattnaik, et al., Cell, 69:1011-1020 (1992)).

B. Creating Mutant VSV Virus

RNA viruses are prone to spontaneous genetic variation. The mutation rate of VSV is about $10^{-4}$ per nucleotide replicated, which is approximately one nucleotide change per genome (Drake, et al., *Proc. Natl. Acad. Sci. USA,* 96:13910-13913). Therefore, mutant VSV viruses exhibiting desired properties can be developed by applying selective pressure. Methods for adaption of VSV viruses through repeated passaging is described in the art. See, for example, Wollmann, et al., *J. Virol.*, 79(10): 6005-6022 (2005). Selective pressure can be applied by repeated passaging and enhanced selection to create mutant virus with desirable traits such as increased infectivity and oncolytic potential for a cell type of interest. The cell type of interest could be general, such as cancer cells, or specific such as glioblastoma cells. Mutant virus can also be selected based on reduced toxicity to normal cells. Methods of enhanced selection include, but are not limited to, short time for viral attachment to cells, collection of early viral progeny, and preabsorption of viral particles with high affinity of undesirable cells (such as normal cells). Mutations can be identified by sequencing the viral genome and comparing the sequence to the sequence of the parental strain.

DNA encoding the VSV genome can also be used as a substrate for random or site directed mutagenesis to develop VSV mutant viruses. Mutagenesis can be accomplished by a variety of standard, mutagenic procedures. Changes in single genes may be the consequence of point mutations that involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of nucleic acid replication or the movement of transposable genetic elements (transposons) within the genome. They also are induced following exposure to chemical or physical mutagens. Such mutation-inducing agents include ionizing radiations, ultraviolet light and a diverse array of chemicals such as alkylating agents and polycyclic aromatic hydrocarbons all of which are capable of interacting either directly or indirectly (generally following some metabolic biotransformations) with nucleic acids. The nucleic acid lesions induced by such environmental agents may lead to modifications of base sequence when the affected DNA is replicated or repaired and thus to a mutation. Mutation also can be site-directed through the use of particular targeting methods. Various types of mutagenesis such as random mutagenesis, e.g., insertional mutagenesis, chemical mutagenesis, radiation mutagenesis, in vitro scanning mutagenesis, random mutagenesis by fragmentation and reassembly, and site specific mutagenesis, e.g., directed evolution, are described in U.S. Patent Application No. 2007/0026012.

Mutant viruses can be prepared by site specific mutagenesis of nucleotides in the DNA encoding the protein, thereby producing DNA encoding the mutant. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Insertions usually will be on the order of about from 1 to 10 amino acid residues; and deletions will range about from 1 to 30 residues. Substitutions, deletions, insertions or any combination thereof can be combined to arrive at a final construct. The mutations must not place the sequence out of reading frame and preferably will not create complementary regions that could produce secondary mRNA structure. Substitution variants are those in which at least one residue has been removed and a different residue inserted in its place.

EXAMPLES

Example 1

Chimeric Lassa-VSV Virus Infected and Killed Gliomas Without Causing Neurological Dysfunction Materials and Methods
Viruses and Cells
VSV-wtG and chimeric VSV's expressing the G protein from either Lassa fever virus (VSV-LASV-G), rabies virus (VSV-RABV), lymphocytic choriomeningitis virus (VSV-LCMV-G), Ebola virus (VSV-EBOV-G), or Marburg virus (VSV-MARV-G) were generated as described previously (Beier, et al., *Proc. Natl. Acad. Sci. USA*, 108:15414-15419 (2011); Jae, et al., *Science*, 344:1506-1510 (2014); Krishnan, et al., *Viruses*, 4:2471-2484. A GFP reporter gene was engineered into the first genome position of these VSVs. VSV-EBOV-G and VSV-LASV-G that did not express any reporter genes were also tested in some assays (Garbutt, et al., *J Virol.*, 78(10):5458-65 (2004)).
VSV-EBOV
The EBOV glycoprotein sequence expressed in VSV-EBOV is derived from the Mayinga strain of Zaire Ebola virus as described in the methods of Garbutt, et al. (2004) J. Virol 78: 5458-5465. The nucleotide sequence shown below was determined by direct sequencing of VSV-EBOV samples and matches the sequence for the full-length (non-secreted) glycoprotein gene found in GenBank accession NC_002549 nt 6039-8068. Note that the GenBank sequence over this region is 2030 nt long, whereas the sequence below is 2031 nt in length. This difference derives from the fact that the GenBank sequence is based on the genomic RNA sequence, whereas the sequence below is based on the mRNA sequence that has been 'edited' by the viral polymerase to include an extra 'A' nucleotide between 6918-6924 of the GenBank sequence.

VSV-EBOV glycoprotein gene nucleotide sequence (2031 nt)

(SEQ ID NO: 6)
ATGGGCGTTACAGGAATATTGCAGTTACCTCGTGATCGATTCAAGAGGAC

ATCATTCTTTCTTTGGGTAATTATCCTTTTCCAAAGAACATTTTCCATCC

CACTTGGAGTCATCCACAATAGCACATTACAGGTTAGTGATGTCGACAAA

CTAGTTTGTCGTGACAAACTGTCATCCACAAATCAATTGAGATCAGTTGG

ACTGAATCTCGAAGGGAATGGAGTGGCAACTGACGTCCCATCTGCAACTA

AAAGATGGGGCTTCAGGTCCGGTGTCCCACCAAAGGTGGTCAATTATGAA

GCTGGTGAATGGGCTGAAAACTGCTACAATCTTGAAATCAAAAAACCTGA

CGGGAGTGAGTGTCTACCAGCAGCGCCAGACGGGATTCGGGGCTTCCCCC

GGTGCCGGTATGTGCACAAAGTATCAGGAACGGGACCGTGTGCCGGAGAC

TTTGCCTTCCATAAAGAGGGTGCTTTCTTCCTGTATGATCGACTTGCTTC

CACAGTTATCTACCGAGGAACGACTTTCGCTGAAGGTGTCGTTGCATTTC

TGATACTGCCCCAAGCTAAGAAGGACTTCTTCAGCTCACACCCCTTGAGA

GAGCCGGTCAATGCAACGGAGGACCCGTCTAGTGGCTACTATTCTACCAC

AATTAGATATCAGGCTACCGGTTTTGGAACCAATGAGACAGAGTACTTGT

TCGAGGTTGACAATTTGACCTACGTCCAACTTGAATCAAGATTCACACCA

```
CAGTTTCTGCTCCAGCTGAATGAGACAATATATACAAGTGGGAAAAGGAG

CAATACCACGGGAAAACTAATTTGGAAGGTCAACCCCGAAATTGATACAA

CAATCGGGGAGTGGGCCTTCTGGGAAACTAAAAAAAACCTCACTAGAAAA

ATTCGCAGTGAAGAGTTGTCTTTCACAGTTGTATCAAACGGAGCCAAAAA

CATCAGTGGTCAGAGTCCGGCGCGAACTTCTTCCGACCCAGGGACCAACA

CAACAACTGAAGACCACAAAATCATGGCTTCAGAAAATTCCTCTGCAATG

GTTCAAGTGCACAGTCAAGGAAGGGAAGCTGCAGTGTCGCATCTAACAAC

CCTTGCCACAATCTCCACGAGTCCCCAATCCCTCACAACCAAACCAGGTC

CGGACAACAGCACCCATAATACACCCGTGTATAAACTTGACATCTCTGAG

GCAACTCAAGTTGAACAACATCACCGCAGAACAGACAACGACAGCACAGC

CTCCGACACTCCCTCTGCCACGACCGCAGCCGGACCCCCAAAAGCAGAGA

ACACCAACACGAGCAAGAGCACTGACTTCCTGGACCCCGCCACCACAACA

AGTCCCCAAAACCACAGCGAGACCGCTGGCAACAACAACACTCATCACCA

AGATACCGGAGAAGAGAGTGCCAGCAGCGGGAAGCTAGGCTTAATTACCA

ATACTATTGCTGGAGTCGCAGGACTGATCACAGGCGGGAGAAGAACTCGA

AGAGAAGCAATTGTCAATGCTCAACCCAAATGCAACCCTAATTTACATTA

CTGGACTACTCAGGATGAAGGTGCTGCAATCGGACTGCCTGGATACCAT

ATTTCGGGCCAGCAGCCGAGGGAATTTACATAGAGGGGCTAATGCACAAT

CAAGATGGTTTAATCTGTGGGTTGAGACAGCTGGCCAACGAGACGACTCA

AGCTCTTCAACTGTTCCTGAGAGCCACAACTGAGCTACGCACCTTTTCAA

TCCTCAACCGTAAGGCAATTGATTTCTTGCTGCAGCGATGGGGCGGCACA

TGCCACATTCTGGGACCGGACTGCTGTATCGAACCACATGATTGGACCAA

GAACATAACAGACAAAATTGATCAGATTATTCATGATTTTGTTGATAAAA

CCCTTCCGGACCAGGGGGACAATGACAATTGGTGGACAGGATGGAGACAA

TGGATACCGGCAGGTATTGGAGTTACAGGCGTTATAATTGCAGTTATCGC

TTTATTCTGTATATGCAAATTTGTCTTTTAG
```

VSV-EBOV Glycoprotein Amino Acid Sequence (676 a.a.)

(SEQ ID NO: 7)
```
MGVTGILQLPRDRFKRTSFFLWVIILFQRTFSIPLGVIHNSTLQVSDVDK

LVCRDKLSSTNQLRSVGLNLEGNGVATDVPSATKRWCFRSCVPPKVVNYE

AGEWAENCYNLEIKKPDGSECLPAAPDGIRGFPRCRYVHKVSGTGPCAGD

FAFHKEGAFFLYDRLASTVIYRGTTFAEGVVAFLILPQAKKDFFSSHPLR

EPVNATEDPSSGYYSTTIRYQATGFGTNETEYLFEVDNLTYVQLESRFTP

QFLLQLNETIYTSGKRSNTTGKLTWKVNPEIDTTIGEWAFWETKKNLTRK

IRSEELSFTVVSNGAKNISGQSPARTSSDPGTNTTTEDHKIMASENSSAM

VQCHSQGREAAVSHLTTLATISTSPQSLTTKPGPDNSTHNTPVYKLDISE

ATQVEQHHRRTDNDSTASDTPSATTAAGPPKAENTNTSKSTDFLDPATTT

SPQNHSETAGNNNTHHQDTGEESASSGKLGLITNTIAGVAGLITGGRRTR

REAIVNAQPKCNPNLHYWTTQDEGAAIGLAWIPYFGPAAEGIYIEGLMHN

QDGLICGLRQLANETTQALQLFLRATTELRTFSILNRKAIDFLLQRWGGT

CHILGPDCCIEPHDWTKNITDKIDQIIHDFVDKTLPDQGDNDNWWTGWRQ

WIPAGIGVTGVIIAVIALFCICKFVF
```

VSV-1'GFP-EBOV

The EBOV glycoprotein sequence expressed in VSV-1'GFP-EBOV is derived from the Mayinga strain of Zaire Ebola virus as described in the methods of Wong, et al. (2010) *J. Virol* 84: 163-175. The nucleotide sequence shown below was determined by direct sequencing of VSV-1'GFP-EBOV samples and is similar (but not identical) to the sequence for the full-length (non-secreted) glycoprotein gene found in GenBank accession AF086833 nt 6039-8068. The mucin domain (a.a. 309-489) has been deleted from the protein and two amino acids are different (N40S and I662V) relative to the GenBank sequence. Whereas the mucin deletion and I662V mutations were intentionally introduced and are described in the methods of Wong, et al. (2010), the N40S mutation was not described and it is unknown whether this mutation existed within the original recombinant plasmid used to generate the virus or emerged after recovery through repeated passages.

VSV-1'GFP-EBOV Glycoprotein Gene Nucleotide Sequence (1494 nt)

(SEQ ID NO: 8)
```
ATGGGCGTTACAGGAATATTGCAGTTACCTCGTGATCGATTCAAGAGGAC

ATCATTCTTTCTTTGGGTAATTATCCTTTTCCAAAGAACATTTTCCATCC

CACTTGGAGTCATCCACAGTAGCACATTACAGGTTAGTGATGTCGACAAA

CTAGTTTGTCGTGACAAACTGTCATCCACAAATCAATTGAGATCAGTTGG

ACTGAATCTCGAAGGGAATGGAGTGGCAACTGACGTGCCATCTGCAACTA

AAAGATGGGGCTTCAGGTCCGGTGTCCCACCAAAGGTGGTCAATTATGAA

GCTGGTGAATGGGCTGAAAACTGCTACAATCTTGAAATCAAAAAACCTGA

CGGGAGTGAGTGTCTACCAGCAGCGCCAGACGGGATTCGGGGCTTCCCCC

GGTGCCGGTATGTGCACAAAGTATCAGGAACGGGACCGTGTGCCGGAGAC

TTTGCCTTCCATAAAGAGGGTGCTTTCTTCCTGTATGATCGACTTGCTTC

CACAGTTATCTACCGAGGAACGACTTTCGCTGAAGGTGTCGTTGCATTTC

TGATACTGCCCCAAGCTAAGAAGGACTTCTTCAGCTCACACCCCTTGAGA

GAGCCGGTCAATGCAACGGAGGACCCGTCTAGTGGCTACTATTCTACCAC

AATTAGATATCAGGCTACCGGTTTTGGAACCAATGAGACAGAGTACTTGT

TCGAGGTTGACAATTTGACCTACGTCCAACTTGAATCAAGATTCACACCA

CAGTTTCTGCTCCAGCTGAATGAGACAATATATACAAGTGGGAAAAGGAG

CAATACCACGGGAAAACTAATTTGGAAGGTCAACCCCGAAATTGATACAA

CAATCGGGGAGTGGGCCTTCTGGGAAACTAAAAAAAACCTCACTAGAAAA

ATTCGCAGTGAAGAGTTGTCTTTCTCTAGAGCAGGACTGATCACAGGCGG

GAGAAGAACTCGAAGAGAAGCAATTGTCAATGCTCAACCCAAATGCAACC

CTAATTTACATTACTGGACTACTCAGGATGAAGGTGCTGCAATCGGACTG

GCCTGGATACCATATTTCGGGCCAGCAGCCGAGGGAATTTACATAGAGGG

GCTAATGCACAATCAAGATGGTTTAATCTGTGGGTTGAGACACCTGGCCA
```

```
                                              -continued
ACGAGACGACTCAAGCTCTTCAACTGTTCCTGAGAGCCACAACTGAGCTA

CGCACCTTTTCAATCCTCAACCGTAAGGCAATTGATTTCTTGCTGCAGCG

ATGGGGCGOCACATGCCACATTCTGGGACCGGACTGCTGTATCGAACCAC

ATGATTGGACCAAGAACATAACAGACAAAATTGATCAGATTATTCATGAT

TTTGTTGATAAAACCCTTCCGGACCAGGGGGACAATGACAATTGGTGGAC

AGGATGGAGACAATGGATACCGGCAGGTATTGGAGTTACAGGCGTTGTAA

TTGCAGTTATCGCTTTATTCTGTATATCCAAATTTGTCTTTTAG
```

VSV-1'GFP-EBOV Glycoprotein Amino Acid Sequence (497 a.a.)

```
                                                (SEQ ID NO: 9)
MGVTGILQLPRDRFKRTSFFLWVIILFQRTFSIPLGVIHSSTLQVSDVDK

LVCRDKLSSTNQLRSVGLNLEGNGVATDVPSATKRWGFRSGVPPKVVNYE

AGEWAENCYNLEIKKPDGSECLPAAPDGIRGFPRCRYVHKVSGTGPCAGD

FAFHKEGAFFLYDRLASTVIYRGTTFAEGVVAFLILPQAKKDFFSSHPLR

EPVNATEDPSSGYYSTTIRYQATGFGTNETEYLFEVDNLTYVQLESRFTP

QFLLQLNETIYTSGKRSNTTGKLIWKVNPEIDTTIGEWAFWETKKNLTRK

IRSEELSFSRAGLITGGRRTRREAIVNAQPKCNPNLHYWTTQDEGAAIGL

AWIPYFGPAAEGIYIEGLMHNQDGLICGLRQLANETTQALQLFLRATTEL

RTFSILNRKAIDFLLQRWGGTCHILGPDCCIEPHDWTKNITDKIDQIIHD

FVDKTLPDQGDNDNWWTGWRQWIPAGIGVTGVVIAVIALFCICKFVF
```

VSV-LASV

The viral genome is a VSV background where the sequence encoding the VSV G protein is substituted for a sequence encoding the glycoprotein from Lassa virus, and a sequence encoding GFP is inserted into the first position of the viral genome. The LASV glycoprotein sequence expressed in VSV-LASV is derived from the Josiah strain of Lassa virus as described in the methods of Garbutt, et al. (2004) *J. Virol* 78: 5458-5465.

VSV-1'GFP-LASV

The LASV glycoprotein sequence expressed in VSV-1'GFP-LASV is derived from the Josiah strain of Lassa virus as described in the methods of Jae, et al. (2013) *Science* 340: 479-483.

Viral infection was detected by the GFP reporter, using fluorescent and phase contrast imaging under a microscope. All viruses were used at an MOI of 0.1; thus Lassa-VSV replicated in gliomas in order to infect all cells tested.

For in vitro experiments, viruses were propagated on Vero cells, purified, and concentrated using sucrose gradient centrifugation (Cureton, et al., *PLoS Pathog*, 6, e1001127 (2010). For in vivo experiments, viruses were propagated on Vero cells and filter-purified according to a protocol described previously (Lawson, et al., *Proc. Natl. Acad. Sci. USA*, 92:4477-4481 (1995). All viruses were plaque-titered on Vero cells prior to experiments. Human glioma U87 and U118 were obtained from ATCC (Manassas, Va.), mouse glioma CT2A was a gift from Dr T Seyfried (Boston College, Chestnut Hill, Mass.), human melanoma YUMAC and normal human melanocytes were provided by Yale SPORE in Skin Cancer. Normal human glial cells were derived from human temporal lobectomies (Ozduman, et al., *J. Neurosci*, 28:1882-1893 (2008)). Normal human dermal fibroblasts were purchased from Cambrex (Walkersville, Md.). Normal human embryonic neurons were purchased from Sciencell (Carlsbad, Calif.). The human cancer cell lines SJSA-1, BT-549, T-47D, HCT116, SW480, T24, and RT4, and DU-145 lines were kindly provided. Stably transfected tumor cells expressing red fluorescent protein RFP (rU87 and rYUMAC) were generated as described earlier (Wollmann, et al., *J. Virol.*, 87:6644-6659 (2013)).

Primary cultures of mouse brain were generated by dissociating cortex of E17 mice for predominantly neuronal cultures and whole brain tissue of P1 mice for mixed neuronal/glia cultures. Cells were plated in MEM (Invitrogen, Carlsbad, Calif.) supplemented with 10% FBS overnight before medium was replaced with Neurobasal/B27 medium (Invitrogen). Melanoma cells were maintained in Opti-MEM/5% FBS, melanocyte medium containing additional supplements listed elsewhere (Wollmann, et al., *J. Virol.*, 87:6644-6659 (2013)). Glioma cells, human glia and fibroblasts were maintained in MEM/10% FBS (Invitrogen). All cultures were kept in humidified atmosphere containing 5% $CO_2$ at 37° C.

In Vitro Experiments

Viral infection of mixed neuronal/glial cultures, and U87, U118, CT2A, and YUMAC tumor cultures was monitored by quantifying GFP expression of infected cells compared to total number of cells on at least 10 microscopic fields using fluorescence microscopy. Cultures were assessed for presence of cytopathic effects before and after virus application. Cytopathic effects were noted as the appearance of rounding, blebbing and syncitia formation. For analysis of infection characteristic of chimeric VSVs on mixed neuronal cultures, morphology of infected cells was used as a guide for identifying neuronal or glia infection by the virus. Identification of cell type was later corroborated by immunohistochemistry for NeuN and GFAP. Mixed human brain cultures were established by first plating a glia monolayer. Two days later, human neurons were seeded onto the glia monolayer. After 7 days in culture and morphological confirmation of neuron process outgrowth, cultures were inoculated with VSV-wtG or VSVLASV-G (MOI 1). GFP expression was quantified 24 hours later.

Plaque assay was used to assess viral replication. In short, cells were infected at an MOI of 0.1, residual virus was removed by replacing supernatant, and progeny virus was collected from the supernatant at the indicated time points. Serial dilutions were plated on monolayers of Vero or BHK cells, respectively. 2.5% Agar solution in MEM was used as semi-solid overlay. For IFN pretreatment, cultures were incubated for 8 hours with recombinant hybrid interferon type 1 IFNαA/D (Sigma-Aldrich; catalog no. I4401) at a concentration of 100 IU/ml. To test generalization of the oncolytic effect of VSV-LASV-G to other human cancer types, 8 human tumor cell types were infected at an MOI 3 (primary inoculation). 2 hours later inoculum was removed and cultures were washed 3 times with PBS before addition of fresh medium. 24 hours later infection rates were determined by GFP expression. To assess the capability of VSV-LASV-G to propagate in these tumor cultures the 24 hpi supernatant was filtered to remove cellular debris and transferred onto an uninfected monolayer of the same tumor designation (secondary inoculation).

Image Analysis

Virus infected cultures and histological sections of mouse brain were analyzed using a fluorescence microscope (IX 71, Olympus Optical, Tokyo, Japan). A fluorescence stereomicroscope (SZX12, Olympus Optical) was used for whole brain scanning before sectioning.

Results

Figures 1A, 1B, 1C:
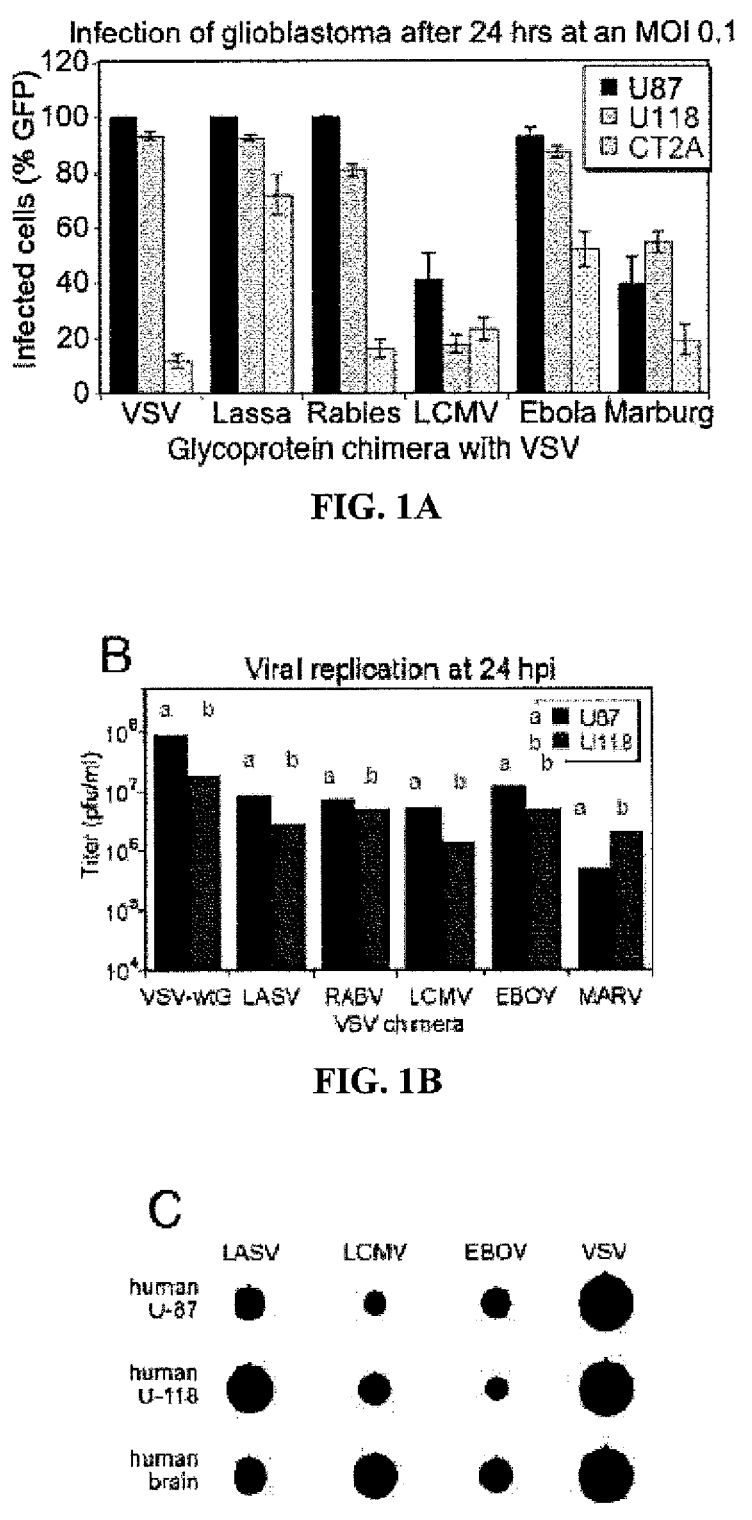

To test the efficacy of different binding glycoproteins, 6 recombinant VSVs were compared, each expressing a different binding glycoprotein (FIGS. 1A-1C). Five chimeric VSVs were tested in which the VSV glycoprotein was replaced (Beier, et al., Proc. Natl. Acad. Sci. USA, 108: 15414-15419 (2011); Jae, et al., Science, 340:479-483 (2013); Krishnan, et al., Viruses, 4:2471-2484 (2012)) by the G genes from other viruses, including Lassa fever, rabies, lymphocytic choriomeningitis, Ebola, or Marburg virus. These chimeric viruses were compared with control VSVs that retained the normal VSV glycoprotein. Chimeric viruses, which like VSV-wtG, also encoded GFP in the first genomic position, were tested first in human and mouse glioblastoma (GBM). All six viruses infected GBM cells in vitro FIG. 1A), with a greater level of infection of human GBM (U87 and U118) than mouse GBM (CT2A) 24 hpi (FIG. 1A). Generally speaking, Lassa-VSV showed the most robust infection of the 3 gliomas tested (U87, U118, CT2A) at 24 hrs, and earlier, while other viruses also infected some of the gliomas, but not all of them. Specifically, in U87 glioma, all viruses showed good infection except VSV-MARV (FIG. 1A). In U118 glioma, VSV-LASV, VSV-EBOV, and VSV-RABV showed high levels of infection, whereas VSV-MARV and VSV-LCMV significantly less. In mouse CT-2A glioma, VSV-LASV performed the best; VSV-EBOV infected almost as well as VSV-LASV (FIG. 1A). Lassa-VSV (VSV-La-G) infected and killed 100% of two human gliomas, U87 and U118.

All six viruses replicated on human GBMs, as seen at 24 hrs post inoculation (hpi) (FIG. 1B). Typical of VSV-infected cells (Ozduman, et al., J. Neurosci, 28:1882-1893 (2008); Wollmann, et al., J. Virol, 81:1479-1491 (2007)), infected cells died, as confirmed by staining with membrane impermeant dyes.

The relative infection of all six viruses on mouse and human brain cultures that included neurons and glia was also tested. The relative infection of mouse neurons vs glia is shown in FIG. 1D. VSV-wtG showed the greatest level of neuronal infection (around 90%). VSV-LASV-G and VSV-LCMV-G showed the least neuronal infection. When plaque size was examined as a measure of infectivity and replication, VSV-LASV plaques were bigger than VSV-LCMV and VSV-EBOV on human gliomas U87 and U118 (FIG. 1C), indicating enhanced infection and replication. VSV generated the largest plaques on tumor cells, but also showed large plaques on normal brain cells, an unwanted phenotype. Among the chimeric viruses, VSV-LASV and VSV-EBOV generated smaller plaques on human brain than VSV-wtG and VSV-LCMV (FIG. 1C), and showed much weaker infection of pure human neuronal cultures than VSV-wtG (FIG. 3A).

Lassa-VSV, which was the superior oncolytic candidate from an analysis of glycoproteins from 5 unrelated viruses that were incorporated into the VSV genome, was also compared with other VSVs that expressed the normal VSV glycoprotein. Of 39 potential oncolytic viruses, including 17 variants of VSV, (Wollmann, et al., J Virol., 79: 6005-6022 (2005); Wollmann, et al., J. Virol., 81:1479-1491 (2007); Wollmann, et al., J. Virol., 84:1563-73 (2010); Wollmann, et al., Cancer J., 18:69-81 (2012); Paglino, et al., J. Virol., 85:9346-58 (2011); Ozduman, et al., J. Virology, 83:11540-11549 (2009); Ozduman, et al., J. Neurosci., 28:1882-1893 (2008)), Lassa-VSV was identified as a superior candidate in terms of a strong safety profile, as well as an effective potential to selectively target and kill GBMs and to precipitate an immune attack on the glioma.

Together, the in vitro data point to VSV-LASV as having the best combination of glioma infectivity (FIGS. 1A and 1C) and low neuronal tropism (FIG. 1D). VSV-EBOV was selected as a second candidate to include for in vivo testing being another virus with broad glioma tropism and evidence of reduced neurotropsim compared to VSVwtG in both mouse and human brain, although not as reduced as VSV-LASV. VSV-Lassa showed the least infection of neurons, coupled with a strong infection of human glioma. In contrast, a control rabies-VSV chimeric virus showed strong infection of neurons and would be a relatively very poor candidate for glioma treatment. Recombinant VSVs with minor changes to the genome, for instance VSV-M51, can potentially revert to the more aggressive wild type virus by gene mutation. In contrast, since the entire binding of VSV to cells has been switched to Lassa glycoprotein, and the VSV glycoprotein gene is deleted, this virus cannot revert to the wild type VSV, a substantial benefit. A primary mechanism of targeting is the absence or attenuation of the intrinsic anti-viral response in the majority of cancer cells, including gliomas, compared to normal cells that have an intrinsic interferon mediated antiviral response to VSV and other viruses (Stojdl, et al., Nat. Med., 6:821-825 (2000); Stojdl, et al., Cancer Cell., 4:263-275 (2003); Wollmann, et al., J. Virol., 81:1479-1491 (2007)).

Furthermore, although there is not full agreement as to the origin of cancer stem cells, with some indications that the cells initiate cancer, or that they arise from multiple mutations in dividing tumor cells, there is more agreement that cells that express antigens typical of stem cells do show resistance to small-molecule cancer therapeutics, and to radiation treatment. Glioma stem cells are reported to express CD133 and nestin. In preliminary experiments, using cells expressing CD133, Lassa-VSV was found to infect and kill these stem-like cells in culture, indicating another potential attribute of the use of this virus in the treatment of cancer.

Example 2

Lassa-VSV is Safe in the Brain

Materials and Methods
Mouse Procedures 6-8 week old male Swiss Webster mice received the following virus doses: I.C.: $3.6 \times 10^4$ pfu in 1 ml into the right striatum (2 mm lateral, 0.5 mm rostral to Bregma at 3 mm depth), I.V.: $10^6$ pfu in 100 µl via tail vein injection, I.N.: $2.5 \times 10^5$ pfu in 25 µl in each nostril. Stereotactic application of virus or tumor cells was performed under full anesthesia using ketamine/xylazine (100 and 10 mg/kg, respectively) applied via i.p. route. Uni- and bilateral intracranial glioma and melanoma xenografts were established in 4-6 week old male CB17 SCID mice by injection of $5 \times 10^4$ cells each into the left and right striatum (Ozduman, et al., J. Neurosci, 28:1882-1893 (2008); Wollmann, et al., J. Virol, 87:6644-6659 (2013)). 15 days post tumor placement mice received virus either via a unilateral intratumoral injection ($3.6 \times 10^4$ pfu in 1 µl) or via tail vein injection ($10^6$ pfu in 100 µl). Mice were monitored daily and sacrificed if one of the following conditions were observed: A) weight loss of 25% or more, B) immobility, C) occurrence of adverse neurological symptoms, or D) reaching the end of the observation period of the survival study.

For histologic analysis of early states of viral infection mice were sacrificed at 2 or 8 days post viral inoculation. After overdose with anesthetic, mice were transcardially perfused with 4% paraformaldehyde. Brains were harvested and stored in 4% paraformaldehyde, dehydrated in 30% sucrose solution and cut in 20 to 30 μm coronal sections with a cryostat. For detection of live virus in designated mice after short (2 days) and long (>60 days) exposure to VSV-LASV-G, tissue samples were collected under sterile conditions from brain, lung, blood, and liver after euthanasia. Tissues were mechanically homogenized in PBS using a microcentrifuge tube tissue grinder. Part of the resultant tissue suspension was plated onto BHK monolayers and assessed for presence of GFP positive cells 24 hours later. To test the capability of VSV-LASV-G to induce antibody production, adult Swiss Webster mice received an intranasal and intramuscular primary VSV-LASV-G inoculation (at concentrations listed above) followed by a boost 4 weeks later. 2 weeks later, mice were euthanized, bled, and serum was collected. Antibody containing serum was diluted 1:50 to 1:10,000.

Brain sections from transgenic mice expressing GFP in hypocretin neurons were used to target GFP. Brain sections of IFNα/β-R knock-out mice infected with VSV-LASV-G were used to target VSV-LASV-G expression. rU87 and rYUMAC cells were tested for pathogens before tumor grafting and found to be pathogen free. All animal experiments adhered to institutional guidelines and were approved by the Yale University Animal Care and Use Committee.

Rat Procedures

Safety of intracranial VSV-LASV-G in rats was tested. Stereotactic coordinates and applied virus dose equaled those in rat tumor models described in the following. Syngeneic brain tumor models were established via stereotactic injection of 50,000 cells in 3 μl suspension into the right striatum (0.7 mm rostral of Bregma, 3.5 mm lateral, 5 mm deep) of 7-8 week old Lewis rats (rat CNS-1 glioma). 7 days post tumor placement, rats received a single intracranial injection of 3 μl suspension containing $1.2 \times 10^5$ PFU of VSV-LASV-G into the area of the tumor. Rats were euthanized at 3 dpi and brains harvested.

Intrcranial Injection Safety Assays

The Lassa-VSV and Ebola-VSV viruses were injected directly into the brains of 6 week old Swiss-Webster mice (n=10 mice for each virus) using stereotactic injection procedures. A Hamilton syringe controlled by a Stoelting stereotactic injector (Stoelting, Wood Dale, Ill.) was used to inject 1 μl of virus solution into the striatum (2 mm lateral, 0.4 mm rostral to bregma, at 3 mrn depth). As a control, attenuated VSV-1'GFP and attenuated VSV-M51 viruses were injected directly into the brains of mice (n=6 mice for each virus) using the same procedure. All injections were $3.6 \times 10^4$ pfu in 1 μl. Animals were monitored daily for body weight, grooming, and overall health. Mice were euthanized with a pentobarbital overdose when neurological symptoms were detected or when body weight dropped below 75%.

Statistical Analysis

Statistical significance was determined by Student's t-test, ANOVA, and Chi-Square test. P-values<0.05 were considered statistically significant. Survival studies were non-blinded. Mice were allocated to experimental or control group based on cage number. Power analysis was employed to determine group size for survival experiments of tumor-bearing mice and of virus injected mice.

Results

To corroborate further the relative lack of infection of neurons of the chimeric viruses, VSV-LASV and VSV-EBOV were compared to two VSVs that expressed the VSV glycoprotein in vivo; one of the VSVs was further attenuated by including an M51 mutation which enhances the antiviral innate immune response against the virus (Waibler et al, 2007). Injection of either VSV with normal wild-type G (VSV-wtG) into the normal brain generated lethal consequences, with a median survival of 3.5 days for VSV-wtG (n=6) and 8 days for the attenuated strain VSV-M51 (n=6) (FIG. 2A) consistent with previous observations (Ozduman et al., 2009). This underlines the neurotoxicity of VSV with normal VSV-G protein, even when attenuated. In striking contrast, direct injections of VSV-LASV-G or VSV-EBOV-G, ($3.6 \times 10^4$ pfu in 1 μl) into normal mouse brains exerted no adverse effect in >112 days (n=8 each virus; p<0.001; Chi square test) (FIG. 2A).

In another experiment VSV-LASV-G was compared with VSV-IFN, an IFN-expressing virus modeled after one (Obuchi, et al., *J. Virol.*, 77:8843-8856 (2003) currently in clinical trials for the treatment of liver cancer (NCT01628640). All mice (n=9) receiving intracranial VSV-IFN died within 12 days consistent with reports of this virus infecting brain meninges (Yarde, et al., *Cancer Gene Ther.*, 20:616-621 (2013); all mice that received VSV-LASV-G (n=4 here) survived with no adverse side effects (FIG. 2B). Similarly, VSV-LASV-G injected into the rat brain also showed no sign of neurotoxicity (>80 days, n=3). No virus or infected cells were detected in the brain or elsewhere (liver, spleen, blood) by histological analysis or culture of inoculated mouse tissue at the conclusion of the experiment, indicating the total elimination of the virus. The injections of VSV-LASV-G and VSV-EBOV-G were viable, as euthanasia at 2 dpi revealed limited infection of glia within the brain. However, by 8 dpi, few or no infected cells could be found. VSV-LASV-G and VSV-EBOV-G were also injected intravenously (n=5 each), and an additional set of mice were inoculated at combined intranasal/intramuscular/subcutaneous (n=5, total $8 \times 10^6$ pfu VSV-LASV-G) sites; none of these mice showed signs of viral pathogenicity and no virus could be harvested from these mice 2 months postinoculation.

A different VSV-LASV-G that contained no GFP (Garbutt, et al., *J. Virol.*, 78:5458-5465 (2004) was also tested and found to have no adverse effect after injection into the mouse brain (n=5) and followed for 6 weeks, showing that the attenuation mediated by inclusion of the GFP gene in the first genomic position was not critical for CNS safety. The 100% survival of mice injected with VSV-LASV-G and VSV-EBOV-G correlated with a very low infectivity of these viruses in pure neuronal cultures, particularly when compared to VSV with the normal VSV G protein (FIG. 2A-2B).

The most problematic aspect of using VSV either as an oncolytic virus or as a vaccine vector against more dangerous viruses including Ebola (Garbutt, et al., *J. Virol.*, 78:5458-5465 (2004), HIV, and other pathogenic viruses, has been the concern about adverse effects of the virus in the brain (Ozduman, et al., *J. Virol.*, 83:11540-11549 (2009); Huneycutt, et al., *Brain Res.*, 635:81-95 (1994)). A number of previous studies have described the potential for VSV to selectively target and destroy many different types of tumors. However, a substantial problem with the use of VSV as an oncolytic virus, both outside and within the brain, has been the possibility of adverse effects within the brain potentially leading to motor dysfunction (Huneycutt, et al., *Brain Res.*, 635:81-95 (1994), behavioral disturbances (Lundh, et al., *J. Neuropathol. Exp. Neurol.*, 47:497-506 (1988) or death (Huneycutt, et al., *Brain Res.*, 635:81-95 (1994); van den Pol, et al., *J. Virol*, 76:1309-1327 (2002). The data show that eliminating the native glycoprotein from the VSV genome and substituting binding glycoproteins from other viruses greatly reduces infection and cytolysis of neurons. All five chimeric VSVs tested showed considerably reduced neuron tropism and replication compared with the natural VSV glycoprotein. Not only were the chimeric viruses tested safe within the brain, but direct injection of VSV-LASV-G into the brains of SCID mice lacking the noniial complement of B and T immune cells generated no adverse effect, and the innate immune system within the brain eliminated the virus.

Importantly, after intravenous inoculation, the chimeric viruses VSV-LASV-G and VSV-EBOV-G were able to cross the blood brain barrier and selectively infect brain tumors with little or no infection of normal neurons or glia, and no adverse effects. VSV-LASV-G completely eliminated brain tumors and prolonged the lives of tumor-bearing mice indefinitely. VSV containing the Ebola glycoprotein also crossed the blood brain barrier and targeted the brain tumor, but showed only partial infection of the glioma.

VSV neurotoxicity can be reduced by generating peripheral immunity in advance of intracerebral inoculation (Ozduman, et al., *J. Virol.*, 83:11540-11549 (2009) or by administering exogenous type 1 interferon, or via intra cerebral viral vectors that generate interferon (Wollmann, et al., *Virology, in press.* (2014). Attenuated VSVs have been constructed by a number of molecular alterations, including reduction of cytoplasmic amino acids in the G protein, mutations in the M gene particularly at M51, adding genes upstream of viral genes (Roberts, et al., *J. Virol.*, 73:3723-3732 (1999); Ahmed, et al., *Virology*, 33:34-39 (2004); Ramsburg, et al., *J. Virol.*, 79:15043-15053 (2005)), but most of these resultant VSVs still retain negative side effects in the brain due to neuronal infection. Even a VSV currently in clinical tests that expresses interferon (VSV-IFN), although attenuated, is problematic and can be lethal if it gains access to the brain. None of these recombinant strategies directly eliminate the lethal neurotropism of the virus within the brain conferred by the VSV-G protein. In contrast, all five G protein chimeric viruses used in the disclosed studies showed reduced neuron infection, and the two tested in vivo showed complete safety within the brain. Even substitution of the glycoprotein from rabies, a virus with well-known neuronal targeting, although it still showed an unacceptably high neuron targeting, still showed reduced infection of neurons compared with the VSV glycoprotein, and has been shown relatively safe in the brain (Beier, et al., *Proc. Natl. Acad. Sci. USA*, 108:15414-15419 (2011), underlining the importance of eliminating the VSV glycoprotein.

Neither VSV-EBOV-G nor VSV-LASV-G injected intracerebrally into normal mice, immunocompromised SCID mice, or rats evoked any adverse action, whereas similar concentrations of other VSVs with the native G, including attenuated VSV-CT9-M51 (Wollmann, et al., *Virology, in press.* (2014), VSV-1' GFP, VSVmIFNα, and VSV-M51 (FIG. 2A-2B) were lethal.

This safety is also corroborated with previous studies that have used similar virus recombinants with Lassa (or Ebola) glycoproteins in place of the VSV G-protein as immunization vehicles to protect against wild-type Lassa or Ebola viruses; and deletion of genes other that the glycoprotein gene eliminates the toxicity and disease potential associated with wild type Ebola and Lassa. Lassa and Ebola virus may have arisen from a common ancestor virus (Gallaher, et al., *BMC Microbial.*, 1:1, 6 pages, (2001)). VSV-LASV-G was previously shown safe in rodents after intraperitoneal injection, but intracranial safety was not investigated (Garbutt, et al., *J. Virol.*, 78:5458-5465 (2004). One human has been injected with Ebola-VSV as a vaccine after a lab accident, with no adverse consequence (Günther, et al., *J. Infect. Dis.*, 204 Suppl 3:S785-S790 (2011)). The results disclosed herein show that both VSV-LASV-G and VSV-EBOV-G are safe in the rodent brain. The GFP reporter gene in both VSV-LASV-G and VSV-wtG provides some attenuation to both viruses by reducing expression of other VSV genes; in spite of this, VSV with the wild type glycoprotein was still lethal within the brain even when carrying the attenuating GFP gene, whereas VSV-LASV-G and -EBOV-G were safe in the brain indicating that safety in the brain is due to the absence of the neurotoxic VSV glycoprotein. This view is supported by the data showing safety of VSV-LASV in chimeric viruses not containing the GFP gene. The lack of VSV-LASV-G infection of neurons in the rodent brain parallels the in vitro studies with human neurons showing a lack of infection, and indicating that the virus may also be safe in the human brain. This is consistent with the findings which did not consider the oncolytic potential, but did show that these chimeric viruses evoked a strong humoral and cellular immune response, and importantly, evoked no adverse health consequences, even when injected directly into the brains of rodents or non-human primates (Geisbert, et al., *PLoS Med*, 2:e183 (2005); Geisbert, et al., *PLoS Pathog.*, 4:e1000225 (2008); Geisbert, et al., *J. Virol.*, 83(14):7296-7304 (2009); Mire, et al., *PLoS Negl. Trop Dis*, 6:e1567 (2012)). Initiation of a strong immune response is another benefit, and can generate a secondary immune attack on the brain tumor.

Such strong attenuation of virus infection on normal cells might also lead to lack of efficiency in tumor destruction. Lassa-VSV was nonetheless capable of selectively infecting and killing GBM cells in vitro and in the mouse brain after intravenous or intracerebral virus administration, and substantially prolonged cancer survival far beyond that of control tumor-bearing mice that received no virus. In fact, at the time when all tumor bearing control mice had died from the expanding brain tumor, none of the mice in which tumors were treated with VSV-Lassa showed any obvious symptoms from the tumor, or from the virus.

In conclusion, other VSVs, even those attenuated, can lead to adverse neurological consequences or death. In contrast, Lassa-VSV shows no detectable adverse effects when injected directly into the brain.

Example 3

IFN Has Little Effect in Attenuating Infection of Gliomas by VSV-LASV-G

Materials and Methods

Quantitative RT-PCR

Mouse neuronal cultures and human U87 glioma cells were cultured in 6-well plates. VSV-LASV-G or VSV-wtG was added at an MOI of 1 and cultures were incubated for 20 minutes at 4° C. to test virus binding or for 30 minutes at 37° C. to test virus binding+internalization, respectively, as described elsewhere (Ozduman et al, 2008). Experiments were performed in duplicate. Cells were washed five times with PBS prior to RNA isolation using TRIzol Reagent (Invitrogen, Carlsbad, Calif.). Stratascript reverse transcriptase kit (Stratagene) was used for cDNA generation. TaqMan gene expression assays (Applied Biosystems, Foster City, Calif.) were used to quantify the expression of β-actin and VSV genomes using an ICycler iQ Real time PCR system (Bio-Rad, Hercules, Calif.). For specific VSV genome detection (excluding viral mRNA) primers were designed to yield a product that spanned the junction between N and P genes. PCR samples were measured in triplicates, normalized to β-actin expression and compared to expression of VSVLASV-G binding to neurons as reference (ΔΔCt method).

Results

The results described herein show that the identity of the G protein has a profound effect on neuronal toxicity in the context of chimeric VSV, with viruses bearing LASV-G or LCMV-G being the least neurotropic. To elucidate mechanisms whereby the chimeric viruses appeared to show strong infection of glioma, but less infection of normal neurons and glia, the innate immune response was examined. In contrast to the protective effect of IFN on cultures of normal human neurons, glia, or fibroblasts, microscopy reveled that IFN had little effect in attenuating infection by VSV-LASV-G of U118 and U87 human gliomas, as virtually all glioma cells were infected and GFP-positive by 24 hours post-inoculation (FIG. 3A).

These data are consistent with the view that a primary mechanism underlying the selective VSV-LASV-G infection of cancer cells over normal glia is related to deficiencies in innate immunity. The lack of protection by added IFN points to a deficient IFN response among VSV-LASV-G susceptible tumors, similar to the mechanism described for the enhanced relative susceptibility of a number of tumor types to native VSV and to several other viruses including Newcastle disease virus, reovirus and myxoma virus (Phuangsab, et al., *Cancer Lett.*, 172:27-36 (2001); Strong, et al., *EMBO J.*, 17:3351-3362 (1998); Wang, et al., *Nature Immunol.*, 5:1266-1274 (2004)). The observation that normal brain cells in SCID mice which are deficient in T- and B-cell antiviral defenses showed little infection and no adverse effects from VSV-LASV-G in the brain further supports the view that an innate immune mechanism is protective of normal brain cells.

To test whether the intrinsic IFN system is important for the resistance of the brain to VSV-LASV-G, VSV-LASV-G was injected into the brains of mice (n=5) lacking the type I IFN receptor. Although IFNα/β-R−/− mice with intracerebral infection from VSV-LASV-G survived longer than those with VSV-wtG (n=3) (FIG. 3B), all these mice ultimately died within a week of CNS inoculation. These data support the view that an innate IFN-mediated immune response is important for both short and long term survival after VSV-LASV-G infection of the brain.

Figure 3C:
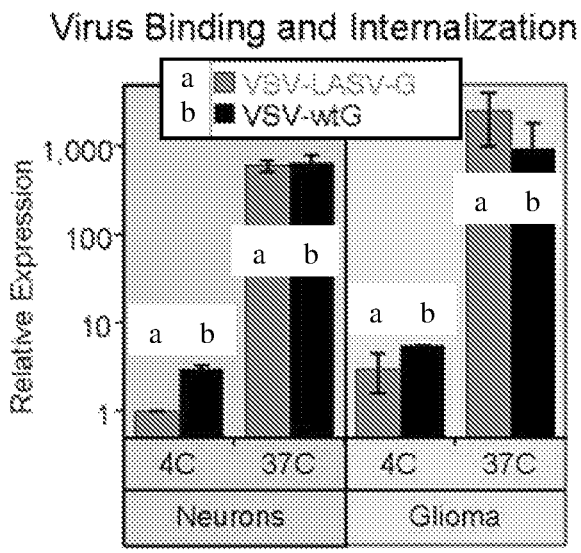
FIG. 3C is a histogram showing virus binding and internalization (relative expression by qRT-PCR) of VSV-wtG and Lassa-VSV in neurons and giloma cells at 4° C. and 37° C.

This motivated a comparison of binding of VSV-wtG and VSV-LASV-G to glioma and neurons. As judged by quantitative RT-PCR, both viruses bound similarly well to glioma cells and to neurons at 4° C. (FIG. 3C), a temperature at which endocytosis is inhibited. At 37° C., approximately 2-logs more virus becomes cell-associated than at 4° C., indicating effective and similar rates of internalization in both cell types and for both viruses.

Figure 3D:
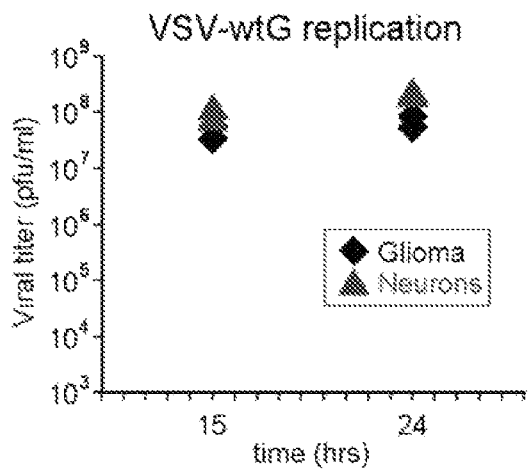
FIG. 3D is a dot plot showing the quantification of VSV-wtG viral replication in neurons (▲) and U87 glioma (♦) cells assessed by plaque assay at 15 and 24 hpi.
Figure 3E:
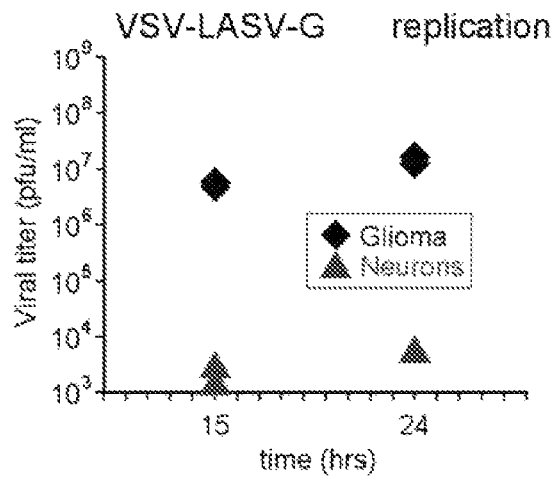
FIG. 3E is a dot plot showing the quantification of VSV-LASV-G viral replication in neurons (▲) and U87 glioma (♦) cells assessed by plaque assay at 15 and 24 hpi.

Next, the ability of infected glioma cells and neurons to generate progeny virions was examined. On gliomas, both VSV-wtG (FIG. 3D) and VSV-LASV-G (FIG. 3E) show substantial virus replication. In contrast, replication of VSV-LASV-G was greatly attenuated in neurons, by 4.5 logs relative to VSV-wtG which showed robust replication in neuron cultures (FIG. 3D-3E). Together, these data indicate that although both VSV-wtG and VSV-LASV-G bind to glioma cells and neurons, VSV-LASV-G replicates poorly in neurons. In neurons, a block to replication appears most likely to occur at the point of endosomal escape and uncoating, which is G-protein mediated, or possibly a subsequent step.

These data support a conclusion that the advantage of the Lassa virus glycoprotein is that it produces a selective block to replication in neurons but not in a wide variety of human tumors. This block to neuron infection appears not to be at the binding or internalization steps but at a step further downstream in the life cycle, possibly at the uncoating/endosomal escape step in neurons, given the importance of the glycoprotein to this process (Rigaut, et al., *J. Virol.*, 65:2622-2628 (1991).

Type 1 IFN is important to the selectivity and safety of VSV-LASV; mice lacking IFN receptor succumbed to virus inoculation. Previous reports indicate that whereas type 2 and 3 IFN may also contribute to immunity in the brain (van den Pol, et al., *J. Virol.*, 88:3695-3704 (2014), type 1 IFN is necessary for survival. The impairment of innate immunity characteristic of ontogenically transformed cells allows VSV-LASV to replicate rapidly, with cytolytic consequences for tumor cells. Addition of IFN to glioma had little to no effect on the infectivity of VSV-LASV, but provided additional protection to normal neurons and glia. The exquisite tumor-selectivity of VSV-LASV is thus a consequence of both reduced neurotropsism (via substitution of the Lassa G for the VSV G-protein) and virus susceptibility to IFN in normal cells; thus the virus is able to very selectively infect and destroy tumors whether entering from the blood stream into the brain, or crossing from an infected tumor to infect a distant locus of tumor cell growth in the contralateral brain, all without infecting the intervening healthy brain tissue. The fact that the innate immune system appears able to contain VSV-LASV-G indicates that the virus may prove safe to treat the increased incidence of cancers found in patients with compromised adaptive immune systems, for instance with AIDS.

Example 4

The Chimeric Virus Lassa-VSV Selectively Infects and Kills Glioma

Materials and Methods

Migration Assays

Red fluorescence marker RFP expressing tumor cells (U87 human glioblastoma cells and YUMAC human melanoma cells, respectively) were implanted into mice: two tumors per mouse—one in the left striatum, and a second in the right striatum.

14 days after tumor placement, Lassa-VSV expressing a green reporter gene GFP was then injected into the right tumor only.

Eight days later, mice were euthanized and perfused transcardially with 4% paraformaldehyde. Brains were harvested and analyzed for tumor expansion and virus infection using red and green fluorescence on a stereomicroscope for whole brain analysis and on an Olympus microscope for analysis of brain sections.

Results

Figure 4:
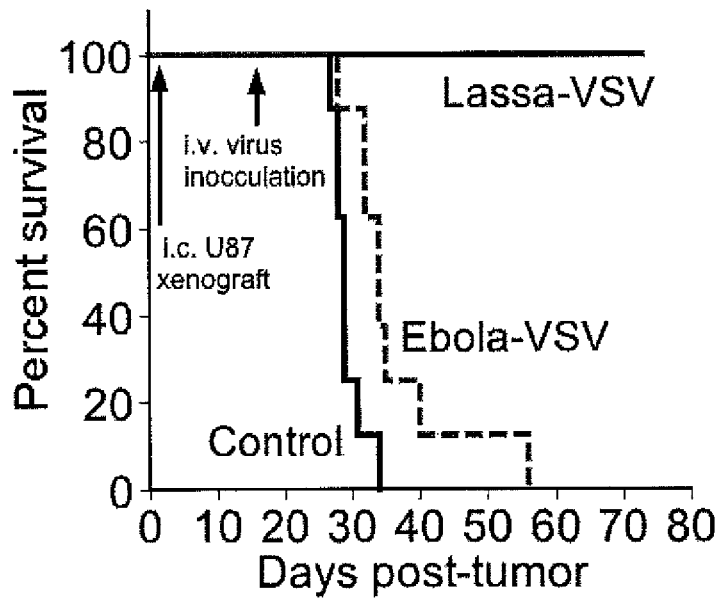
FIG. 4 is a Kaplan-Meier survival curve showing the % survival of mice infected with Lassa-VSV (solid line), and Ebola-VSV (dotted line) and uninfected control (solid line), respectively, over time (in days) following intracranial glioma xenograft and subsequent inoculation with virus. The times of i.c. U87 xenograft, and i.v. virus inoculation are indicated. The increased longevity of tumor bearing mice receiving Lassa-VSV is statistically significant (p<0.01; n=8 in each group).

The ability of chimeric virus to target and destroy brain tumors was also tested. Fifteen days after implant of red fluorescent human glioma into the SCID mouse brain, VSV-LASV-G ($10^6$ pfu in 100 ul) was injected intravenously (tail vein). This resulted in highly selective tumor infection and complete destruction of tumor cells within the brain. Mice with brain tumors survived only if treated with VSV-LASV-G, with no adverse effect as of 80 days (FIG. 4). Mice with tumors that did not receive virus all died from the tumor (median 29 day survival; n=8; FIG. 4). The chimeric virus VSV-EBOV-G also targeted brain tumors after intravenous inoculation (FIG. 4); VSV-EBOV-G extended life minimally (median survival 34 days; n=8) (FIG. 4).

Histological analysis showed large tumors in mice not treated with virus, and incomplete but selective infection of the tumor treated with VSV-EBOV-G. In contrast, few tumor cells if any were found following treatment with VSV-LASV-G, indicating highly selective infection and destruction of glioma.

In another short term experiment, mice showed near-complete infection of bilateral tumor masses 8 days post-inoculation, with little infection outside the tumor area indicating a rapid and selective VSV-LASV-G anti-tumor action (n=4).

Using a syngeneic rodent tumor model, the ability of VSV-LASV-G to infect rat glioma in immunocompetent rats was tested. VSV-LASV-G showed selective strong cytolytic infection of CNS-1 glioma tumors 3 days after intracerebral inoculation, with little detectable infection of normal brain, demonstrating the VSV-LASV-G selectively infects glioma not only in mice, but also in immunocompetent rats.

A major problem with gliomas is tumor cell migration within the brain. Thus skilled neurosurgeons can debulk the tumor, but cannot eliminate migrating cells or tumors that arise from migrating cells. To model this, human glioma were implanted in the left and right side of the SCID mouse brain with (in striatum). Fifteen days later VSV-LASV-G was stereotactically injected unilaterally, only into the tumor on the right side. Eight days later, the brains were examined. VSV-LASV-G had completely destroyed the inoculated tumor on the right side of the brain, and the virus had migrated to the contralateral left tumor and begun the process of infection and destruction without infecting the intervening normal brain. Accordingly, in addition to completely destroying the right tumor, Lassa-VSV migrated within the brain, and had begun to infect and kill the left tumor without detectable infection of noinial brain cells surrounding the tumors. Remarkably, VSV-LASV-G selectively destroyed the brain tumor with no adverse effects to the SCID mouse brain. These observations indicate that the virus was suppressed in the brain by a T- and B-cell-independent mechanism.

This is exactly the type of phenotype needed, that is, a virus that can infect multiple tumors in different CNS sites with no collateral damage to normal brain. Peripheral immunization has been shown to protect the brain from intracranial VSV (Ozduman, et al., *J. Virology*, 83:11540-11549 (2009)). Even without immunization, Lassa-VSV showed no neurotoxicity, whereas other VSVs did show intracranial neurotoxicity. Lassa-VSV was substantially more attenuated than the most attenuated VSV used (Ozduman, et al., *J. Virology*, 83:11540-11549 (2009); Wollmann, et al., *J. Virol*, 84:1563-73 (2010)), underlining its safety in the brain.

One potential limitation of VSVs with point and some other types of mutations (VSV-M51, VSV1'2'-GFP, and others) is that additional spontaneous mutations can cause the virus to revert back to a more aggressive wild type virus. That is unlikely in Lassa-VSV, as there is no mechanism whereby the Lassa-glycoprotein can mutate into the VSV glycoprotein, or where the VSV G-protein can be reconstituted, and also no way in which the non-glycoprotein genes of Lassa could appear in the recombinant virus.

Example 5

The Chimeric Virus Lassa-VSV Infects and Kills Melanoma

Next experiments were designed to determine if VSV-LASV-G is selective for gliomas, or is able to target other types of metastatic brain cancer. Melanomas are the deadliest form of skin cancer, and one of the chief problems is metastasis into the brain (Carlino, et al., *Cancer J.*, 18:208-212 (2012). Red fluorescent human melanoma was injected into the left and right side of the brain, similar to the glioma experiments described above. VSV-LASV-G was subsequently injected unilaterally into the right side melanoma. VSV-LASV-G not only caused complete destruction of the injected tumor mass, it also diffused across the brain midline, and showed strong infection of the non-injected contralateral melanoma, with no neuron infection in the intervening (SCID) brain.

Because VSV-LASV-G infected two unrelated brain tumor types, glioma and melanoma, it was also tested on other types of human cancer cells. VSV-LASV-G infected and replicated in colon, prostate, breast, bone, and bladder cancer cells, indicating its oncolytic potential was not restricted to glioma and melanoma brain tumors.

These results indicate that VSV-LASV-G is effective not only against glioma (which arise within the brain) but also against melanoma, a cancer that arises in the skin but metastasizes into the brain resulting in death within a few months of entering the brain. There is also a strong viral tropism for other types of human cancer cells including prostate, breast, colon, and bladder which can sometimes metastasize into the brain. The broad infectivity and cytolysis of multiple types of cancer cells indicate that VSV-LASV-G may also be effective in targeting other types of brain tumors not tested here, including meningioma, astrocytoma, ependymoma, and oligodendroglioma. The elimination of neurotropism by substitution of the Lassa glycoprotein for the VSV glycoprotein would provide an increased level of brain safety even if the virus were used to attack peripheral cancers.

In vitro testing indicates VSV-LASV had the best combination of reduced neurotropism and broad infectivity across different gliomas. VSV-EBOV also demonstrated broad glioma infectivity in vitro; although VSV-EBOV targeted tumors in the brain after intravenous application, the virus was not very effective in destroying the tumor. VSV-LCMV had a reduced neurotropism similar to VSV-LASV, but did not show as great or broad a potential for infectivity of gliomas, and formed smaller plaques than VSV-LASV in the human gliomas tested.

Example 6

VSV-LASV-G Evokes a Humoral Immune Response

To test whether VSV-LASV-G would evoke a humoral immune response, mice were inoculated intranasal and intramuscularly with this virus. VSV-LASV-G generated high titer antisera to VSV-LASV-G infected cells and also to the GFP transgene. Antisera with dilutions out to 1:10,000 generated positive immunostaining on GFP-expressing transgenic mice, indicating the potential for a secondary systemic immune response against VSV-LASV-G infected gliomas as reported for wildtype VSVs (Publicover, et al., *J. Viral.*, 78:9317-9324 (2004). It is interesting to note that chimeric VSV-LCMV/G was shown to be only weakly immunogenic with regard to generation of neutralizing antibodies against the virus (Muik, et al., *Cancer Res.*, 74:3567-3578 (2014). VSV-LASV-G appeared to completely eliminate human brain tumors in these experiments; VSVs also generated a strong immune response against tumors which could serve to augment tumor eradication in the event of incomplete direct tumor destruction (Wongthida, et al., *Hum. Gene Ther.*, 22:1343-1353 (2011). Chimeric VSVs that generate a strong immune response may also be beneficial in terms of evoking a strong secondary immune response against tumor related antigens.

VSV is a very promising vaccine platform, and even single inoculations generate strong cellular and humoral immunity (Publicover, et al, *J. Virol.*, 79:13231-13238 (2005); Buonocore, et al., *J. Virol.*, 76:6865-6872 (2002); Schell, et al., *J. Virol.*, 85:5764-5772 (2011)), but would advance further with the risk of neurotoxicity effectively eliminated, for example by substitution of the Lassa glycoprotein for the VSV glycoprotein. VSV-LASV-G may prove beneficial as a vaccine vector, given its potent immunogenicity. Immunogenic viral vectors could be generated against other pathogenic organisms by substituting a gene coding for a protein from the pathogenic microbe in place of the GFP gene within VSV-LASV-G; use of the Lassa glycoprotein in place of the VSV glycoprotein could provide a safer vector for immunization than wildtype VSV.

Example 7

The Chimeric Virus Lassa-VSV Protects From Glioma

Materials and Methods

Three groups of SCID mice received human glioma implants of similar size. 15 days later, one group received Lassa-VSV intravenously (tail vein), the second group received Ebola-VSV intravenously, and the third group served as a tumor-only control. Mice were monitored for changes in body weight. Mice showing body weight <75% of pre-tumor body weight were euthanized, as per animal use regulations.

Results

Figure 5:
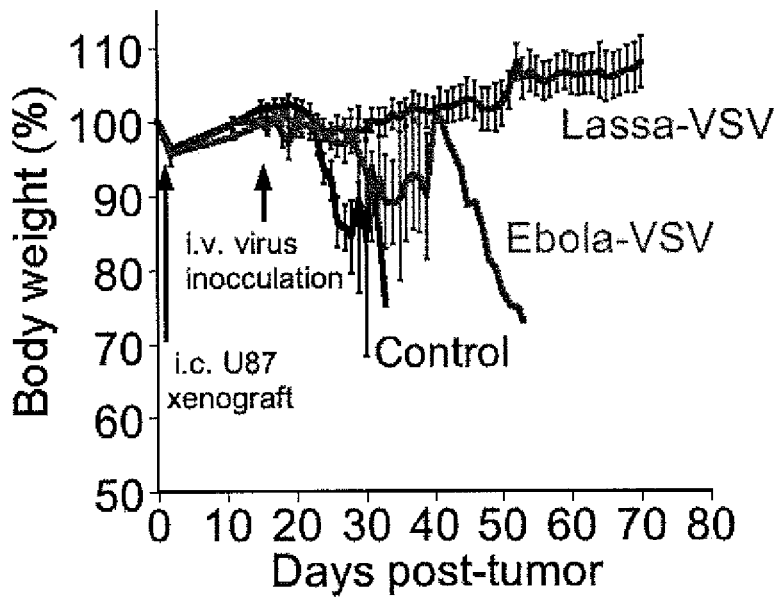
FIG. 5 is a line graph showing the % body weight of mice following intracranial glioma xenograft and subsequent systemic infection with Lassa-VSV, Ebola-VSV and uninfected control, respectively, over time (in days post-inoculation).

A mouse weight graph (FIG. 5) showed that mice receiving Lassa-VSV showed no strong reduction in body weight, whereas control mice with tumors show body weight reduction from the expanding tumors. Mice with tumors inoculated with Ebola-VSV (VSV-Eb-G) showed a reduced body weight from the expanding tumor. Lassa-VSV is safe in the brain, as mice maintained a normal body weight.

A mouse survival graph (FIG. 4) showed that Lassa-VSV protected mice from an implanted glioma. In contrast, control mice with the same tumor showed a median survival of 29 days post-glioma injection. All controls were dead by day 33 after tumor implant. The Ebola-VSV gave some protection against the tumor with a median survival of 34 days post-glioma implant, but ultimately, all were dead by 57 days after tumor implant. All mice treated with Lassa-VSV survived >43 days after Lassa-VSV inoculation, and >80 days after glioma implant. The increased longevity of tumor bearing mice receiving Lassa-VSV was statistically significant ($p<0.01$; $n=8$ in each group). Ultimately all controls died from the glioma. In striking contrast, Lassa-VSV crossed the blood brain barrier, infected and destroyed the tumor, and these mice all survived. Upon histological examination after euthanasia, large red gliomas were found in control mice, but were absent from Lassa-VSV-treated mice. Furthermore, since these SCID mice had severely attenuated systemic immune system (necessary for implantation of human glioma), but still survived peripheral and CNS infection with the virus, the chimeric Lassa-VSV is remarkably safe within the body, and particularly within the brain.

When injected into a brain tumor, Lassa-VSV kills tumor cells, and prolongs life with no detectable neurological consequences. When injected intravenously, the virus crosses the blood brain barrier and selectively infects gliomas

We claim:

1. A method of treating cancer comprising administering to a subject with cancer a pharmaceutical composition comprising an effective amount of a chimeric Vesicular stomatitis virus (VSV) to treat the cancer, wherein the chimeric VSV's genome comprises nucleic acid sequences encoding a VSV nucleoprotein (N), VSV phosphoprotein (P), VSV matrix (M) protein, VSV large (L) viral polymerase, and a heterologous glycoprotein derived from Ebola virus or Lassa virus comprising an amino acid sequence with at least 80% sequence identity to one of SEQ ID NOS: 2, 7 or 9.

2. The method of claim 1 wherein the N, P, M, and L proteins are each independently selected from a serotype or strain of VSV selected from VSV Indiana, VSV New Jersey, VSV Alagoas, VSV Cocal, VSV Chandipura, VSV Isfahan, VSV San Juan, VSV Orsay, and VSV Glasgow.

3. The method of claim 1, wherein the chimeric VSV's genome encodes one or more additional heterologous genes.

4. The method of claim 3, wherein the one or more additional heterologous genes encode a therapeutic protein, a reporter, a vaccine antigen, a targeting moiety, or a combination thereof.

5. The method of claim 1 wherein the cancer is selected from the group consisting of multiple myeloma bone, bladder, brain, breast, cervical, colo-rectal, esophageal, kidney, liver, lung, nasopharangeal, pancreatic, prostate, skin, stomach, and uterine.

6. The method of claim 5 wherein the brain cancer is oligodendroglioma, meningioma, supratentorial ependymona, pineal region tumors, medulloblastoma, cerebellar astrocytoma, infratentorial ependymona, brainstem glioma, schwannomas, pituitary tumors, craniopharyngioma, optic glioma, and astrocytoma.

7. The method of claim 5 wherein the brain cancer is glioblastoma.

8. The method of claim 1 wherein the virus is in a dosage of between $10^2$ and $10^{12}$ plaque-forming units (PFU).

9. The method of claim 1 wherein the pharmaceutical composition is administered locally to the site of the cancer.

10. The method of claim 1 wherein the pharmaceutical composition is administered systemically to the subject.

11. The method of claim 1 further comprising administering the subject a second therapeutic agent.

12. The method of claim 11 wherein the second therapeutic agent is an anticancer agent, a therapeutic protein, or an immunosuppressant.

13. The method of claim 1 wherein the chimeric VSV has little or no ability to infect normal or healthy neurons.

14. The method of claim 1, wherein the chimeric VSV's genome lacks a nucleic acid sequence encoding VSV glycoprotein (G).

15. The method of claim 1, wherein the heterologous glycoprotein comprises the amino acid sequence of SEQ ID NO:2.

16. The method of claim 1, wherein the heterologous glycoprotein is encoded by a nucleic acid sequence at least 80% identical to the segment of SEQ ID NO:1 that encodes SEQ ID NO:2, or a fragment thereof.

17. The method of claim 1, wherein the heterologous glycoprotein comprises the amino acid sequence of SEQ ID NO:7 or 9.

18. The method of claim 1, wherein the heterologous glycoprotein is encoded by a nucleic acid sequence at least 80% identical to SEQ ID NOs: 6 or 8.

19. A method of treating cancer comprising administering to a subject with cancer a pharmaceutical composition comprising an effective amount of a chimeric Vesicular stomatitis virus (VSV) to treat the cancer, wherein the chimeric VSV's genome comprises nucleic acid sequences encoding a VSV nucleoprotein (N), VSV phosphoprotein (P), VSV matrix (M) protein, VSV large (L) viral polymerase, and a heterologous glycoprotein derived from Lassa virus comprising an amino acid sequence with at least 90% sequence identity to SEQ ID NO:2, and lacks a nucleic acid sequence encoding VSV glycoprotein (G).

20. A method of treating cancer comprising administering to a subject with cancer a pharmaceutical composition comprising an effective amount of a chimeric Vesicular stomatitis virus (VSV) to treat the cancer, wherein the chimeric VSV's genome comprises nucleic acid sequences encoding a VSV nucleoprotein (N), VSV phosphoprotein (P), VSV matrix (M) protein, VSV large (L) viral polymerase, and a heterologous glycoprotein derived from Ebola virus comprising an amino acid sequence with at least 90% sequence identity to SEQ ID NO:7 with or without the mucin domain, and lacks a nucleic acid sequence encoding VSV glycoprotein (G).

\* \* \* \* \*

SEQUENCE LISTING

```
<160> NUMBER OF SEQ ID NOS: 9

<210> SEQ ID NO 1
<211> LENGTH: 3401
<212> TYPE: DNA
<213> ORGANISM: Lassa virus

<400> SEQUENCE: 1
cgcaccgggg atcctaggca tttttggttg cgcaattcaa gtgtcctatt taaaatggga      60
caaatagtga cattcttcca ggaagtgcct catgtaatag aagaggtgat gaacattgtt     120
ctcattgcac tgtctgtact agcagtgctg aaaggtctgt acaattttgc aacgtgtggc     180
cttgttggtt tggtcacttt cctcctgttg tgtggtaggt cttgcacaac cagtctttat     240 aaagggttt atgagcttca gactctggaa ctaaacatgg agacactcaa tatgaccatg     300
cctctctcct gcacaaagaa caacagtcat cattatataa tggtgggcaa tgagacagga     360
ctagaactga ccttgaccaa cacgagcatt attaatcaca aattttgcaa tctgtctgat     420
gcccacaaaa agaacctcta tgaccacgct cttatgagca taatctcaac tttccacttg     480
tccatcccca acttcaatca gtatgaggca atgagctgcg attttaatgg gggaaagatt     540
agtgtgcagt acaacctgag tcacagctat gctggggatg cagccaacca ttgtggtact     600
gttgcaaatg gtgtgttaca gacttttatg aggatggctt ggggtgggag ctacattgct     660
cttgactcag gccgtggcaa ctgggactgt attatgacta gttatcaata tctgataatc     720
```

```
caaaatacaa cctgggaaga tcactgccaa ttctcgagac catctcccat cggttatctc    780
gggctcctct cacaaaggac tagagatatt tatattagta gaagattgct aggcacattc    840
acatggacac tgtcagattc tgaaggtaaa gacacaccag ggggatattg tctgaccagg    900
tggatgctaa ttgaggctga actaaaatgc ttcgggaaca cagctgtggc aaaatgtaat    960
gagaagcatg atgaggaatt ttgtgacatg ctgaggctgt ttgacttcaa caaacaagcc   1020
attcaaaggt tgaaagctga agcacaaatg agcattcagt tgatcaacaa agcagtaaat   1080
gctttgataa atgaccaact tataatgaag aaccatctac gggacatcat gggaattcca   1140
tactgtaatt acagcaagta ttggtacctc aaccacacaa ctactgggag aacatcactg   1200
cccaaatgtt ggcttgtatc aaatggttca tacttgaacg agacccactt ttctgatgat   1260
attgaacaac aagctgacaa tatgatcact gagatgttac agaaggagta tatggagagg   1320
caggggaaga caccattggg tctagttgac ctctttgtgt tcagtacaag tttctatctt   1380
attagcatct tccttcacct agtcaaaata ccaactcata ggcatattgt aggcaagtcg   1440
tgtcccaaac ctcacagatt gaatcatatg ggcatttgtt cctgtggact ctacaaacag   1500
cctggtgtgc ctgtgaaatg gaagagatga gaccttgtc agggcccccg tgacccaccg   1560
cctattggcg gtgggtcacg ggggcgtcca tttacagaac gactctaggt gtcgatgttc   1620
tgaacaccat atctctgggc agcactgctc caaaaccga tgtgttcagt cctcctgaca   1680
ctgctgcatc aaacatgatg cagtccatta gtgcacagtg agggggttatt tcctctttac   1740
cgcctctttt cttctttca acaacgacac ctgtgtgcat gtggcataag tctttatact   1800
ggtcccagac tgcattttca tacttcctgg aatcagtttt gctgagggca atatcaatta   1860
gtttaatgtc ttttcttcct tgtgattcaa ggagtttcct tatgtcatcg daccccctgac   1920
aggtaatgac catattccgg gggagtgcat caatgacagc actggtcaag cccggttgtg   1980
tagcgaagag gtctgtgaca tcaatcccat gtgagtactt agcatcctgc ttgaactgct   2040
ttaaatcagt aggttcacgg aagaagtgta tgtagcagcc tgaacttggt tgatagaggg   2100
caatttccac tggatcttca ggtcttcctt caatgtccat ccaggtctta gcatttgggt   2160
caagttgcag cattgcatcc ttgagggtca tcagctgaga ataggtaagc ccagcggtaa   2220
accctgccga ctgcagggat ttactggaat tgttgctgtc agctttctgt ggcttcccat   2280
ctgattccag atcaacgaca gtgttttccc aggcccttcc tgttattgag gttcttgatg   2340
caatatatgg ccatccatct cctgacaaac aaatcttgta gagtatgttt tcataaggat   2400
tcctttcacc aggggtgtct gaaatgaaca ttccaagagc cttcttgacc tttaaaatgg   2460
atttgaggat accatccatt gtctgaggtg acaccttgat tgtctccaac atattgccac   2520
catccagcat gcaagctcct gccttcacag ctgcacccaa gctaaaatta taacctgaga   2580
tattcaaaga gcttttcttg gtgtcaatca tatttaggat gggatgactt tgagtcagcc   2640
tgtctaagtc tgaagtgttg ggatactttg ctgtgtagat caaacccaaa tctgtcaatg   2700
cttgtactgc atcattcaag tcaacctgcc cctgttttgt cagacatgcc agtgtcagac   2760
ttggcatggt cccgaactga ttattgagca actctgcatt tttcacatcc caaactctca   2820
ccactccatc tctcccagcc cgagcccctt gattaccacc actcattcct atcatattca   2880
ggagagctct tctttggtca agttgctgtg agcttaggtt gcccatatag acacctgcac   2940
ttaatggcct ttctgttctg atcacctttg actttaactt ctctagatca gcggctaaga   3000
ttaataagtc atctgaggtt agagtcccaa ctctcagtat actctttttgt tgagttgatt   3060
```

-continued

```
ttaattcaac aagattgttg accgcttgat ttaggtccct caaccgtttc aaatcattgt    3120
catcccttct ctccttgcgc atcaaccgtt gaacattact gacttcggag aagtcaagtc    3180
catgtaaaag agcctgggca tctttcacca cctgtagttt gatgttggag cagtaaccag    3240
ataattccct cctcaaagat tgtgtccaca aaaaggattt tatttccttt gaggcactca    3300
tcgccagatt gttgtgttgt atgcacgcaa caaagaactg agactatctg ccaaaatgac    3360
aaaagcaaag cgcaatccaa tagcctagga tccactgtgc g    3401
```

<210> SEQ ID NO 2
<211> LENGTH: 491
<212> TYPE: PRT
<213> ORGANISM: Lassa virus

<400> SEQUENCE: 2

```
Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
            20                  25                  30

Lys Gly Leu Tyr Asn Phe Ala Thr Cys Gly Leu Val Gly Leu Val Thr
        35                  40                  45

Phe Leu Leu Leu Cys Gly Arg Ser Cys Thr Thr Ser Leu Tyr Lys Gly
    50                  55                  60

Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
            100                 105                 110

Ile Asn His Lys Phe Cys Asn Leu Ser Asp Ala His Lys Lys Asn Leu
        115                 120                 125

Tyr Asp His Ala Leu Met Ser Ile Ile Ser Thr Phe His Leu Ser Ile
    130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
            180                 185                 190

Arg Met Ala Trp Gly Gly Ser Tyr Ile Ala Leu Asp Ser Gly Arg Gly
        195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
        275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320
```

-continued

```
Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
                340                 345                 350

Asn His Leu Arg Asp Ile Met Gly Ile Pro Tyr Cys Asn Tyr Ser Lys
            355                 360                 365

Tyr Trp Tyr Leu Asn His Thr Thr Thr Gly Arg Thr Ser Leu Pro Lys
        370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
                420                 425                 430

Leu Phe Val Phe Ser Thr Ser Phe Tyr Leu Ile Ser Ile Phe Leu His
            435                 440                 445

Leu Val Lys Ile Pro Thr His Arg His Ile Val Gly Lys Ser Cys Pro
        450                 455                 460

Lys Pro His Arg Leu Asn His Met Gly Ile Cys Ser Cys Gly Leu Tyr
465                 470                 475                 480

Lys Gln Pro Gly Val Pro Val Lys Trp Lys Arg
                485                 490
```

<210> SEQ ID NO 3
<211> LENGTH: 569
<212> TYPE: PRT
<213> ORGANISM: Lassa virus

<400> SEQUENCE: 3

```
Met Ser Ala Ser Lys Glu Ile Lys Ser Phe Leu Trp Thr Gln Ser Leu
1               5                   10                  15

Arg Arg Glu Leu Ser Gly Tyr Cys Ser Asn Ile Lys Leu Gln Val Val
                20                  25                  30

Lys Asp Ala Gln Ala Leu Leu His Gly Leu Asp Phe Ser Glu Val Ser
            35                  40                  45

Asn Val Gln Arg Leu Met Arg Lys Glu Arg Arg Asp Asp Asn Asp Leu
        50                  55                  60

Lys Arg Leu Arg Asp Leu Asn Gln Ala Val Asn Asn Leu Val Glu Leu
65                  70                  75                  80

Lys Ser Thr Gln Gln Lys Ser Ile Leu Arg Val Gly Thr Leu Thr Ser
                85                  90                  95

Asp Asp Leu Leu Ile Leu Ala Ala Asp Leu Glu Lys Leu Lys Ser Lys
                100                 105                 110

Val Ile Arg Thr Glu Arg Pro Leu Ser Ala Gly Val Tyr Met Gly Asn
            115                 120                 125

Leu Ser Ser Gln Gln Leu Asp Gln Arg Arg Ala Leu Leu Asn Met Ile
        130                 135                 140

Gly Met Ser Gly Gly Asn Gln Gly Ala Arg Ala Gly Arg Asp Gly Val
145                 150                 155                 160

Val Arg Val Trp Asp Val Lys Asn Ala Glu Leu Leu Asn Asn Gln Phe
                165                 170                 175

Gly Thr Met Pro Ser Leu Thr Leu Ala Cys Leu Thr Lys Gln Gly Gln
                180                 185                 190

Val Asp Leu Asn Asp Ala Val Gln Ala Leu Thr Asp Leu Gly Leu Ile
```

```
                195                 200                 205
Tyr Thr Ala Lys Tyr Pro Asn Thr Ser Asp Leu Asp Arg Leu Thr Gln
210                 215                 220

Ser His Pro Ile Leu Asn Met Ile Asp Thr Lys Lys Ser Ser Leu Asn
225                 230                 235                 240

Ile Ser Gly Tyr Asn Phe Ser Leu Gly Ala Ala Val Lys Ala Gly Ala
            245                 250                 255

Cys Met Leu Asp Gly Gly Asn Met Leu Glu Thr Ile Lys Val Ser Pro
        260                 265                 270

Gln Thr Met Asp Gly Ile Leu Lys Ser Ile Leu Lys Val Lys Lys Ala
    275                 280                 285

Leu Gly Met Phe Ile Ser Asp Thr Pro Gly Glu Arg Asn Pro Tyr Glu
290                 295                 300

Asn Ile Leu Tyr Lys Ile Cys Leu Ser Gly Asp Gly Trp Pro Tyr Ile
305                 310                 315                 320

Ala Ser Arg Thr Ser Ile Thr Gly Arg Ala Trp Glu Asn Thr Val Val
            325                 330                 335

Asp Leu Glu Ser Asp Gly Lys Pro Gln Lys Ala Asp Ser Asn Asn Ser
        340                 345                 350

Ser Lys Ser Leu Gln Ser Ala Gly Phe Thr Ala Gly Leu Thr Tyr Ser
    355                 360                 365

Gln Leu Met Thr Leu Lys Asp Ala Met Leu Gln Leu Asp Pro Asn Ala
370                 375                 380

Lys Thr Trp Met Asp Ile Glu Gly Arg Pro Glu Asp Pro Val Glu Ile
385                 390                 395                 400

Ala Leu Tyr Gln Pro Ser Ser Gly Cys Tyr Ile His Phe Phe Arg Glu
            405                 410                 415

Pro Thr Asp Leu Lys Gln Phe Lys Gln Asp Ala Lys Tyr Ser His Gly
        420                 425                 430

Ile Asp Val Thr Asp Leu Phe Ala Thr Gln Pro Gly Leu Thr Ser Ala
    435                 440                 445

Val Ile Asp Ala Leu Pro Arg Asn Met Val Ile Thr Cys Gln Gly Ser
450                 455                 460

Asp Asp Ile Arg Lys Leu Leu Glu Ser Gln Gly Arg Lys Asp Ile Lys
465                 470                 475                 480

Leu Ile Asp Ile Ala Leu Ser Lys Thr Asp Ser Arg Lys Tyr Glu Asn
            485                 490                 495

Ala Val Trp Asp Gln Tyr Lys Asp Leu Cys His Met His Thr Gly Val
        500                 505                 510

Val Val Glu Lys Lys Lys Arg Gly Gly Lys Glu Glu Ile Thr Pro His
    515                 520                 525

Cys Ala Leu Met Asp Cys Ile Met Phe Asp Ala Ala Val Ser Gly Gly
530                 535                 540

Leu Asn Thr Ser Val Leu Arg Ala Val Leu Pro Arg Asp Met Val Phe
545                 550                 555                 560

Arg Thr Ser Thr Pro Arg Val Val Leu
            565

<210> SEQ ID NO 4
<211> LENGTH: 34
<212> TYPE: DNA
<213> ORGANISM: Artificial Sequence
<220> FEATURE:
<223> OTHER INFORMATION: DNA Primer
```

<400> SEQUENCE: 4

```
gcgacgcgta ccatgggaca aatagtgaca ttct                          34
```

<210> SEQ ID NO 5
<211> LENGTH: 30
<212> TYPE: DNA
<213> ORGANISM: Artificial Sequence
<220> FEATURE:
<223> OTHER INFORMATION: DNA Primer

<400> SEQUENCE: 5

```
ggcggccgct catctcttcc atttcacagg                               30
```

<210> SEQ ID NO 6
<211> LENGTH: 2031
<212> TYPE: DNA
<213> ORGANISM: Ebola virus Zaire strain

<400> SEQUENCE: 6

```
atgggcgtta caggaatatt gcagttacct cgtgatcgat tcaagaggac atcattcttt    60
ctttgggtaa ttatcctttt ccaaagaaca ttttccatcc cacttggagt catccacaat   120
agcacattac aggttagtga tgtcgacaaa ctagtttgtc gtgacaaact gtcatccaca   180
aatcaattga gatcagttgg actgaatctc gaagggaatg gagtggcaac tgacgtgcca   240
tctgcaacta aagatggggg cttcaggtcc ggtgtcccac caaaggtggt caattatgaa   300
gctggtgaat gggctgaaaa ctgctacaat cttgaaatca aaaaacctga cgggagtgag   360
tgtctaccag cagcgccaga cgggattcgg gcttccccc ggtgccggta tgtgcacaaa   420
gtatcaggaa cgggaccgtg tgccggagac tttgccttcc ataaagaggg tgctttcttc   480
ctgtatgatc gacttgcttc cacagttatc taccgaggaa cgactttcgc tgaaggtgtc   540
gttgcatttc tgatactgcc ccaagctaag aaggacttct cagctcaca ccccttgaga   600
gagccggtca tgcaacggga ggacccgtct agtggctact attctaccac aattagatat   660
caggctaccg gttttggaac caatgagaca gagtacttgt tcgaggttga caatttgacc   720
tacgtccaac ttgaatcaag attcacacca cagtttctgc tccagctgaa tgagacaata   780
tatacaagtg ggaaaaggag caataccacg ggaaaactaa tttggaaggt caaccccgaa   840
attgatacaa caatcgggga gtgggccttc tgggaaacta aaaaaaacct cactagaaaa   900
attcgcagtg aagagttgtc tttcacagtt gtatcaaacg gagccaaaaa catcagtggt   960
cagagtccgg cgcgaacttc ttccgaccca gggaccaaca caacaactga agaccacaaa  1020
atcatggctt cagaaaattc ctctgcaatg gttcaagtgc acagtcaagg aagggaagct  1080
gcagtgtcgc atctaacaac ccttgccaca atctccacga gtcccccaatc cctcacaacc  1140
aaaccaggtc cggacaacag cacccataat acacccgtgt ataaacttga catctctgag  1200
gcaactcaag ttgaacaaca tcaccgcaga acagacaacg acagcacagc ctccgacact  1260
ccctctgcca cgaccgcagc cggaccccca aaagcagaga caccaacac gagcaagagc  1320
actgacttcc tggaccccgc caccacaaca gtccccaaa ccacagcga ccgctggc    1380
aacaacaaca ctcatcacca agataccgga gaagagagtg ccagcagcgg gaagctaggc  1440
ttaattacca atactattgc tggagtcgca ggactgatca caggcgggag aagaactcga  1500
agagaagcaa ttgtcaatgc tcaacccaaa tgcaacccta atttacatta ctggactact  1560
caggatgaag tgctgcaat cggactggcc tggataccat atttcgggcc agcagccgag  1620
ggaatttaca tagagggggct aatgcacaat caagatggtt taatctgtgg gttgagacag  1680
```

```
ctggccaacg agacgactca agctcttcaa ctgttcctga gagccacaac tgagctacgc    1740 acctttcaa tcctcaaccg taaggcaatt gatttcttgc tgcagcgatg gggcggcaca     1800
tgccacattc tgggaccgga ctgctgtatc gaaccacatg attggaccaa gaacataaca    1860
gacaaaattg atcagattat tcatgatttt gttgataaaa cccttccgga ccaggggac    1920 aatgacaatt ggtggacagg atggagacaa tggataccgg caggtattgg agttacaggc    1980
gttataattg cagttatcgc tttattctgt atatgcaaat ttgtctttta g             2031
```

<210> SEQ ID NO 7
<211> LENGTH: 676
<212> TYPE: PRT
<213> ORGANISM: Ebola virus Zaire strain

<400> SEQUENCE: 7

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
```

```
                305                 310                 315                 320
Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
                355                 360                 365

Ala Thr Ile Ser Thr Ser Pro Gln Ser Leu Thr Thr Lys Pro Gly Pro
                370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Ala Ala Gly Pro Pro Lys Ala
                420                 425                 430

Glu Asn Thr Asn Thr Ser Lys Ser Thr Asp Phe Leu Asp Pro Ala Thr
                435                 440                 445

Thr Thr Ser Pro Gln Asn His Ser Glu Thr Ala Gly Asn Asn Asn Thr
                450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
                500                 505                 510

Pro Asn Leu His Tyr Trp Thr Thr Gln Asp Glu Gly Ala Ala Ile Gly
                515                 520                 525

Leu Ala Trp Ile Pro Tyr Phe Gly Pro Ala Ala Glu Gly Ile Tyr Ile
                530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
                660                 665                 670

Lys Phe Val Phe
            675
```

<210> SEQ ID NO 8
<211> LENGTH: 1494
<212> TYPE: DNA
<213> ORGANISM: Ebola virus Zaire strain

<400> SEQUENCE: 8

```
atgggcgtta caggaatatt gcagttacct cgtgatcgat tcaagaggac atcattcttt      60
ctttgggtaa ttatccttt  ccaaagaaca ttttccatcc cacttggagt catccacagt     120
agcacattac aggttagtga tgtcgacaaa ctagtttgtc gtgacaaact gtcatccaca     180
aatcaattga gatcagttgg actgaatctc gaagggaatg gagtggcaac tgacgtgcca     240
tctgcaacta aagatggggg cttcaggtcc ggtgtcccac caaaggtggt caattatgaa     300
gctggtgaat gggctgaaaa ctgctacaat cttgaaatca aaaaacctga cgggagtgag     360
tgtctaccag cagcgccaga cgggattcgg ggcttccccc ggtgccggta tgtgcacaaa     420
gtatcaggaa cgggaccgtg tgccggagac tttgccttcc ataaagaggg tgctttcttc     480
ctgtatgatc gacttgcttc cacagttatc taccgaggaa cgactttcgc tgaaggtgtc     540
gttgcatttc tgatactgcc ccaagctaag aaggacttct tcagctcaca ccccttgaga     600
gagccggtca tgcaacgga  ggacccgtct agtggctact attctaccac aattagatat     660
caggctaccg ttttggaac  caatgagaca gagtacttgt tcgaggttga catttgacc      720
tacgtccaac ttgaatcaag attcacacca cagtttctgc tccagctgaa tgagacaata     780
tatacaagtg ggaaaggag  caataccacg ggaaaactaa tttggaaggt caaccccgaa     840
attgataca  caatcgggga gtgggccttc tgggaaacta aaaaaaacct cactagaaaa     900
attcgcagtg aagagttgtc tttctctaga gcaggactga tcacaggcgg agaagaact      960
cgaagagaag caattgtcaa tgctcaaccc aaatgcaacc ctaatttaca ttactggact    1020
actcaggatg aaggtgctgc aatcggactg gcctggatac catatttcgg ccagcagcc    1080
gagggaattt acatagaggg gctaatgcac aatcaagatg gtttaatctg tgggttgaga    1140
cagctggcca acgagacgac tcaagctctt caactgttcc tgagagccac aactgagcta    1200
cgcaccttt  caatcctcaa ccgtaaggca attgatttct tgctgcagcg atggggcggc    1260
acatgccaca ttctgggacc ggactgctgt atcgaaccac atgattggac caagaacata    1320
acagacaaaa ttgatcagat tattcatgat tttgttgata aaacccttcc ggaccagggg    1380
gacaatgaca attggtggac aggatggaga caatggatac cggcaggtat tggagttaca    1440
ggcgttgtaa ttgcagttat cgctttattc tgtatatgca aatttgtctt ttag          1494
```

<210> SEQ ID NO 9
<211> LENGTH: 497
<212> TYPE: PRT
<213> ORGANISM: Ebola virus Zaire strain

<400> SEQUENCE: 9

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Ser Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110
```

```
Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Ser Arg Ala Gly Leu Ile Thr Gly Gly Arg Arg Thr
305                 310                 315                 320

Arg Arg Glu Ala Ile Val Asn Ala Gln Pro Lys Cys Asn Pro Asn Leu
                325                 330                 335

His Tyr Trp Thr Thr Gln Asp Glu Gly Ala Ala Ile Gly Leu Ala Trp
            340                 345                 350

Ile Pro Tyr Phe Gly Pro Ala Ala Glu Gly Ile Tyr Ile Glu Gly Leu
        355                 360                 365

Met His Asn Gln Asp Gly Leu Ile Cys Gly Leu Arg Gln Leu Ala Asn
    370                 375                 380

Glu Thr Thr Gln Ala Leu Gln Leu Phe Leu Arg Ala Thr Thr Glu Leu
385                 390                 395                 400

Arg Thr Phe Ser Ile Leu Asn Arg Lys Ala Ile Asp Phe Leu Leu Gln
                405                 410                 415

Arg Trp Gly Gly Thr Cys His Ile Leu Gly Pro Asp Cys Cys Ile Glu
            420                 425                 430

Pro His Asp Trp Thr Lys Asn Ile Thr Asp Lys Ile Asp Gln Ile Ile
        435                 440                 445

His Asp Phe Val Asp Lys Thr Leu Pro Asp Gln Gly Asp Asn Asp Asn
    450                 455                 460

Trp Trp Thr Gly Trp Arg Gln Trp Ile Pro Ala Gly Ile Gly Val Thr
465                 470                 475                 480

Gly Val Val Ile Ala Val Ile Ala Leu Phe Cys Ile Cys Lys Phe Val
                485                 490                 495

Phe
```